United States Patent
Al-Babili et al.

(10) Patent No.: US 11,903,386 B2
(45) Date of Patent: Feb. 20, 2024

(54) STRIGOLACTONE ANALOGS AND THEIR USAGE IN PLANT CONTROL

(71) Applicant: King Abdullah University of Science and Technology, Thuwal (SA)

(72) Inventors: Salim Al-Babili, Thuwal (SA); Tadao Asami, Tokyo (JP); Tsuyoshi Ohta, Tokyo (JP)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 676 days.

(21) Appl. No.: 16/337,198

(22) PCT Filed: Sep. 27, 2017

(86) PCT No.: PCT/IB2017/055877
§ 371 (c)(1),
(2) Date: Mar. 27, 2019

(87) PCT Pub. No.: WO2018/060865
PCT Pub. Date: Apr. 5, 2018

(65) Prior Publication Data
US 2019/0357534 A1      Nov. 28, 2019

Related U.S. Application Data

(60) Provisional application No. 62/400,506, filed on Sep. 27, 2016.

(51) Int. Cl.
*A01N 43/08* (2006.01)
*C07D 307/60* (2006.01)

(52) U.S. Cl.
CPC ........... *A01N 43/08* (2013.01); *C07D 307/60* (2013.01)

(58) Field of Classification Search
CPC .............................. A01N 43/08; C07D 307/60
See application file for complete search history.

(56) References Cited

U.S. PATENT DOCUMENTS

| | | |
|---|---|---|
| 8,980,795 B2 | 3/2015 | Al-Babili |
| 2015/0141255 A1 | 5/2015 | Boyer |
| 2015/0274690 A1 | 10/2015 | Davidson |

FOREIGN PATENT DOCUMENTS

WO      2010137662      12/2010

OTHER PUBLICATIONS

J. Thuring et al., "Synthesis and biological evaluation of strigol analogues modified in the enol ether part," J. Chem. Soc., Perkin Trans. 1, 1997, pp. 767-774.*

E. M Mangnus, "Strigol Analogues: Design, Synthesis and Biological Activity," Radboud University Nijmeen, published 2006, pp. 1-135.*
Abe, et al., "Carlactone is converted to carlactonic acid by MAX1 in *Arabidopsis* and its methyl ester can directly interact with AtD14 in vitro", PNAS, 111:18084-18089 (2014).
Agusti, et al., "Strigolactone signaling is required for auxin-dependent stimulation of secondary growth in plants", PNAS, 108:20242-20247 (2011).
Akiyama, et al., "Plant sesquiterpenes induce hyphal branching in arbuscular mycorrhizal fungi", Nature, 435:824-827 (2005).
Al-Babili, et al., "Strigolactones, a novel carotenoid-derived plant hormone", Annual Review of Plant Biology, 66:161-186 (2015).
Alder, et al., "The path from beta-carotene to carlactone, a Strigolactone-like plant hormone", Science, 335:1348-1351 (2012).
Beveridge, "Strigolactones", Current Biology, 24:987-988 (2014).
Booker, et al., "MAX1 encodes a cytochrome P450 family member that acts downstream of MAX3/4 to produce a carotenoid-derived branch-inhibiting hormone", Developmental Cell, 8:443-449 (2005).
Boyer, et al., "New Strigolactone analogs as plant hormones with low activities in the rhizosphere", Molecular Plant, 7(4):675-690 (2014).
Brewer, et al., "Lateral Branching Oxidoreductase acts in the final stages of Strigolactone biosynthesis in *Arabidopsis*", PNAS, 113:6301-6306 (2016).
Bruno, et al., "Insights into the formation of carlactone from in depth analysis of the CCD8 catalyzed reactions", FEBS Letters, 591:792-800 (2017).
Bruno, et al., "On the substrate and stereospecificity of the plant Carotenoid Cleavage Dioxygenase 7", FEBS Letters, 588:1802-1807 (2014).
Bruno, et al., "On the substrate specificity of the rice Strigolactone biosynthesis enzyme Dwarf27", Planta, 243:1429-1440 (2016).
Cavar, et al., "Strigolactones: occurrence, structure, and biological activity in the rhizosphere", Phytochemistry Reviews, 2015:691-711 (2014).

(Continued)

*Primary Examiner* — Monica A Shin
(74) *Attorney, Agent, or Firm* — PABST PATENT GROUP LLP

(57) ABSTRACT

A strigolactone analog-based composition comprising at least one compound represented by: (I) wherein Ra, Rb, Rc, Rf, Re, and Rz are selected. The compositions can be used in, for example, plant growth regulation and weed control, including controlling the germination of parasitic root plants, inhibiting rice tillering, and triggering leaf senescence.

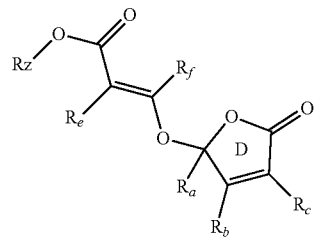

15 Claims, 19 Drawing Sheets
Specification includes a Sequence Listing.

(56) References Cited

OTHER PUBLICATIONS

Charnikhova, et al., "Novel natural strigolactones from maize", Phytochemistry, 137:123-131 (2017).
Conn, et al., "Convergent evolution of Strigolactone perception enabled host detection in parasitic plants", Science, 349:540-543 (2015).
De Saint Germain, et al., "A histidine covalent receptor and butenolide complex mediates Strigolactone perception", Nature Chemical Biology, 12:787-795 (2016).
Decker, et al., "Strigolactone biosynthesis is evolutionarily conserved, regulated by phosphate starvation and contributes to resistance against phytopathogenic fungi in a moss, *Physcomitelia patens*", New Phytologist., (2017).
Delavault, et al., "Communication between host plants and parasitic plants", Advances in Botanical Research, 82:1-28 (2016).
Dor, et al., "The synthetic Strigolactone GR24 influences growth pattern of phytopathogenic fungi", Planta, 234:419-427 (2011).
Ejeta, et al., "Breeding for Striga resistance in sorghum: Exploitation of intricate host-parasite biology", Crop Science, 47:216-227 (2007).
Foo, et al., "Strigolactones promote nodulation in pea", Planta, 234:1073-1081 (2011).
Fukui, et al., "Selective mimics of Strigolactone actions and their potential use for controlling damage caused by root parasitic weeds", Molecular Plant, 6:88-99 (2013).
Gomez-Roldan, et al., "Strigolactone inhibition of shoot branching", Nature, 455:189-194 (2008).
Gutjahr, et al., "Cell and developmental biology of arbuscular mycorrhiza symbiosis", Annual review of cell and developmental biology, 29:593-617 (2013).
Ha, et al., "Positive regulatory role of Strigolactone in plant responses to drought and salt stress", PNAS, 111:851-856 (2014).
Hamiaux, et al., "DAD2 is an alpha/beta hydrolase likely to be involved in the perception of the plant branching hormone, Strigolactone", Current Biology, 22:2032-2036 (2012).
Hearne, et al., "Control—the Striga conundrum", Pest Management Science, 65:603-614 (2009).
Humphrey, et al., "Strigolactones in chemical ecology: waste products or vital allelochemicals", Natural Product Reports, 23:592-614 (2006).
Jamil, et al., "Striga hermonthica parasitism in maize in response to N and P fertilisers", Field Crops Research, 134:1-10 (2012).
Jia, et al., "Nitro-Phenlactone, a carlactone analog with pleiotropic Strigolactone activities", Molecular Plant, 9:1341-1344 (2016).
Jiang, et al., "Dwarf 53 acts as a repressor of Strigolactone signaling in rice", Nature, 506:401-411 (2013).
Joel, et al., "The long-term approach to parasitic weeds control: manipulation of specific developmental mechanisms of the parasite", Crop Protection, 19:753-758 (2000).
Kgosi, et al., "Strigolactone analogues induce suicidal seed germination of *Striga* spp. in soil", Weed Research, 52:197-203 (2012).
Kondo, et al., "Synthesis and Seed Germination Stimulating Activity of Some Imino Analogs of Strigolactones", Bioscience, Biotechnology and biochemistry, 71(11): 2781-2786 (2007).
Lopez-Obando, et al., "Strigolactones biosynthesis and signaling in plant development", Development, 42:3615-3619 (2015).
Lumba, et al., "The perception of strigolactones in vascular plants", Nature Chemical Biology, 13:599-606 (2017).
Malik, et al., "Aromatic A-ring analogues of orobanchol, new germination stimulants for seeds of parasitic weeds", Organic & Biomolecular Chemistry, 9:2286-2293 (2011).
Mangnus, et al., "Structural modification of strigol analogs-influence of the B and C rings on the bioactivity of the germination stimulant GR24", Journal of Agricultural and Food Chemistry, 40:1222-1229 (1992).
Matthys, et al., "The Whats, the Wheres and the Hows of Strigolactone action in the roots", Planta, 243:1327-1337 (2016).
Matusova, et al., "The Strigolactone germination stimulants of the plant-parasitic *Striga* and *Orobanche* spp. Are derived from the carotenoid pathway", Plant physiology, 139:920-934 (2005).
Morffy, et al., "Smoke and Hormone Mirrors: Action and Evolution of Karrikin and Strigolactone Signaling", Trends in genetics: TIG, 32:176-188 (2016).
Nelson, et al., "Regulation of seed germination and seedling growth by chemical signals from burning vegetation", Annual Review of Plant Biology, 63:107-130 (2012).
Parker, "Observations on the current status of Orobanche and Striga problems worldwide", Pest Management Service, 65:453-459 (2009).
Parker, "Parasitic weeds: a world challenge", Weed Science, 60:269-276 (2012).
Pennisi, "Armed and dangerous", Science, 327:804-805 (2010).
Rasmussen, et al., "Strigolactones suppress adventitious rooting in *Arabidopsis* and Pea", Plant Physiology, 158:1976-1987 (2012).
Reizelman, et al., "Synthesis of all eight stereoisomers of the germination stimulant strigol", Synthesis, 13:1944-1951 (2000).
Ritz, et al., "Bioassay analysis using R", Journal of Statistical Software, 12:1-22 (2005).
Rodenburg, et al., "Genetic variation and host-parasite specificity of Striga resistance and tolerance in rice: the need for predictive breeding", New Phytologist, 214:1267-1280 (2017).
Ruyter-Spira, et al., "The biology of strigolactones", Trends in Plant Science, 18:72-83 (2013).
Samejima, et al., "Practicality of the suicidal germination approach for controlling Striga hermonthica", Pest Management Science, 72:2035-2042 (2016).
Screpanti, et al., "Strigolactone derivatives for potential crop enhancement applications", Bioorganic & Medicinal Chemistry Letters, 26:2392-2400 (2016).
Seto, et al., "Carlactone is an endogenous biosynthetic precursor for strigolactones", PNAS, 111:1640-1645 (2014).
Stirnberg, et al., "MAX2 participates in an SCF complex which acts locally at the node to suppress shoot branching", Plant Journal, 50:80-94 (2007).
Tank, et al., "Review of the systematics of Scrophulariaceae s.l. and their current disposition", Australian Systematic Botany, 19:289-307 (2006).
Thuring, et al., "Synthesis and biological evaluation of strigol analogues modified in the enol ether part", Journal of The Chemical Society Perkin Transactions 1, 1997(5):767-774 (1997).
Torres-Vera, et al., "Do strigolactones contribute to plant defense", Molecular Plant Pathology, 15:211-216 (2014).
Tsuchiya, et al., "Probing Strigolactone receptors in Striga hermothica with fluorescence", Science, 349:864-868 (2015).
Ueno, et al., "Heliolactone, a non-sesquiterpine lactone germination stimulant for root parasitic weeds from sunflower", Phytochemistry, 108:122-128 (2014).
Ueno, et al., "Structural requirements of strigolactones for germination induction of Striga gesnerioides seeds", Journal of Agricultural and Food Chemistry, 59:9226-9231 (2011).
Umehara, et al., "Inhibition of shoot branching by new terpenoid plant hormones", Nature, 455:195-200 (2008).
Waters, et al., "Strigolactone signaling and evolution", Annu. Rev. Plant Biol., 68:916-925 (2017).
Wigchert, et al., "Dose-response of seeds of the parasitic weeds Striga and Orobanche toward the synthetic germination stimulants GR 24 and Nijmegen-1", Journal of Agricultural Food and Chemistry, 47:1705-1710 (1999).
Wu, et al., "Cryptochrome 1 is implicated in promoting R protein mediated plant resistance to Pseudomonas syringae in *Arabidopsis*", Molecular Plant, 3:539-548 (2010).
Xie, et al., "Confirming stereochemical structures of strigolactones by rice and tobacco", Molecular Plant, 6:153-163 (2013).
Xie, et al., "The Strigolactone story", Annual Review of Pathology, 48:93-117 (2010).
Yamada, et al., "Strigolactone signaling requires rice leaf senescence in response to a phosphate deficiency", Planta, 240: 399-408 (2014).
Yao, et al., "Dwarf14 is a non-canonical hormone receptor for Strigolactone", Nature, 536:469-473 (2016).

(56) References Cited

OTHER PUBLICATIONS

Yoneyama, et al., "Strigolactones as germination stimulants for root parasitic plants", Plant & cell physiology, 51: 1095-1103 (2010).
Zhang, et al., "Rice cytochrome P450 MAX1 homologs catalyze distinct steps in Strigolactone biosynthesis", Nature Chemical Biology, 10:1028-1033 (2014).
Zhou, et al. D14-SCFD3-dependent degradation of D53 regulates Strigolactone signaling, Nature, 504:406-410 (2013).
Zwanenburg, et al., "Strigolactones: new plant hormones in action", Planta, 243:1311-1326 (2016).
Zwanenburg, et al., "Structure and activity of strigolactones: New plant hormones with a rich future", Molecular Plant, 6:38-62 (2013b).
Zwanenburg, et al., "Structure and function of natural and synthetic signaling molecules in parasitic weed germination", Pest Management science, 65:478-491 (2009).
Zwanenburg, et al., "Structure-activity relationship and mode of action as germinating stimulants for parasitic weeds", Bioorganic & Medicinal Chemistry Letters, 23:5182-5186 (2013a).
International Search Report for corresponding PCT application PCT/IB2017/055877 dated Mar. 6, 2018.

\* cited by examiner

Stability analysis of MPs in comparison to GR24. The stability of MPs was monitored daily for 3 weeks. Data are means ± SE ($n=3$). X-axis (time (days)); Y-axis (substrate).

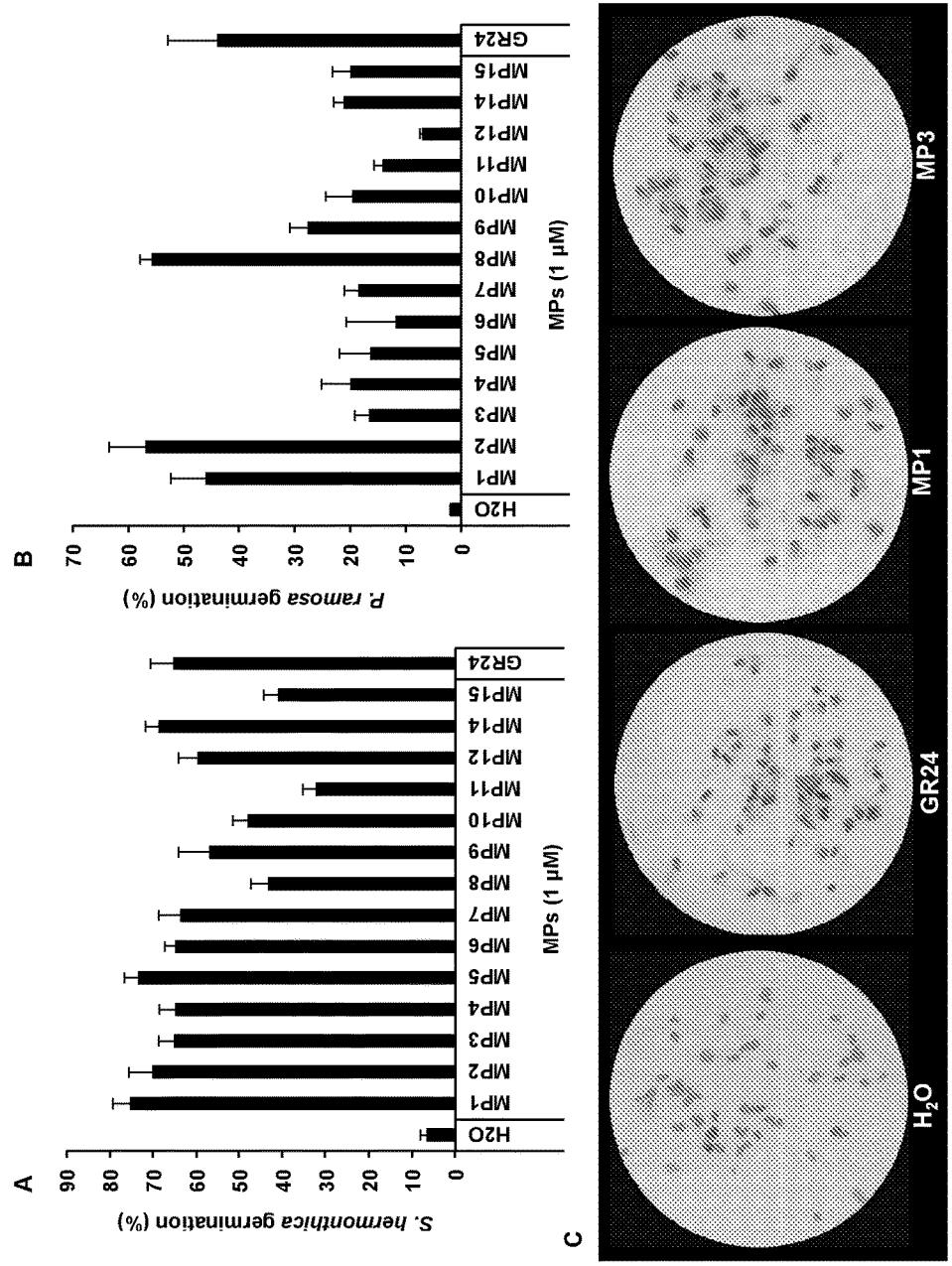

Figure 10

*Striga hermonthica* seed germination in response to MPs treatment. (A) Each MP was applied in 50 µl volume (1.0 µM) on a disc containing 50-100 pre-conditioned *Striga* seeds. H2O and GR24 are included as negative and positive control, respectively. (B) *P. ramosa* seed germination in response to MPs application. 50 µl of each MP was applied (1.0 µM) on a disc containing 50-100 preconditioned *P. ramosa* seeds. Bars represented means ± SE (*n*=3). (C) Picture showing *S. hermonthica* seed germination bioassay.

Effect of MPs on rice fresh biomass. MPs were applied (2.5 µM) to one week old hydroponically grown rice seedlings (Shiokari, *d3, d10*) twice a week for three weeks. Bars represent means ± SE (*n*=8).

Picture showing the effect of MPs (MP1, MP3, MP7) and GR24, applied at concentration ranging from $2.5\mu M - 2.5\times10^{-7} \mu M$, on tillering and growth of *d10* seedlings.

Effect of MPs on Arabidopsis hypocotyl length. Eight days old Arabidopsis seedlings (at least 30) were photographed digitally and, measurement of the hypocotyl length was conducted using ImageJ software. Bars represent means ± SE.

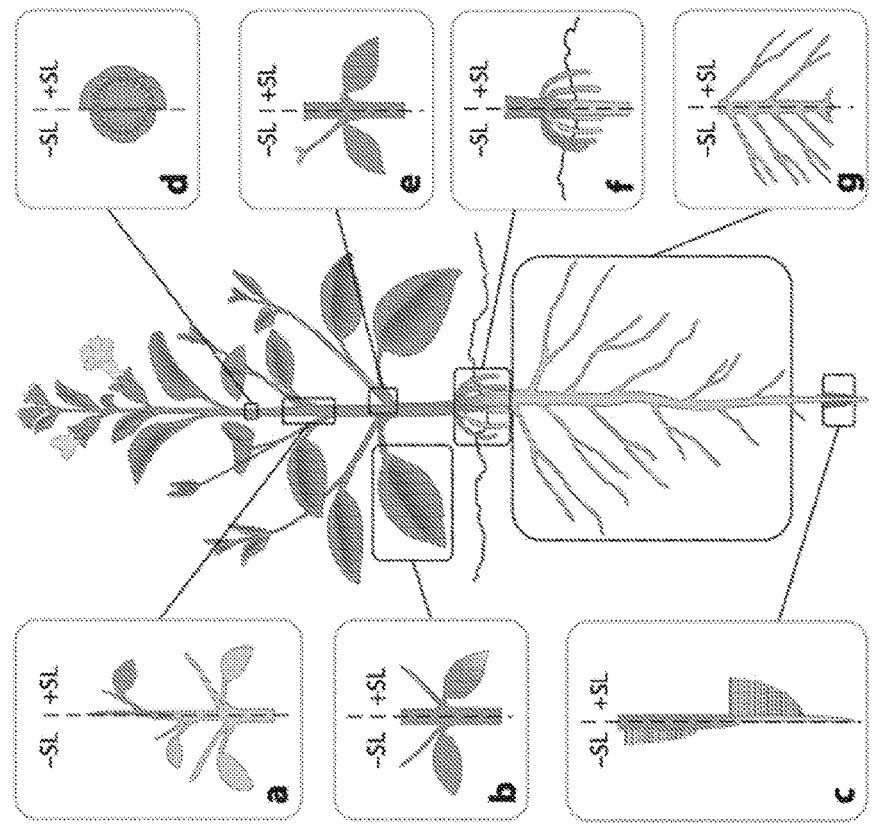

Figure 14. Developmental functions of SLs. SLs (a) regulate the growth of internodes, (b) accelerate leaf senescence, (c) lead to elongation of root hairs and trigger the growth of primary roots, (d) enhance stem thickness and induce secondary growth, (e) reduce the number of shoot branches, and inhibit the formation of (f) adventitious and (g) lateral roots. Figure published in (Al-Babili & Bouwmeester reference, 2015, Part One, Reference One).

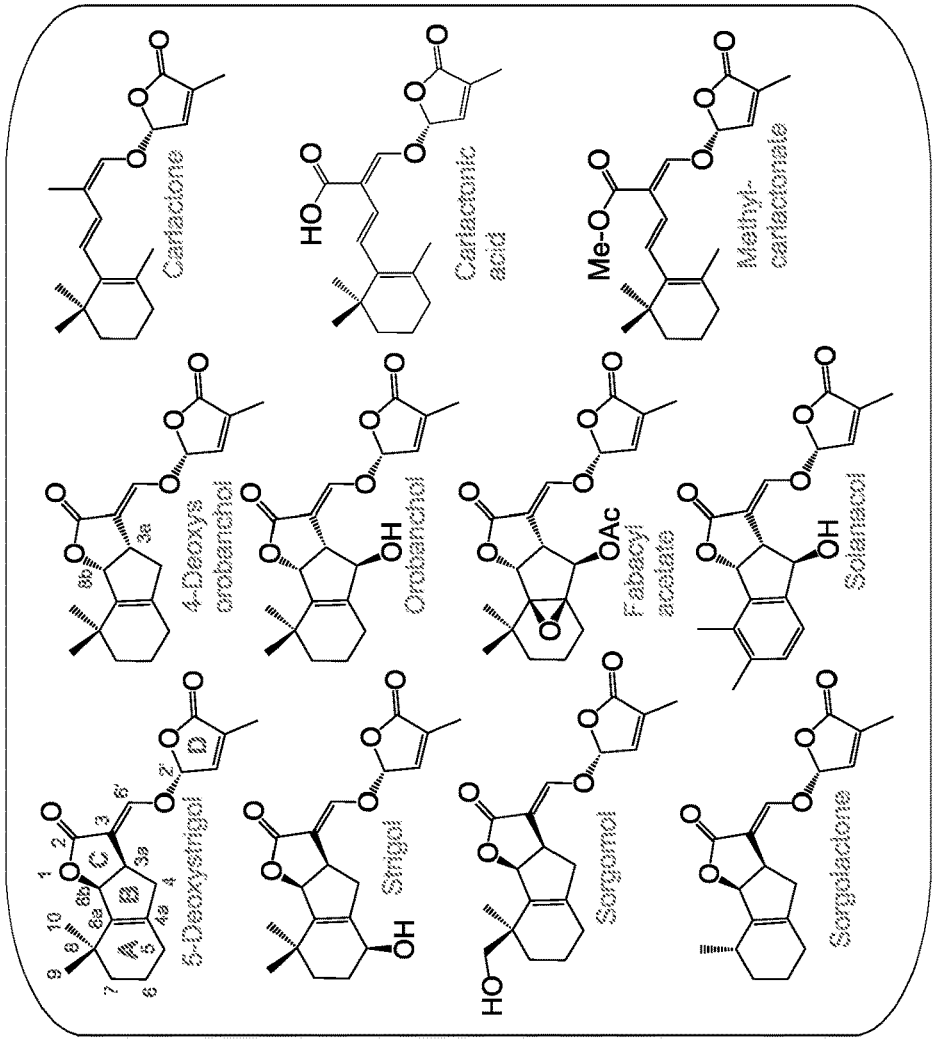
Figure 15. Structures of Strigolactones. C-atom numbering and the characteristic ABC-D-ring are shown in the structure of 5-deoxystrigol. Examples of strigol-like strigolactones with the C-ring in β orientation (left column) and orobanchol-like with the C-ring in an alpha orientation (middle column). Carlactone and derivatives of are depicted in the right column.

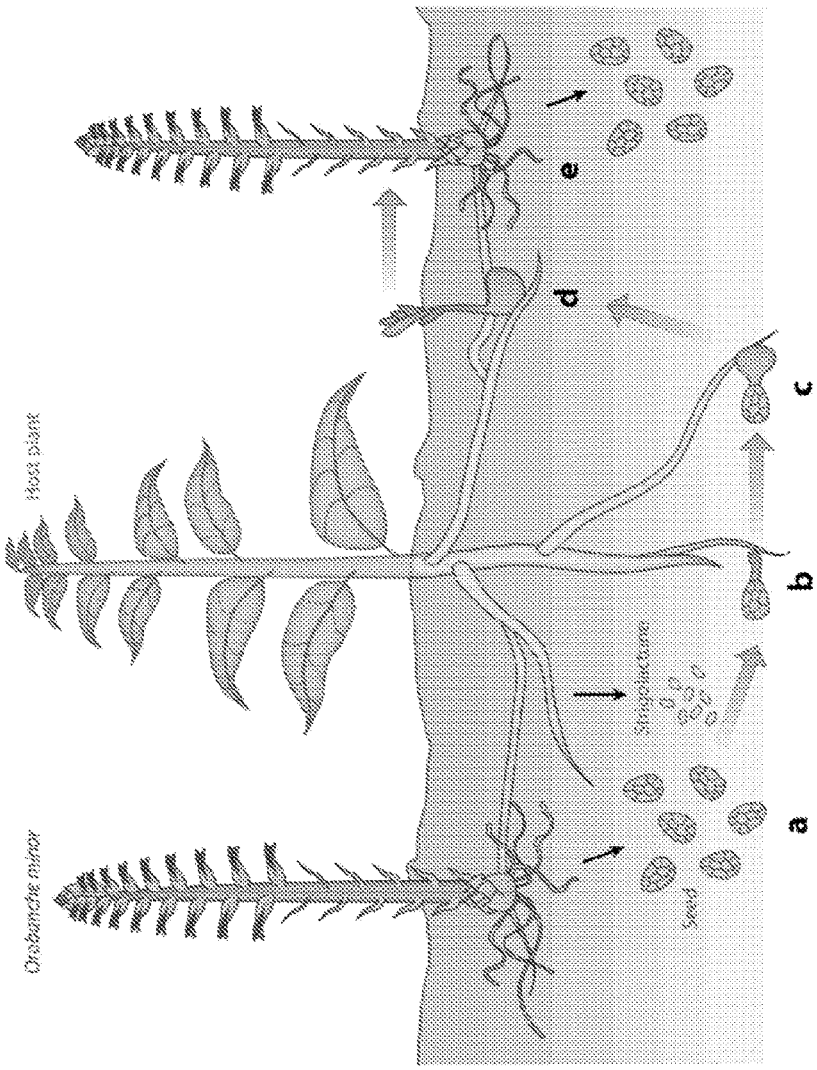

Figure 16: Life cycle of roots parasitic plants. (*a*) Host-derived germination stimulants, such as strigolactones, are required to induce seed germination. (*b*) Seedlings develop haustoria that attach to host roots. (*c–d*) Seedlings grow then for several weeks before appearing above the soil. (*e*) The parasite produces a large number of seeds, which remain viable for many years in soil. (Figure from Xie, *et al.*, 2010; Legend modified).

Figure 17.

Figure 17 Strigolactone Biosynthesis:

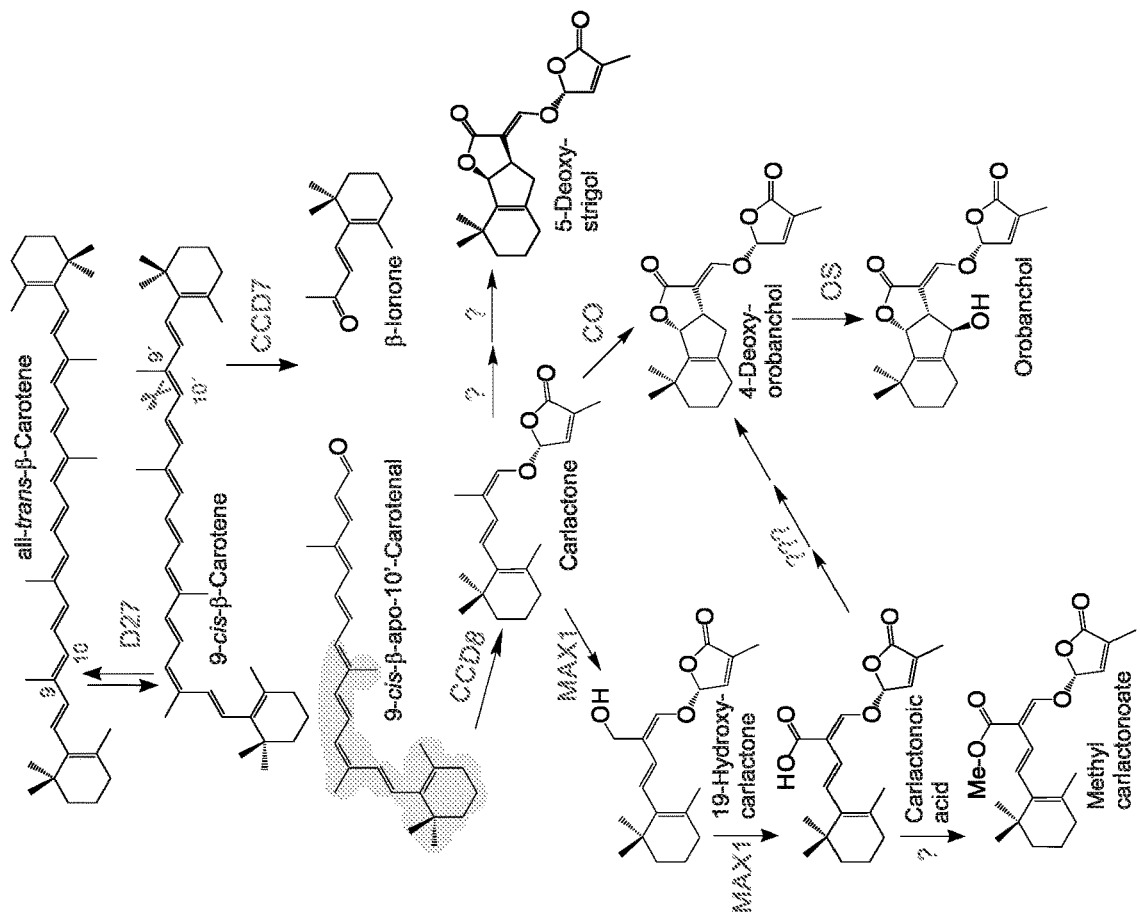

The enzyme DWARF27 (D27) catalyzes the 9-*cis*/all-*trans* isomerization of β-carotene, yielding 9-*cis*-β-carotene that is cleaved by CCD7 at the C9'-C10' double bond in the *trans*-moiety of the substrate, into the intermediate 9-*cis*-β-apo-10'-carotenal and β-ionone.

CCD8 converts, in one step, 9-*cis*-β-apo-10'-carotenal into carlactone and an unidentified second product. Carlactone is thought to derive from the shaded part of the precursor.

The rice carlactone oxidase (CO) Os900, a CYP (711 clade) converts carlactone, by repeated oxygenation and ring closures, into 4-deoxyorobanchol (known as: *ent-2'- epi*-5-deoxystrigol), the parent molecule of the orobanchol-like SLs.

A further CYP of the 711 clade, the rice MAX1 homolog orobanchol synthase, introduces a hydroxyl group at the C-4 position in 4-deoxyorobanchol, forming orobanchol.

The Arabidopsis MAX1 converts carlactone into carlactonoic acid via the intermediate 19-hydroxy carlactone. Carlactonoic acid can be converted into methyl carlactonoate. It is also supposed that carlactonoic acid is a further precursor of 4-deoxyorobanchol in rice.

5-Deoxystrigol, the parent of the strigol-like SLs (see also Figure 2) is likely produced from carlactone by yet unidentified CYP450.

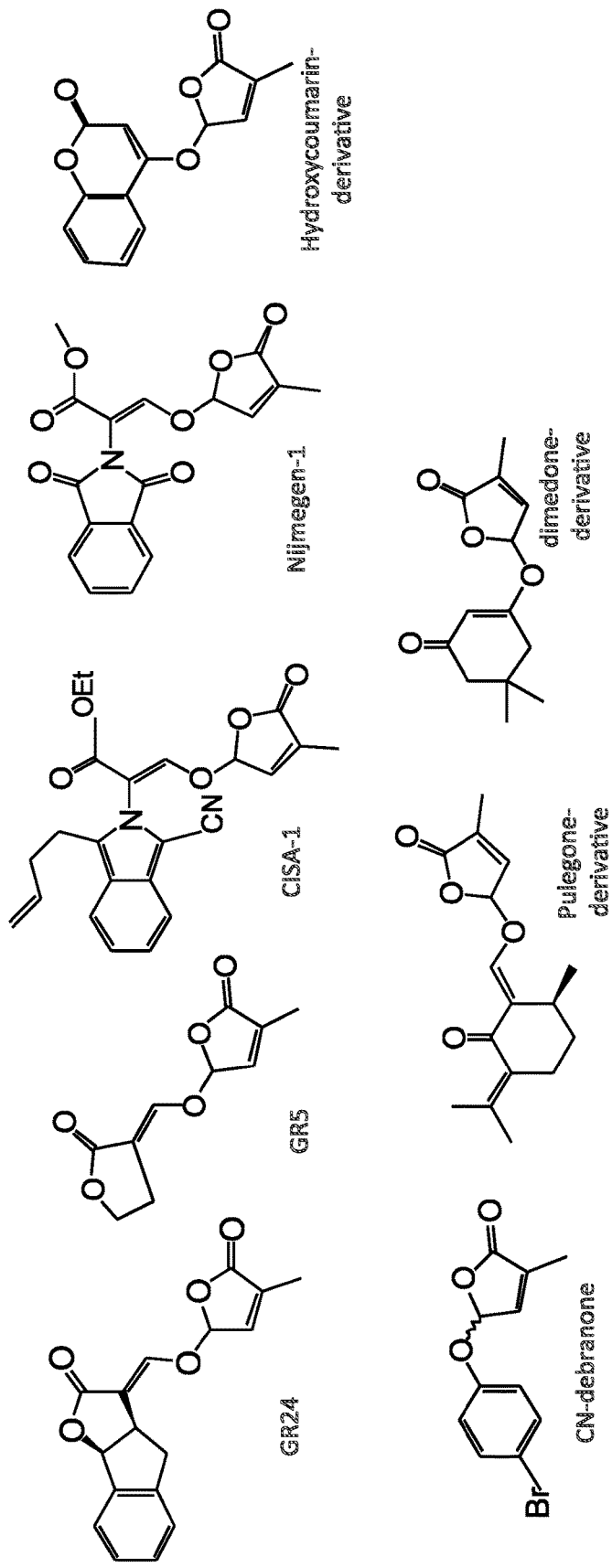
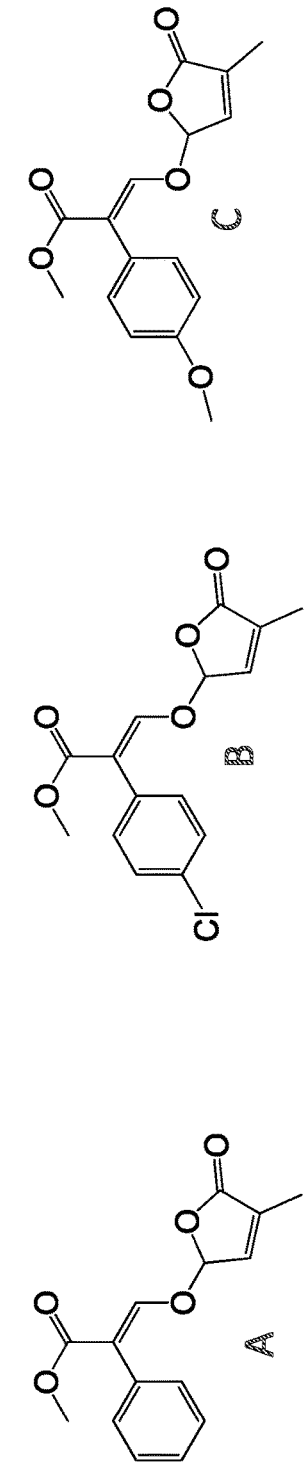
Figure 18. Examples of synthetic strigolactone analogues.

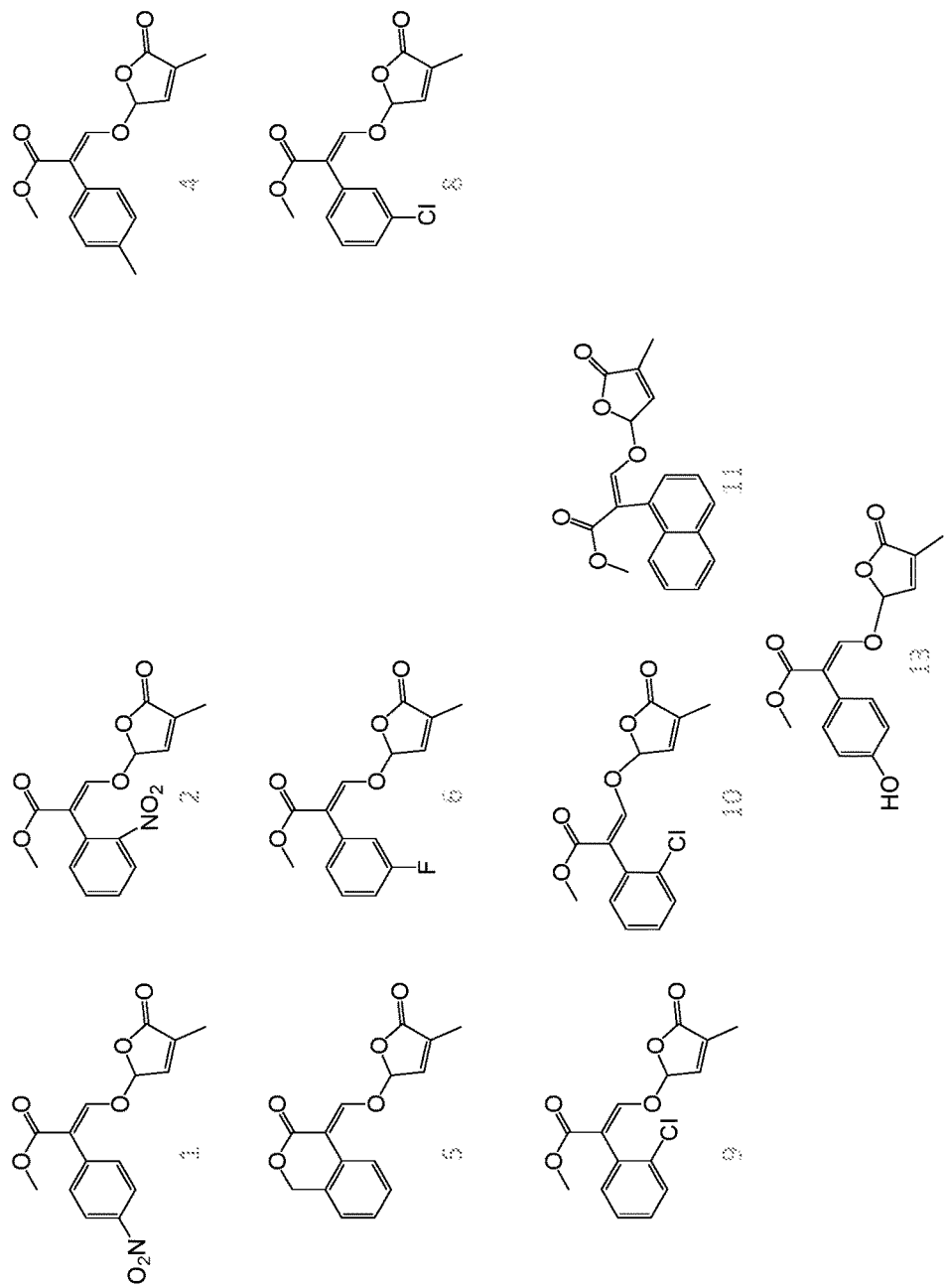
Figure 19. Examples of 10 strigolactone analogs (methyl-phenlactonoates). These compounds have been tested.

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1
cgggatccat gagctcaatt ggattagccc                                    30

<210> SEQ ID NO 2
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 2
ccgctcgagt cagtgatccg tgatgtcctg                                    30

<210> SEQ ID NO 3
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 3
tcaggaacaa tgtgaggcaa gag                                           23

<210> SEQ ID NO 4
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 4
cgcggtttcg gcattctttc tg                                            22

<210> SEQ ID NO 5
<211> LENGTH: 23

```
<212> TYPE: DNA
<213> ORGANISM: Artificial Sequence
<220> FEATURE:
<223> OTHER INFORMATION: Synthetic Sequence

<400> SEQUENCE: 5
tgatgggaag catggtgtta gtg                                         23

<210> SEQ ID NO 6
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 6
cactttggag accattcgat tcc                                         23

<210> SEQ ID NO 7
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 7
gcccaagaag aagatcaaga ac                                          22

<210> SEQ ID NO 8
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 8
agataacaac ggaagcataa aagtc                                       25
```

STRIGOLACTONE ANALOGS AND THEIR USAGE IN PLANT CONTROL

CROSS REFERENCE TO RELATED APPLICATIONS

This application is a National Phase application under 35 U.S.C. 371 of PCT/IB2017/055877 filed Sep. 27, 2017, which claims the benefit of and priority to U.S. Provisional Application No. 62/400,506, filed on Sep. 27, 2016, the disclosures of which are incorporated herein by reference in their entirety.

REFERENCE TO SEQUENCE LISTING

The Sequence Listing submitted on Jun. 12, 2019, as a text file named "KAUST_2016_030_03_ST25.txt" created on May 29, 2019, and having a size of 1,952 bytes is hereby incorporated by reference pursuant to 37 C.F.R. § 1.52(e)(5).

BACKGROUND

Strigolactones (SLs) are an important class of compounds particularly with respect to agriculture. SL compounds are carotenoid-derived compounds and can be isolated from nature. Alternatively, they can be synthesized in the laboratory. SL analogs are compounds which are similar or related in structure to the SL and may have one or more benefits associated with SLs. For example, U.S. Pat. No. 8,980,795 describes a class of SL analogs. This patent describes the basic SL structure in its FIG. 1, illustrating the four rings (A, B, C, and D rings) which are a common feature. The A, B, and C rings are fused and form one side of the molecule and they are linked to the D ring on the other side of the molecule by an intermediate enol ether bridge. The enol ether bridge can be susceptible to nucleophilic attack and hydrolysis, leading to instability in aqueous systems. Also, the enone structural element associated with ring C also can have a detrimental influence on the stability.

U.S. Pat. No. 8,980,795 describes SL analogs such as GR24, GR7, and GR5 compounds in which the core SL common structure has been modified. For example, in GR24, the A ring is converted to an aromatic ring. In GR7, the A ring is eliminated, and in GR5, the A and B rings are eliminated. However, the core enol ether bridge and enone structures are retained in these three SL analogs. U.S. Pat. No. 8,980,795 describes novel SL analogs which are free of the enone element in ring C. These novel SL analogs are based on Formula 1 which is reproduced below and includes elements $R_a$—$R_f$.

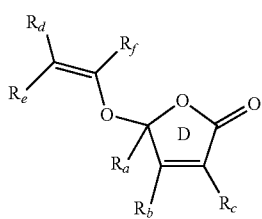

(I)

US Patent Publications 2015/0274690 and 2015/0141255 also describe SL compounds and SL analogs.

More detailed introductory material is provided. A listing of cited references is provided hereinafter. No admission is made that any cited reference herein is prior art.

More particularly, Strigolactones (SLs) are secondary metabolites originally identified as root-derived chemical signals inducing seed germination in root parasitic plants of the Orobanchaceae family (Xie et al., 2010). Later, SLs were also shown to induce hyphal branching in arbuscular mycorrhizal (AM) fungi, which is required for establishing beneficial AM symbiosis (Akiyama et al., 2005). In the meanwhile, SLs are recognized as a novel class of plant hormones that determine different developmental processes, such as establishing shoot and root architecture, regulation of secondary growth and inducing senescence (Beveridge, 2014; Gomez-Roldan et al., 2008; Ruyter-Spira et al., 2013; Umehara et al., 2008). In addition, SLs are involved in pathogen defense and act as positive regulators of abiotic stress responses (Decker et al., 2017; Ha et al., 2014; Torres-Vera et al., 2014).

Natural SLs are carotenoid derivatives consisting of a lactone ring (D-ring) that is connected by an enol ether bridge (in R-configuration) to a structurally variable second moiety (Al-Babili and Bouwmeester, 2015). Canonical SLs, such as strigol and orobanchol, contain a tricyclic lactone (ABC-ring) as a second moiety and are divided, depending on stereochemistry of the B/C-junction, into strigol-(β-orientation, up) and orobanchol-like (α-orientation, down) SLs (Ueno et al., 2011; Xie et al., 2013). Besides the stereochemistry of B/C-junction, various modifications of ABC-ring, such as hydroxylation at different positions, lead to the diversity of canonical SLs. Noncanonical SLs, such as methyl carlactonoate (Abe et al., 2014), heliolactone (Ueno et al., 2014) or zealactone (Charnikhova et al. 2017), do not have an ABC-lactone as a second moiety. The question whether and how structural diversity leads to functional specificity of the around 20 known natural SLs is largely elusive.

The availability of SL biosynthesis and perception mutants has enabled the elucidation of key steps in SL biosynthesis and perception (Al-Babili and Bouwmeester, 2015; Lumba et al., 2017; Waters M. T. et al., 2017). SL biosynthesis starts in plastids with the reversible cis/trans-isomerization of the precursor all trans-β-carotene into 9-cis-β-carotene (Alder et al., 2012; Bruno and Al-Babili, 2016). In next step, the stereospecific carotenoid cleavage dioxygenase 7 (CCD7) cleaves 9-cis-β-carotene into the intermediate 9-cis-β-apo-10'-carotenal and β-ionone (Alder et al., 2012; Bruno et al., 2014). Another CCD, the CCD8, converts 9-cis-β-apo-10'-carotenal via a combination of repeated dioxygenation and intra-molecular rearrangements into carlactone (Alder et al., 2012; Bruno et al., 2017). Carlactone is a central metabolite of SL biosynthesis (Alder et al., 2012; Seto 113 et al., 2014) and is the substrate for cytochrome P450 enzymes of the clade 711, MAX1 in *Arabidopsis* (Booker et al., 2005), which catalyze the formation of canonical, such as 4-deoxyorobanchol, and non-canonical SLs, such as carlactonoic acid (Abe et al., 2014; Zhang et al., 2014). In *Arabidopsis thaliana*, carlactonoic acid is methylated by an unidentified methyltransferase into methyl carlactonoate (Abe et al., 2014). In the next step, methyl carlactonoate is hydroxylated by LATERAL BRANCHING OXIDOREDUCTASE (LBO) into an unidentified product that may be the final product in *Arabidopsis* SL biosynthesis (Brewer et al., 2016). The rice MAX1 homolog carlactone oxidase catalyses the conversion of carlactone into 4-deoxyorobanchol (ent-2'-epi-5-deoxystrigol), the precursor of canonical, orobanchol-like SLs. Orobanchol itself is produced by another rice MAX1 homolog, the orobanchol synthase (Al-Babili and Bouwmeester, 2015; Zhang et al., 2014).

Strigolactone perception and downstream signaling involve the α/β-fold hydrolase DWARF14 (D14) (de Saint Germain et al., 2016; Hamiaux et al., 2012; Yao et al., 2016), which acts as a non-canonical receptor that covalently binds D-ring of SLs after their hydrolysis. In addition, SLs signaling requires leucine-rich-repeat F-box protein MORE AXILLARY GROWTH 2 (MAX2)/DWARF3 (D3) (Stirnberg et al., 2007), a subunit of a SKP1-CUL1-F-box-protein (SCF)-type ubiquitin ligase complex, that targets repressors of SL signalling, such as Arabidopsis SUPPRESSOR OF MORE AXILLARY GROWTH2-LIKE 6,7,8 (SMXL6,7,8) or rice DWARF53 (D53), for proteasome-mediated degradation (Jiang et al., 2014; Zhou et al., 2013). The F-box protein MAX2 is also required for signal transduction of karrikins, smoke-derived compounds that likely mimic an unidentified, internal signaling molecule(s) and which inhibit hypocotyl growth and induce seed germination in various plant species but not in root parasitic weeds (Nelson et al., 2012). Karrikins share structural similarities (D ring) with SLs and bind to the D14 paralog KARRIKIN INSENSITIVE 2 (KAI2), likely leading to proteasomal degradation of presumed suppressors (Waters et al., 2017). Karrikin response is also triggered by 2'S-configured stereoisomer of common SL analog GR24 that is usually applied as a racemic mixture of 2'S and 2'R isomers. The genome of root parasitic plant Striga hermonthica encodes 11 D14/KAI2 homologs. It was recently shown that Striga KAI2 paralogs, especially ShHTL7, which constitute a distinct clade, are responsible for perception of host-released SLs and thus for triggering parasitic weed seed germination (Conn et al., 2015; Tsuchiya et al., 2015).

Several parasitic Striga and Phelipanche species of the Orobanchaceae family are of great importance for agriculture. The Striga species S. asiatica and S. hermonthica infect cereals, including maize, sorghum, pearl millet, and rice, while Phelipanche species affect crops such as sunflower, tomato and legumes (Parker, 2009). These root parasitic weeds are the reason for enormous yield losses in Africa, the Mediterranean and large parts of Asia (Parker, 2009). In particular, S. hermonthica is considered as one of the seven most severe biotic threats to food security, affecting subsistence and livelihood of 100 million people in sub-Saharan Africa (Pennisi, 2010). S. hermonthica has been observed in 32 countries (Rodenburg et al., 2017) infesting estimated 50 million hectares of arable land in Sahel and Savannah zones in Africa, causing annual losses of around 7 billion US$ (Ejeta, 2007; Parker, 2009, 2012). Severe soil infestation with enormous numbers of long-lived and tiny Striga seeds, and germination dependency of these seeds on host derived signaling molecules has made control of this weed very difficult (Delavault et al., 2016; Ejeta, 2007; Joel, 2000).

During the evolution of parasitism, root parasitic plants have either totally lost or significantly reduced their capability for photosynthesis and, hence, cannot survive without a host plant that provides them with metabolites, water and minerals (Xie et al., 2010). In this parasite-host relationship, SLs are chemical signals required for the germination of parasite seeds, ensuring availability of an appropriate host (Ruyter-Spira et al., 2013). Such dependency on germination cues may provide opportunities for parasitic weed control. Induction of parasitic weed seed germination by exogenous application of germination stimuli before sowing crop seeds could, for instance, lead to the death of emerging parasite seedling (suicidal germination). This could be a promising approach to reduce weed seed bank in soil. For this purpose, natural SLs are, however, not suitable candidates since they cannot be obtained from natural sources in sufficient quantities or at reasonable costs (Reizelman et al., 2000). Moreover, organic synthesis of natural SLs is challenging, due to their complex structures that also contain several chiral centers (Kgosi et al., 2012; Zwanenburg and Pospisil, 2013; Zwanenburg et al., 2016). Hence, a prerequisite for implementing suicidal germination approach outlined above is the availability of SLs or analogs/mimics that are easy to synthesize and which efficiently induce Striga seed germination. SLs analogs could also be used in agriculture and horticulture, for instance, to direct water and other resources in one major branch by suppressing branching or tillering, to induce secondary growth, to enhance abiotic stress tolerance, or to modulate root architecture, by increasing primary root length (Agusti et al., 2011; Ha et al., 2014). SLs also accelerate senescence (Yamada et al., 2014), a functionality that might be exploited for the development of a new suite of herbicides.

Recently, a carlactone-based SL analog, nitro-phenlactone, was reported that exerts SLs activities, but with different efficiencies, indicating the possibility of establishing SLs analogs with specific functions (Jia et al., 2016).

Briefly, strigolactones (SLs) are a new class of phytohormones that also act as germination stimulants for root parasitic plants, such as Striga spp., and as branching factors for symbiotic arbuscular mycorrhizal fungi. However, sources for natural SLs are very limited. Hence, efficient and simple SL analogs are needed for elucidating SL-related biological processes as well as for agricultural applications.

A need yet exists to develop improved SL compounds, SL compositions, and methods of uses of same, particularly with respect to plant growth regulation and to weed control.

SUMMARY

Aspects and embodiments described herein include, for example, compounds, compositions, as well as methods of making and using the compounds and compositions.

In a first aspect, a composition is provided comprising at least one compound which is represented by formula II:

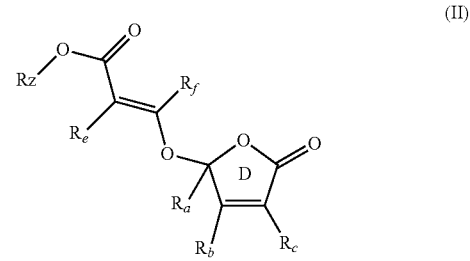

wherein Re is an optionally substituted C6-C24 aryl group or an optionally substituted C6-C24 alkylaryl group, and wherein Rz is hydrogen, a monovalent optionally substituted C12 alkyl group, or a bivalent optionally substituted C1-C12 alkylene group which bonds to the optionally substituted C6-C24 aryl group or the optionally substituted C6-C24 alkylaryl group of the Re moiety forming a ring; and wherein $R_a$, $R_b$ and $R_c$, independently from each other, represent:
(a) a hydrogen atom, a halogen atom, a nitro group, a cyano group, a formyloxy group, a formylamino group or a carbamate group,
(b) a substituent $R_1$, wherein $R_1$ represents C1-C8-alkyl, C2-C8 alkenyl, C2-C8-alkynyl, C3-C8-cycloalkyl, or C1-C8-alkoxy, in each of which the hydrogen atoms may be partly replaced by other groups or atoms,
(c) a substituent —OR$_2$, wherein R$_2$ represents a hydrogen atom, C1-C8-alkyl, C2-C8-alkenyl, C2-C8-alkynyl, C1-C8-alkylcarbonyl, C1-C8-alkylaminocarbonyl or C1-C8-alkoxycarbonyl, in each of which the hydrogen atoms may be partly replaced by other groups or atoms,
(d) a substituent —NR$_3$R$_4$, wherein R$_3$ and R$_4$, independently from each other, represent a hydrogen atom, C1-C8 alkyl, C1-C8-alkylcarbonyl, C1-C8-halogenoalkylcarbonyl, phenyl or benzyl, in each of which the hydrogen atoms may be partly replaced by other groups or atoms,
(e) a substituent —(O)—R$_5$, wherein R$_5$ represents a hydrogen atom, C1-C8-alkyl or C1-C8-alkyloxy, in each of which the hydrogen atoms may be partly replaced by other groups or atoms, —NH$_2$, NHR$_5$ or NR$_5$R$_5$ (where the two substituents R$_5$ may be the same or different), —NR$_5$(OH),
(f) a substituent —S(O)$_n$—R$_6$, wherein n is 0, 1 or 2 and R$_6$ represents C1-C8-alkyl in which the hydrogen atoms may be partly replaced by other groups or atoms, —NH$_2$, —NHR$_6$ or NR$_6$R$_6$ (where the two substituents R$_6$ may be the same or different), or
(g) a 4-, 5-, 6- or 7-membered heterocyclic ring comprising up to 4 heteroatoms selected from nitrogen, oxygen or sulfur, where in each of these rings the hydrogen atoms may be partly replaced by other groups or atoms, and
R$_f$ represents a hydrogen atom, a halogen atom, a nitro group, a cyano group or C1-C8-alkyl-, C2-C8 alkenyl, C2-C8-alkynyl, or C3-C8-cycloalkyl,
wherein, for the compound represented by formula (II), the following five embodiments are excluded:

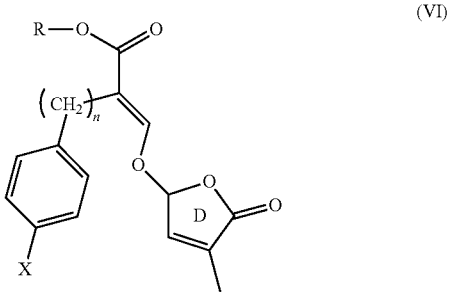

wherein for Formula VI (i) R is methyl, X is H and n=0; (ii) R is methyl, X is H, and n=1; (iii) R is methyl, X is H, and n=2; (iv) R is methyl, X is Cl, and n=0; and (v) R is methyl, X is —OCH$_3$ and n=0.

In one embodiment, Re of Formula II is represented by Formula III:

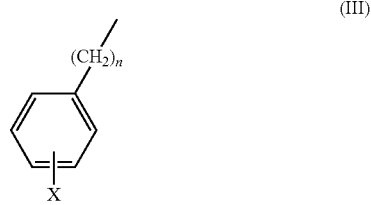

wherein X in Formula III is a monovalent group which is ortho, meta, or para-substituted, and n is 0, 1, or 2.

In one embodiment, the compound of Formula II is represented by Formula (IV):

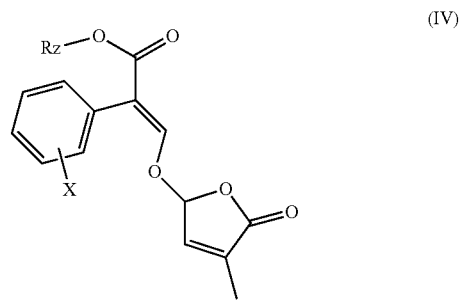

wherein Rz is for example, H or a monovalent optionally substituted C1-C12 alkyl group, and X in Formula IV is a monovalent group in the ortho, meta, or para position.

For any composition described and/or claimed herein, for the compound represented by formula (II), the following five embodiments can be excluded:

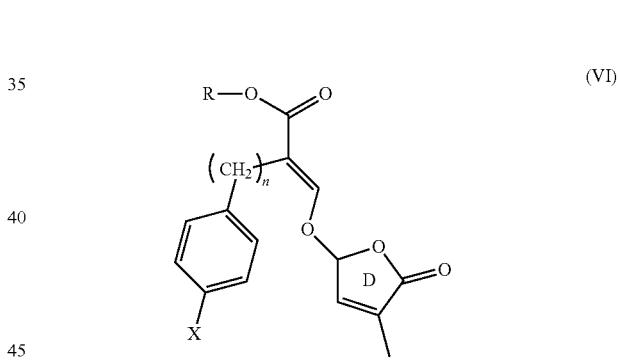

wherein for Formula VI (i) R is methyl, X is H and n=0; (ii) R is methyl, X is H, and n=1; (iii) R is methyl, X is H, and n=2; (iv) R is methyl, X is Cl, and n=0; and (v) R is methyl, X is —OCH$_3$ and n=0.

Another embodiment is for a method comprising applying a composition according to compositions described and/or claimed herein for the control of a target plant growth.

In one embodiment, the control of target plant growth is to encourage the target plant growth. In another embodiment, the control of target plant growth is to discourage the target plant growth. In another embodiment, the control of target parasitic plant growth is for controlling the germination of parasitic root plants.

Another aspect is for methods of applying a composition for the control of a target plant growth, wherein the composition comprises at least one compound which is represented by Formula II:

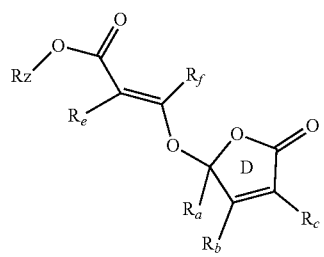

(II)

wherein Re is an optionally substituted C6-C24 aryl group or an optionally substituted C6-C24 alkylaryl group, and wherein Rz is a monovalent optionally substituted C1-C12 alkyl group or a bivalent optionally substituted C1-C12 alkylene group which bonds to the optionally substituted C6-C24 aryl group or the optionally substituted C6-C24 alkylaryl group of the Re moiety forming a ring; and wherein $R_a$, $R_b$ and $R_c$, independently from each other, represent:

(a) a hydrogen atom, a halogen atom, a nitro group, a cyano group, a formyloxy group, a formylamino group or a carbamate group, (b) a substituent $R_1$, wherein $R_1$ represents C1-C8-alkyl, C2-C8 alkenyl, C2-C8-alkynyl, C3-C8-cycloalkyl, or C1-C8-alkoxy, in each of which the hydrogen atoms may be partly replaced by other groups or atoms, (c) a substituent —$OR_2$, wherein $R_2$ represents a hydrogen atom, C1-C8-alkyl, C2-C8-alkenyl, C2-C8-alkynyl, C1-C8-alkylcarbonyl, C1-C8-alkylaminocarbonyl or C1-C8-alkoxycarbonyl, in each of which the hydrogen atoms may be partly replaced by other groups or atoms, (d) a substituent —$NR_3R_4$, wherein $R_3$ and $R_4$, independently from each other, represent a hydrogen atom, C1-C8 alkyl, C1-C8-alkylcarbonyl, C1-C8-halogenoalkylcarbonyl, phenyl or benzyl, in each of which the hydrogen atoms may be partly replaced by other groups or atoms, (e) a substituent —(O)—$R_5$, wherein $R_5$ represents a hydrogen atom, C1-C8-alkyl or C1-C8-alkyloxy, in each of which the hydrogen atoms may be partly replaced by other groups or atoms, —$NH_2$, $NHR_5$ or $NR_5R_5$ (where the two substituents $R_5$ may be the same or different), —$NR_5(OH)$, (f) a substituent —$S(O)_n$—$R_6$, wherein n is 0, 1 or 2 and $R_6$ represents C1-C8-alkyl in which the hydrogen atoms may be partly replaced by other groups or atoms, —$NH_2$, —$NHR_6$ or $NR_6R_6$ (where the two substituents $R_6$ may be the same or different), or (g) a 4-, 5-, 6- or 7-membered heterocyclic ring comprising up to 4 heteroatoms selected from nitrogen, oxygen or sulfur, where in each of these rings the hydrogen atoms may be partly replaced by other groups or atoms, and $R_f$ represents a hydrogen atom, a halogen atom, a nitro group, a cyano group or C1-C8-alkyl-, C2-C8 alkenyl, C2-C8-alkynyl, or C3-C8-cycloalkyl.

In one embodiment, for the compound represented by formula (II), the following five embodiments are excluded:

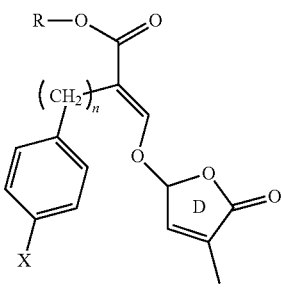

(VI)

wherein for Formula VI (i) R is methyl, X is H and n=0; (ii) R is methyl, X is H, and n=1; (iii) R is methyl, X is H, and n=2; (iv) R is methyl, X is Cl, and n=0; and (v) R is methyl, X is —$OCH_3$ and n=0.

In one embodiment, the control of target plant growth is to encourage the target plant growth. In one embodiment, the control of target plant growth does not include (excludes) controlling the germination of parasitic root plants. In one embodiment, the control of target plant growth is for controlling the germination of parasitic root plants.

Generally, the compounds can compositions can be applied and used in agricultural applications. One example is as a germination stimulant for root parasitic plants. Another example is as a branching factor. Another example is plant architecture including root architecture. Another example is triggering leaf senescence. Another example is inhibiting rice tillering. Additional examples of methods of application and use are described hereinafter including the working examples.

In a nutshell, a new series of SLs analogs, Methyl-Phenlactonoates (MPs), are described which in preferred embodiments can be easily synthesized and which resemble the non-canonical SL methyl carlactonoate. Aiming at the identification of analogs that can be applied as suicidal germination agents and growth regulators or used in basic and applied research to determine particular SL activities, the stability of MPs was measured and their activities in exerting different SLs functions is described, as well as their affinity to SL receptors.

Based on the structure of the noncanonical SL methyl carlactonoate, a new, easy to synthesize series of analogs, termed "Methyl Phenlactonoates (MPs)" were developed, and preferred embodiments developed. Their efficacy in exerting different SL functions was evaluated and their affinity to SL receptors from rice and *Striga hermonthica* was determined. Briefly, many of the MPs showed considerable activity in regulating plant's architecture, triggering leaf senescence and inducing parasitic seed germination. Moreover, some MPs outperformed GR24, a widely used SL analog with a complex structure, in exerting particular SL functions, such as modulating *Arabidopsis* roots architecture or inhibiting rice tillering. Thus, MPs will help in elucidating SLs functions and are promising candidates for agricultural applications. Moreover, MPs demonstrate that slight structural modifications can impact the efficiency in exerting particular SL functions, indicating that structural diversity of natural SLs may mirror a functional specificity.

In sum, a variety of advantage or advantages can be found for one or more embodiments described herein. For example, in general, good control of plant growth can be achieved, whether these plants are useful or desirable plants (e.g., those providing food or decoration) or undesirable plants (e.g., those classified as weeds). For example, for some embodiments, good plant growth regulation is achieved, and the compounds are demonstrated as useful for regulating plant architecture. Also, for example, for some embodiments, good weed control is achieved. In particular, good activity in inducing the germination of *Striga harmonthica* seeds is shown. The compounds in some cases are relatively easy to prepare. One or more other advantages for one or more embodiments can be found expressly or inherently in the various embodiments described herein.

BRIEF DESCRIPTION OF THE FIGURES

FIG. 10. *Striga hermonthica* seed germination in response to MPs treatment. (A) Each MP was applied in 50 µl volume (1.0 µM) on a disc containing 50-100 preconditioned *Striga* seeds. H$_2$O and GR24 are included as negative and positive control, respectively. (B) *P. ramosa* seed germination in response to MPs application. 50 µl of each MP was applied (1.0 µM) on a disc containing 50-100 preconditioned *P. ramosa* seeds. Bars represented means±SE (n=3). (C) Picture showing *S. hermonthica* seed germination bioassay.

FIG. 14. Developmental functions of SLs. SLs (a) regulate the growth of internodes, (b) accelerate leaf senescence, (c) lead to elongation of root hairs and trigger the growth of primary roots, (d) enhance stem thickness and induce secondary growth, (e) reduce the number of shoot branches, and inhibit the formation of (f) adventitious and (g) lateral roots.

FIG. 15. Structures of Strigolactones. C-atom numbering and the characteristic ABC-D-ring are shown in the structure of 5-deoxystrigol. Examples of strigol-like strigolactones with the C-ring in 13 orientation (left column) and orobanchol-like with the C-ring in an alpha orientation (middle column). Carlactone and derivatives of are depicted in the right column.

FIG. 16. Life cycle of roots parasitic plants. (a) Host-derived germination stimulants, such as strigolactones, are required to induce seed germination. (b) Seedlings develop haustoria that attach to host roots. (c-d) Seedlings grow then for several weeks before appearing above the soil. (e) The parasite produces a large number of seeds, which remain viable for many years in soil.

FIG. 17. The enzyme DWARF27 (D27) catalyzes the 9-cis/all-trans isomerization of β-carotene, yielding 9-cis-β-carotene that is cleaved by CCD7 at the C9'-C10' double bond in the trans-moiety of the substrate, into the intermediate 9-cis-β-apo-10'-carotenal and β-ionone. CCD8 converts, in one step, 9-cis-β-apo-10'-carotenal into carlactone and an unidentified second product. Carlactone is thought to derive from the shaded part of the precursor. The rice carlactone oxidase (CO) Os900, a CYP (711 clade) converts carlactone, by repeated oxygenation and ring closures, into 4-deoxyorobanchol (known as: ent-2'-epi-5-deoxystrigol), the parent molecule of the orobanchol-like SLs. A further CYP of the 711 clade, the rice MAX1 homolog orobanchol synthase, introduces a hydroxyl group at the C-4 position in 4-deoxyorobanchol, forming orobanchol. The *Arabidopsis* MAX1 converts carlactone into carlactonoic acid via the intermediate 19-hydroxy carlactone. Carlactonoic acid can be converted into methyl carlactonoate. It is also supposed that carlactonoic acid is a further precursor of 4-deoxyorobanchol in rice. 5-Deoxystrigol, the parent of the strigol-like SLs is likely produced from carlactone by yet unidentified CYP450.

FIG. 18. Examples of synthetic strigolactone analogues.

FIG. 19. Examples of 10 strigolactone analogs (methylphenlactonoates) as shown in FIG. 1A but excluding MP3, MP7, MP12, and MP14.

DETAILED DESCRIPTION

Introduction

Figure 1:
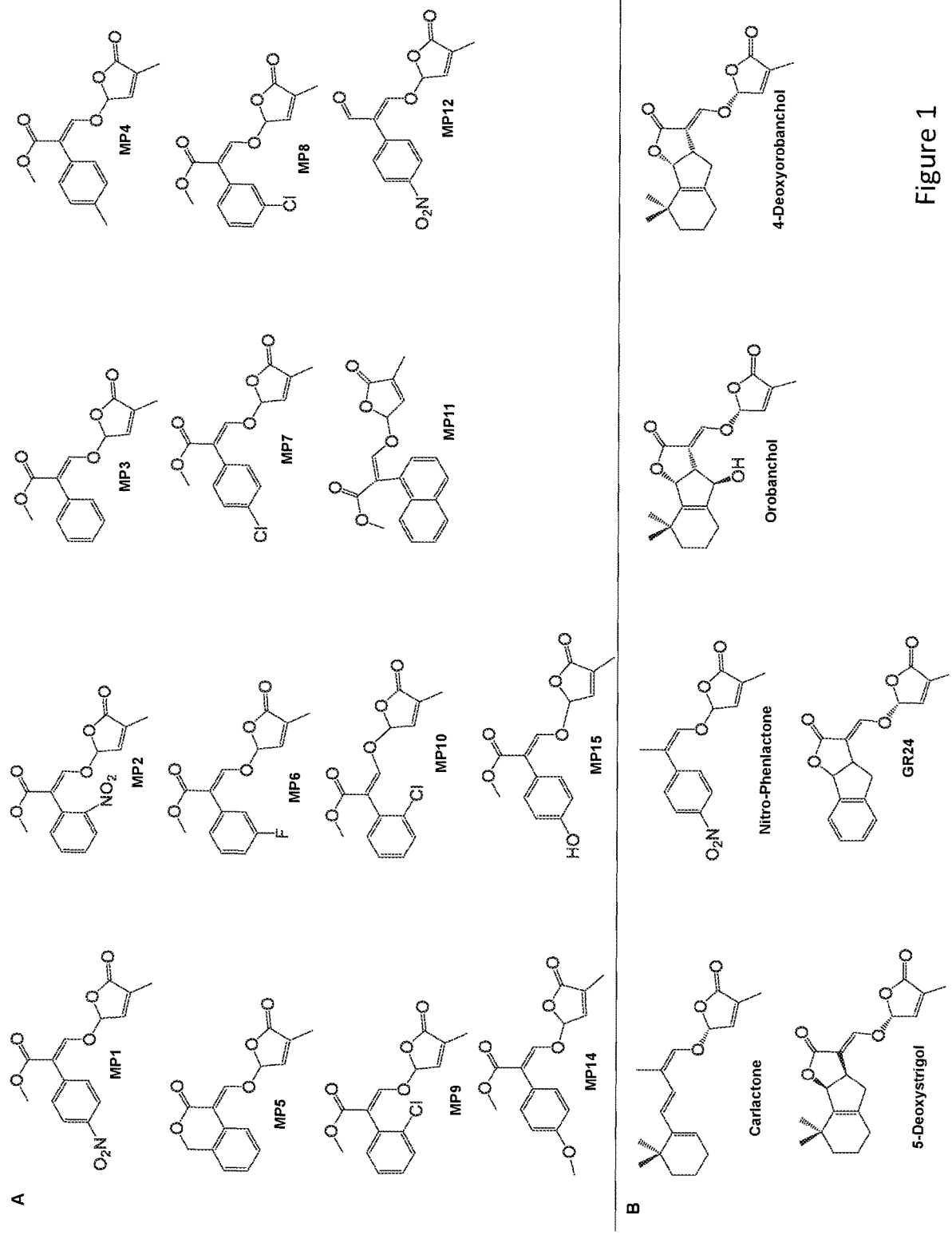
FIG. 1. (A) Structure of methyl-phenlactonoates (MPs). MP12 is comparative. (B) Structure of Carlactone, Nitrophenlactone, Orobanchol, 4-Deoxyorobanchol, 5-Deoxystrigol and the standard strigolactone analog GR24.

The entire disclosure of priority U.S. provisional application Ser. No. 62/400,506 filed Sep. 27, 2016 is hereby incorporated by reference in its entirety for all purposes, including written description, working examples, Figures, cited references, and claims.

Additional detailed description about SLs and SL analogs is provided in the following description.

References cited herein are incorporated by reference in their entirety. No admission is made that any reference is prior art.

Strigolactones (SLs) are carotenoid-derivatives that were originally identified in roots exudates, due to their capability in inducing seed germination of roots parasitic weeds of the genus *Striga* (Xie et al., 2010). Later on, they were shown to be involved in establishing the beneficial mycorrhizal symbiosis, by triggering the hyphal branching of mycorrhizal fungi (Akiyama et al., 2005). Shoot-branching mutants in *Arabidopsis*, rice, pea and *petunia* have then paved the way for the discovery of the general of SLs as plant hormone that regulates many aspects of plant development, including shoot branching/tiller number, plant height, stem thickness, root growth and architecture (all types of roots), and leaf senescence (FIG. 14, for review, see Al-Babili et al., 2015; Beveridge, 2014; Gomez-Rolden et al., 2008; Lopez-Obando et al., 2015; Morffy et al., 2016; and Ruyter-Spira et al., 2013). In addition to these developmental functions, SLs are supposed to positively contribute to abiotic stress tolerance (salt and drought stress) (Ha et al., 2014) and to the colonization by rhizobial bacteria (Foo et al., 2011). SLs modulate also the growth of pathogenic fungi (Dor et al., 2011), and in composition with oligosaccharides, SLs can be used to protect plants from pathogenic fungi and to increase their yield (see, for example, WO 2010125065 A3, "Compositions comprising a strigolactone compound and a chito-oligosaccharide compound for enhanced plant growth and yield").

A recent definition of SLs (structures are depicted in FIG. 15) describes them as carotenoid-derived compounds that consist of two moieties: a highly conserved butenolide ring that is linked by enol ether bridge to a second, variable structure (Al-Babili, et al., 2015). Following this definition, SLs can be divided into (a) the tricyclic lactone (ABC ring)-containing, strigol- and orobanchol-like compounds, and (b) SLs without tricyclic lactone, such as carlactonoate that only contains a β-ionone ring (corresponding to the A-ring) instead (FIG. 15). The strigol- and orobanchol-like SLs are distinguished by the stereochemistry of the BC-ring junction (Al-Babili, et al., 2015). The C ring of the strigol-like SLs, likely derived from 5-deoxystrigol, is in the β orientation (up), while that of orobanchol-like SLs, which originate from 4-deoxyorobanchol (known as ent-2'-epi-5-deoxystrigol), is in α orientation (down) (FIG. 14). Derivatizations, such as methylation, hydroxylation, epoxidation, or ketolation, of this skeletons lead to the diversity of natural SLs (FIG. 14).

*Striga* spp. of the Orobanchaceae family (Tank, et al., 2006) are root parasitic plants that rely on their host to obtain their needs on water, minerals and photosynthetic products (Hearne et al., 2009). *Striga* seeds persist for many years in the soil and do not germinate unless they detect the presence of a host, including many crops such cereals, tomato, sunflowers, cowpea, and the like, in their direct proximity (Matusova, et al., 2005, Yoneyama et al., 2010, Zwanenburg et al., 2009). In general, these germination signals are SLs (Xie et al., 2010). Emerging *Striga* seedlings develop a physical connection to the host plant, which is called haustorium and which enable them to sap their requirements on water and nutrition water minerals and sugars (for lifecycle of the parasites, see FIG. 16; for review, see Xie et al, 2010). *Striga* parasitism has severe effects on the growth of the host plant and is responsible for enormous yield losses in many parts of the world worldwide (Parker, 2009). Moreover, *Striga* is considered as one of the seven most severe threats to food security. *Striga* infestation can cause total yield losses and crop shortfalls in cereals in the range of $US 7 billion (Parker, 2009).

Root parasitic weeds infect different crops. For instance, *Striga* spp. like *S. asiatica, S. aspera, S. forbesii* and particularly *S. hermonthica* parasitize cereal crops, e.g. sorghum, maize, millet and rice, while *S. gesnerioides* attacks cowpea and other legumes. *Alectra vogelii* is responsible for considerable yield losses of grain legume crops, particularly cowpea, in semiarid areas of sub-Saharan Africa. In the Middle East, India and large parts of Europe and North America, *Orobanche* and *Phelipanche* spp. infect dicotyledonous crops including tomato, tobacco, carrot, clovers, cucumber, sunflower and legumes. In 1991, it was estimated that 16 million hectares in the Mediterranean and West Asia are threatened by *Orobanche* and *Phelipanche* (for review, see Parker, 2009; Xie et al., 2010). The fact that SLs are also important for establishing the mycorrhizal symbiosis with mycorrhizal fungi may explain why plants release SLs, though they are inviting the roots parasites.

SLs, Structure and Biosynthesis

Enzymatic studies combined with mutant analysis has led to the biosynthetic scheme shown in FIG. 17. The pathway starts with reversible isomerization of all-trans- into 9-cis-β-carotene, which is catalyzed by the enzyme DWARF27 and followed by the stereospecific cleavage of 9-cis-β-carotene into a 9-cis-configured intermediate (Alder et al., 2012; Bruno et al., 2014). The latter undergoes repeated oxidation/cleavage and intramolecular rearrangements that lead to carlactone (Alder et al., 2012). This combination of reactions is catalyzed by CCD8 (Alder et al., 2012). In rice, MAX1-homologs, CYP450 enzymes of the 711 clade, convert carlactone into 4-deoxyorobanchol, the supposed parent molecule of the orobanchol-like subfamily of SLs. Orobanchol is formed by a further rice MAX1 homolog (Zhang et al., 2014). The *Arabidopsis* MAX1 oxidizes carlactone into carlactonoate (Abe et al., 2014), which, after methylation, can bind to SLs receptor D14 (see below).

SLs, Mode of Action

It is generally accepted that SLs bind to an a/13 hydrolase (D14 in rice), enabling the interaction with a F-box protein (MAX2 in *Arabidopsis*) that conveys repressor proteins, such as the recently discovered rice D53, to proteasomal degradation. In addition to this transcriptional regulation, it is believed that that SLs inhibition of shoot branching is a result of alterations in polar auxin transport (Al-Babili et al., 2005; Beveridge, 2014; Gomez-Roldan et al., 2008; Ruyter-Spira et al., 2013).

SL Analogues and their Usage

Natural SLs are produced at very low concentrations and are known to be unstable. In some cases, the organic synthesis of such compounds can be difficult. Hence, there is a demand for easy to synthesize and inexpensive SLs analogs. Such compounds can find application in combating roots parasitic weeds, following the so called "suicidal germination" strategy. Suicidal germination refers to the application of seed germination stimulant, such as SLs analogs, in the absence of a host, resulting in germination which is followed by seedlings death and leading to elimination/reduction of seed bank in soil. SLs analogs may be also used to regulate tillering number, alter roots growth, increase wood production and, in composition, as fungicide. SLs analogs have been developed and tested for particular properties (examples are shown in FIG. 18).

Additional introduction is provided. The plant hormones, strigolactones (SLs), were originally isolated from plant root exudates, as stimulants of seed germination in root parasitic plants, such as *Striga* and *Orobanche* species. During the evolution of parasitism, root parasitic plants have either totally lost or significantly reduced their capability for photosynthesis and, hence, cannot survive without a host plant that provides them photosynthates, water and minerals. Root parasitic weeds are one of the most severe global threats for agriculture, causing enormous yield losses in Africa, the Mediterranean and large parts of Asia. The parasitic weeds *Striga* species *S. asiatica* and *S. hermonthica* infect cereals, including maize, sorghum, pearl millet, and rice, while *Orobanche* species affect crops such as sunflower, tomato and legumes. In this parasite-host interplay, SLs act as chemical signals required for the germination of the parasite seeds, coordinating the emergence of the parasite seedlings with the availability of an appropriate host (for life cycle of the parasites, see FIG. 16). The reason why plants release SLs into soil where they invite parasitic infestation was unraveled by the discovery that these compounds induce hyphal branching in arbuscular mycorrhizal (AM) fungi, which is required for building up the beneficial AM symbiosis. AM symbiosis is present in around 80% of land plants species that use a fungal partner to obtain minerals, such as phosphorus. In return, the fungus covers its needs on carbohydrates from the plant host. Studies on pea, *Arabidopsis*, rice and *petunia* mutants that show an increase in the number of shoot branches/tillers led to the discovery of the hormonal function of SLs. These mutants were affected either in the biosynthesis or the perception of a supposed signaling molecule that inhibits the outgrowth of axillary buds. The lack of SLs in the biosynthesis mutants and the capability of the SL analog GR24 in rescuing the high-branching/-tillering phenotype suggested that SLs are the long-sought after hormone inhibiting shoot branching (Matusova, et al., 2005). In addition, SLs are known to be involved in many other processes, including secondary growth, leaf senescence, response to salt stress, and to determine shoot and root architecture according to nutritional conditions. For developmental functions of SLs, see FIG. 14.

Canonical SLs have a typical structure consisting of a tricyclic (ABC-ring) and a monocyclic lactone (D-ring), which are connected by an enol ether bridge with C2' in R configuration (FIG. 15). ABC-ring containing SLs are classified based on the stereochemistry of the B-C junction into the (−)-orobanchol-like SLs that have the C-ring in a orientation and the (+) strigol-like SLs with β orientation of the C-ring. Modifications of the ABC ring in both classes give rise to the diversity of natural SLs. According to a recent definition, SL-related compounds that lack the ABC ring, such as the SL biosynthesis intermediate carlactone and the recently identified carlactonoic acid, can be also considered as SLs. Structures of SLs are depicted in FIG. 15.

The availability of mutants affected in SL biosynthesis paved the way for elucidating major steps in the biosynthesis of these compounds. The pathway starts with the reversible cis/trans-isomerization of all-trans- into 9-cis-β-carotene (Alder et al., 2012), catalyzed by the iron-binding enzyme DWARF27. In the next step, the carotenoid cleavage dioxygenase 7, a member of an ubiquitous family of enzymes that catalyze the oxidative cleavage of carotenoids and which includes enzymes mediating retinal formation and abscisic acid biosynthesis, catalyzes the stereospecific cleavage of 9-cis-β-carotene ($C_{40}$-backbone) into the volatile β-ionone ($C_{13}$) and the $C_{27}$-cis-configured intermediate 9-cis-β-apo-10'-carotenal. The latter is the substrate of CCD8, a further member of the carotenoid oxygenase enzyme family, which catalyzes a yet not understood combination of reactions leading to the intermediate carlactone (FIG. 17). The rice carlactone oxidase, a CYP711 homolog of the *Arabidopsis* MAX1, converts carlactone into 4-deoxyorobanchol (ent-2'-epi-5-deoxystrigol) the supposed precursor of the orobanchol-like group of SLs. A further rice MAX1 homolog, the rice orobanchol synthase, mediates the hydroxylation of 4-deoxyorobanchol, yielding orobanchol. The *Arabidopsis* MAX1 converts carlactone into carlactonoic acid which is methylated by a yet unknown enzyme into methyl-carlactonoic acid (Abe et al., 2014) (see also FIG. 17).

SLs perception involves the α/β-fold hydrolase corresponding to D14 in rice and DAD2 in *petunia*, and the leucine-rich-repeat F-box protein corresponding to MAX2 in *Arabidopsis*. It was shown that the SL analog GR24 binds to DAD2 and that it is targeted by the hydrolytic activity of this receptor. Binding of GR24 enables the interaction of the receptor with the F-box protein and leads to proteasome-mediated degradation of target proteins, such as the recently identified rice D53 that acts as a repressor.

A major part of knowledge on the biological activities of SLs has been obtained by using analogs (examples are presented in FIG. 18), particularly GR24 that shows high structural similarity to canonical SLs. Indeed, GR24 can rescue the phenotype of SL deficient mutants, induces hyphal branching of arbuscular mycorrhizal fungi and triggers seed germination in root parasitic weeds. Other compounds, such as AR36 (Boyer et al., 2014) and 4-Br debranone (4BD) (Fukui et al., 2013), which contain a D-ring connected by an enol ether bridge less complex second moieties, showed moderate activity in inducing seed germination. Another analog, Nijmegen-1, has been developed to induce suicidal germination in roots parasitic weeds, i.e. germination in the absence of a host, and showed very promising results in a trial performed in a tobacco field infested by *Orobanche ramosa*.

Carlactone was originally identified as an in vitro product formed by the sequential action of heterologously expressed D27, CCD7 and CCD8. Carlactone showed considerable activity in inducing seed germination in *S. hermonthica*, although the compound lacks the enone moiety that is present in the C-ring of canonical SLs and which is supposed to be required for inducing the germination activity (Zwanenburg et al., 2013).

Compositions and Compounds

A variety of compounds are now described which can be formulated as needed with further ingredients and used in various methods and applications described herein. Methods for making these compounds are also described.

The stereochemistry of the compounds represented by the formula provided herein (e.g., Formulae II, III, IV, V, and VI) are not particularly limited. Unless otherwise specified, structures shown include all stereoisomers, enantiomers, diastereomers, isomers, and the like, as understood by one skilled in the art. The Formulae, compounds, and compositions also include, for example, salts, solvates, polymorphs, and the like.

As used herein, the phrase "optionally substituted" means that a hydrogen substituent can be replaced by (substituted with) another moiety as understood by one skilled in the art. For example, an optionally substituted C—H moiety can be replaced by C—Cl, C—NO$_2$, or C—OH. There is no particularly limit on what the new substituent such as —Cl or —OH can be as long as it is chemically enabled. In many cases, the new substituent will have ten or fewer atoms. In many cases, the new substituent will have a heteroatom such as O or N. The C of the C—H moiety can be part of an alky, aryl, or alkylaryl group. For an aryl group, the optional substitution can be ortho, meta, and/or para. Substituents can be electron donating or electron accepting. Preferred examples of the substituents in the optionally substituted embodiments include halogens, pseudohalogens, nitro, amino, nitrile, alkoxy, hydroxyl, and other functional groups known in the art. The halogens are F, Cl, Br, and I.

Monovalent and bivalent groups are generally known in the art. Monovalent groups can be represented by —MVG where MVG is the monovalent group (e.g., —CH$_3$) and bivalent groups can be represented by —BVG—where BVG is the bivalent group (e.g., —CH$_2$—).

Compositions and compounds can comprise, consist essentially of, or consist of elements and substituents as known in the art. The appended claims can be open-ended, partially closed, or closed as known in the art.

First, a composition is provided comprising at least one compound which is represented by formula II:

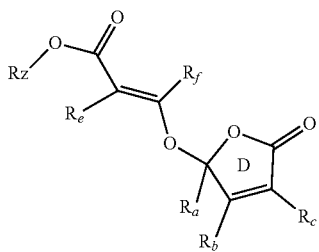

(II)

wherein R$_e$ is an optionally substituted C6-C24 aryl group or an optionally substituted C6-C24 alkylaryl group, and wherein R$_z$ is hydrogen, a monovalent optionally substituted C1-C12 alkyl group, or a bivalent optionally substituted C1-C12 alkylene group which bonds to the optionally substituted C1-C12 aryl group or optionally substituted C1-C12 alkylaryl group of the R$_e$ moiety forming a ring, and wherein R$_a$, R$_b$ and R$_c$, independently from each other, represent:

(a) a hydrogen atom, a halogen atom, a nitro group, a cyano group, a formyloxy group, a formylamino group or a carbamate group, (b) a substituent R$_1$, wherein R$_1$ represents C1-C8-alkyl, C2-C8 alkenyl, C2-C8-alkynyl, C3-C8-cycloalkyl, or C1-C8-alkoxy, in each of which the hydrogen atoms may be partly replaced by other groups or atoms, (c) a substituent —OR$_2$, wherein R$_2$ represents a hydrogen atom, C1-C8-alkyl, C2-C8-alkenyl, C2-C8-alkynyl, C1-C8-alkylcarbonyl, C1-C8-alkylaminocarbonyl or C1-C8-alkoxycarbonyl, in each of which the hydrogen atoms may be partly replaced by other groups or atoms, (d) a substituent —NR$_3$R$_4$, wherein R$_3$ and R$_4$, independently from each other, represent a hydrogen atom, C1-C8 alkyl, C1-C8-alkylcarbonyl, C1-C8-halogenoalkylcarbonyl, phenyl or benzyl, in each of which the hydrogen atoms may be partly replaced by other groups or atoms, (e) a substituent —(O)—R$_5$, wherein R$_5$ represents a hydrogen atom, C1-C8-alkyl or C1-C8-alkyloxy, in each of which the hydrogen atoms may be partly replaced by other groups or atoms, —NH$_2$, NHR$_5$ or NR$_5$R$_5$ (where the two substituents R$_5$ may be the same or different), —NR$_5$(OH), (f) a substituent —S(O)$_n$—R$_6$, wherein n is 0, 1 or 2 and R$_6$ represents C1-C8-alkyl in which the hydrogen atoms may be partly replaced by other groups or atoms, —NH$_2$, —NHR$_6$ or NR$_6$R$_6$ (where the two substituents R$_6$ may be the same or different), or (g) a 4-, 5-, 6- or 7-membered heterocyclic ring comprising up to 4 heteroatoms selected from nitrogen, oxygen or sulfur, where in each of these rings the hydrogen atoms may be partly replaced by other groups or atoms, and R$_f$ represents a hydrogen atom, a halogen atom, a nitro group, a cyano group or C1-C8-alkyl-, C2-C8 alkenyl, C2-C8-alkynyl, or C3-C8-cycloalkyl.

Aryl groups are generally known in the art and include, for example, phenyl (Ph) and naphthyl (Np). Fused aromatic rings can be present. The aryl group can comprise two or more fused phenyl rings. The phenyl rings of the aryl group can be linked by a bridge moiety such as an alkylene group.

Alkylaryl groups are generally known in the art. They are bonded to the Formula II alkene carbon via the alkyl portion of the alkylaryl group. Examples include —CH$_2$-Ph and —CH$_2$CH$_2$-Ph. The aryl portion of the alkylaryl group can be as described herein for aryl groups.

In a preferred embodiment, R$_a$ is hydrogen. In a preferred embodiment, R$_b$ is hydrogen. In a preferred embodiment, R$_f$ is hydrogen. In a preferred embodiment, R$_c$ is an alkyl group, preferably a C1-C4 alkyl group, preferably methyl. In a preferred embodiment, R$_a$ is hydrogen, R$_b$ is hydrogen, R$_f$ is hydrogen, and R$_c$ is methyl.

In a preferred embodiment, Re is the optionally substituted C6-C24 aryl group. More preferably, Re is an optionally substituted C6-C10 aryl group. Preferably, the aryl group has one or two aromatic rings, and the two aromatic rings can be fused.

In particular, in a preferred embodiment, Re is an optionally substituted phenyl group or an optionally substituted naphthyl group.

A particularly preferred embodiment is that Re is an optionally substituted phenyl group.

In one embodiment, Re is represented by Formula III:

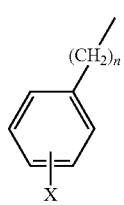

(III)

wherein X of Formula III is a monovalent group which is ortho, meta, or para-substituted, and n is 0, 1, or 2.

Examples of the monovalent group X include nitro, alkyl (include a C1-C12 alkyl such as methyl or ethyl and the like), halogen (such as fluoro, chloro, bromo, or iodo), amino, nitrile, alkoxy (such as C1-C12 alkoxy such as methoxy or ethoxy), aldehyde, carboxylic acid, ester, or hydroxyl. Nitro is a particularly preferred embodiment for X. Para-substituted nitro-phenyl is a particular preferred embodiment for $R_e$.

In another preferred embodiment, Rz is the monovalent optionally substituted C1-C12 alkyl group such as methyl or ethyl. In particular, methyl is a preferred embodiment.

In another embodiment, Rz is the bivalent optionally substituted C1-C12 alkylene group which bonds to an aryl group of the Re moiety forming a ring. Compound 5, below, is an example of Rz forming a ring with the aryl group of $R_e$. For example, in this embodiment, Rz can be a methylene group, —(CH$_2$)—.

In more preferred embodiments, the compound is represented by Formula (IV):

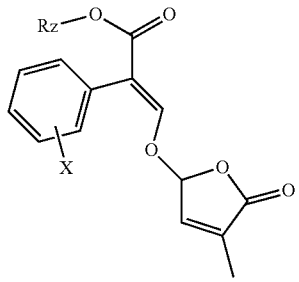

(IV)

wherein Rz is as described as it was defined for Formula (II) and X for Formula IV is a monovalent group as described herein in the ortho, meta, or para position.

In more preferred embodiments, the compound is represented by Formula (V):

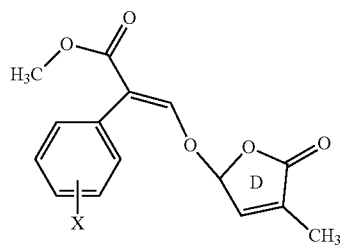

(V)

wherein X for Formula V is ortho, meta, or para-substituted on the phenyl ring and X is nitro, alkyl, halogeno, alkoxy, or hydroxyl.

Specific compounds within the scope of Formula II are shown below including compounds (FIG. 1A, corresponding to compounds MP1-MP11 and MP14-MP15, but excluding MP12 of FIG. 1A which is comparative):

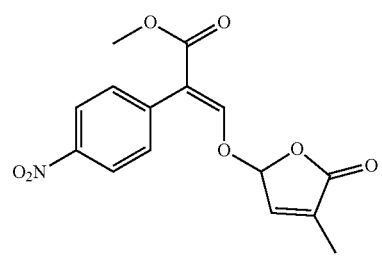

1

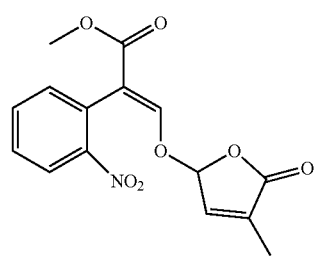

2

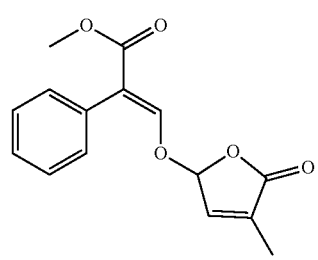

3

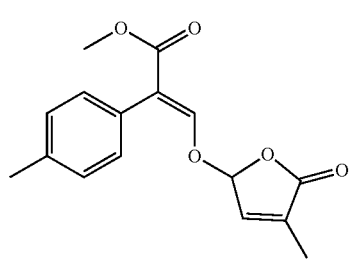

4

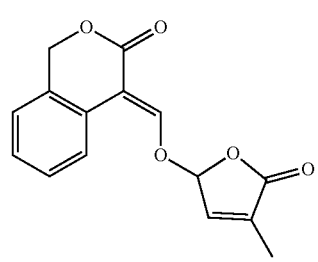

5

-continued

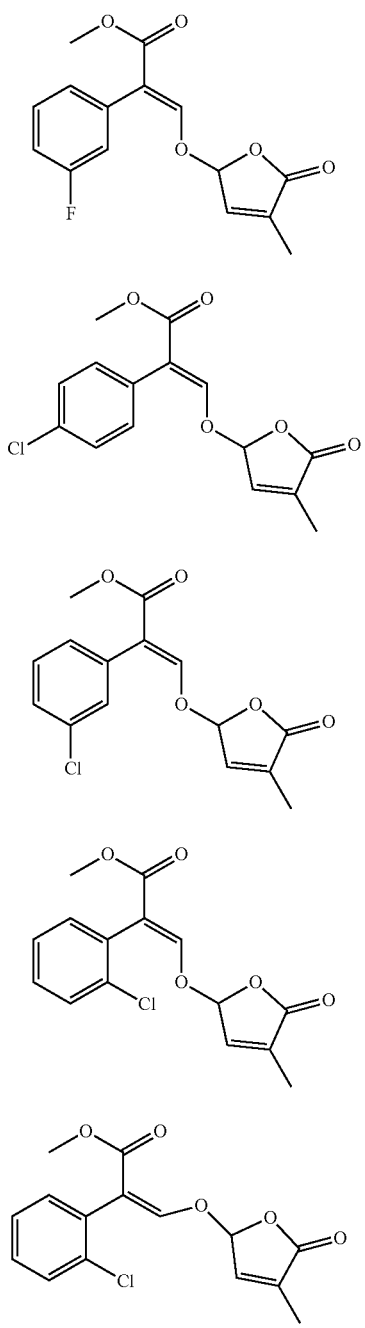

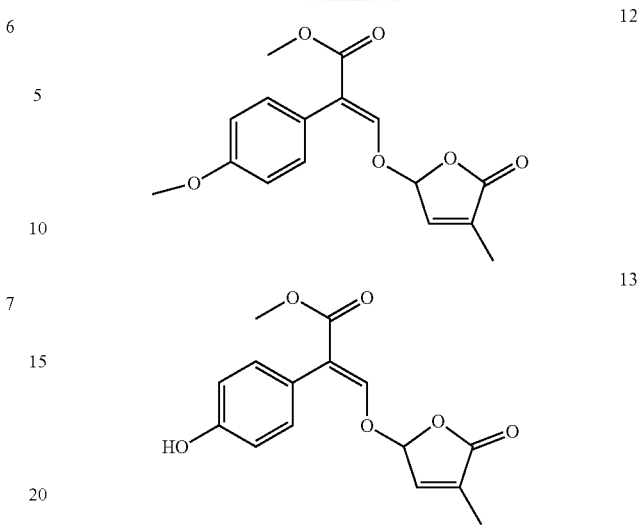

Compound 1 is a particularly preferred embodiment (see working examples below). For clarity, the compounds do not include the compounds claimed and/or described in U.S. Pat. No. 8,980,795.

Compounds A Versus Compounds B

Figure 2:
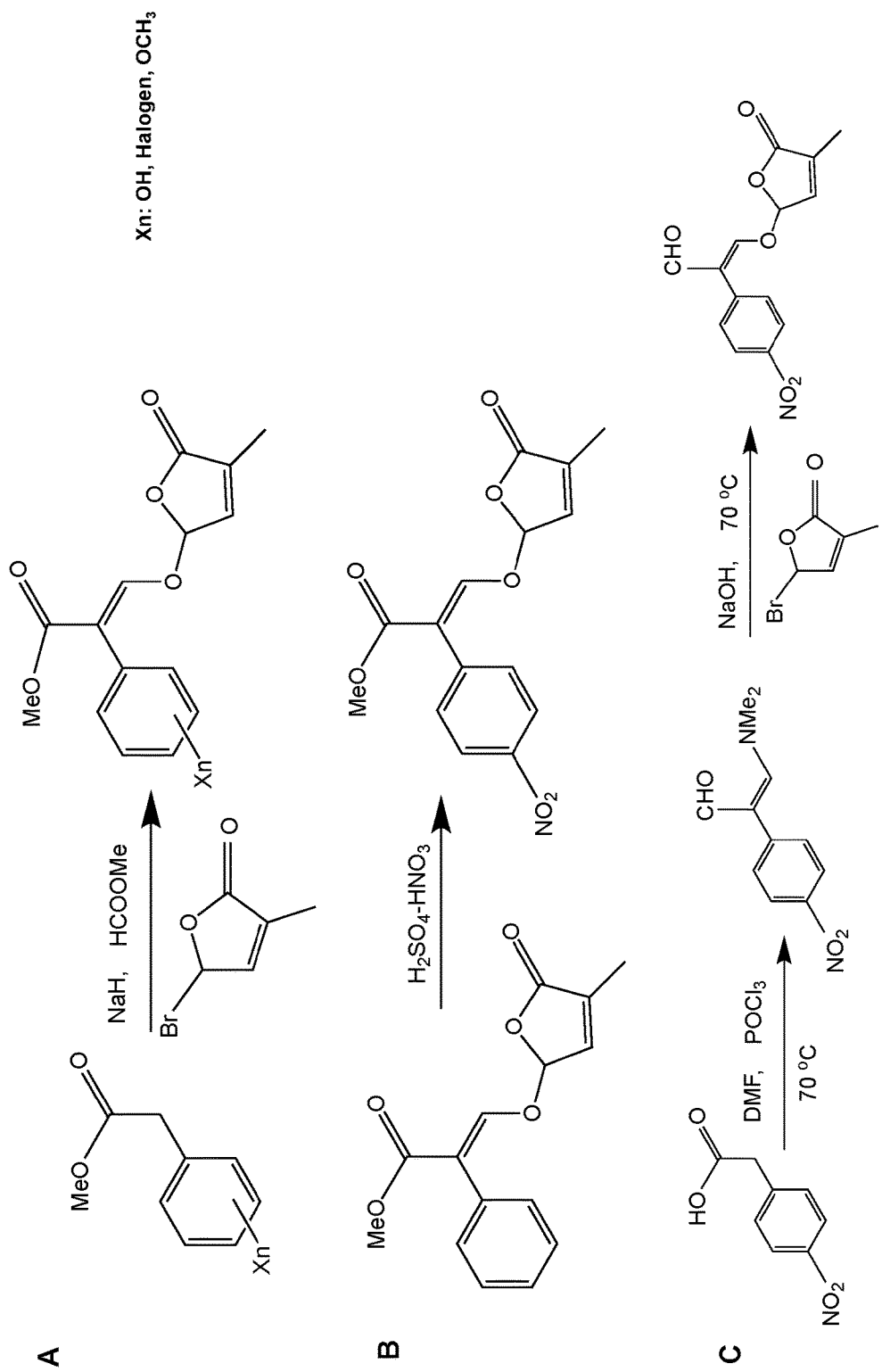
FIG. 2. Synthesis of MPs. Most of the MPs, except MP1 and MP12, were synthesized by following the procedure as described previously (Mangnus et al., 1992). (A) Synthesis of MP3 (E)-methyl 3-(4-methyl-5-oxo-2,5-dihydrofuran-2-yloxy)-2-phenylacrylate (B) Synthesis of MP1 (E)-methyl 3-(4-methyl-5-oxo-2,5-dihydrofuran-2-yloxy)-2-(4-nitrophenyl)acrylate. (C) Synthesis of MP12 (E)-3-(4-methyl-5-oxo-2,5-dihydrofuran-2-yloxy)-2-(4-nitrophenyl)acrylaldehyde.

In an important embodiment, the formulae provided above for Formula II (which can be called "Compounds A") are further described with the exclusionary proviso that the formulae do not include the five compounds shown in the Mangnus, et al., 1992 reference at FIG. 2 (where R is methoxy; see Formula VI). This grouping of compounds based on Formula II but with this exclusionary proviso can be termed "Compounds B." The five excluded compounds in Compounds B are reproduced from Mangus and shown below:

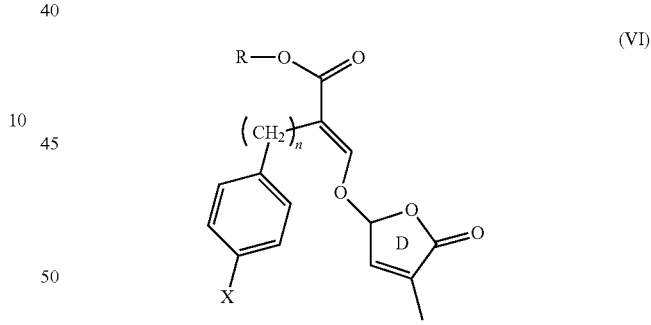

(VI)

Mangnus 1992, FIG. 2 reproduced as Table I:

| Mangnus Compound No. | N | X |
|---|---|---|
| 8 | 2 | H |
| 9 | 1 | H |
| 10 | 0 | H |
| 11 | 0 | Cl |
| 12 | 0 | OCH$_3$ |

In these embodiments, five Formula VI compounds are excluded wherein (i) R is methyl, X is H and n=0; (ii) R is methyl, X is H, and n=1; (iii) R is methyl, X is H, and n=2; (iv) R is methyl, X is Cl, and n=0; and (v) R is methyl, X is —OCH₃ and n=0.

To illustrate, three of these compounds (compounds 10-12 in Mangnus, where n is 0) are shown below, which correspond to compounds MP3, MP7, and MP14 shown in FIG. 1A:

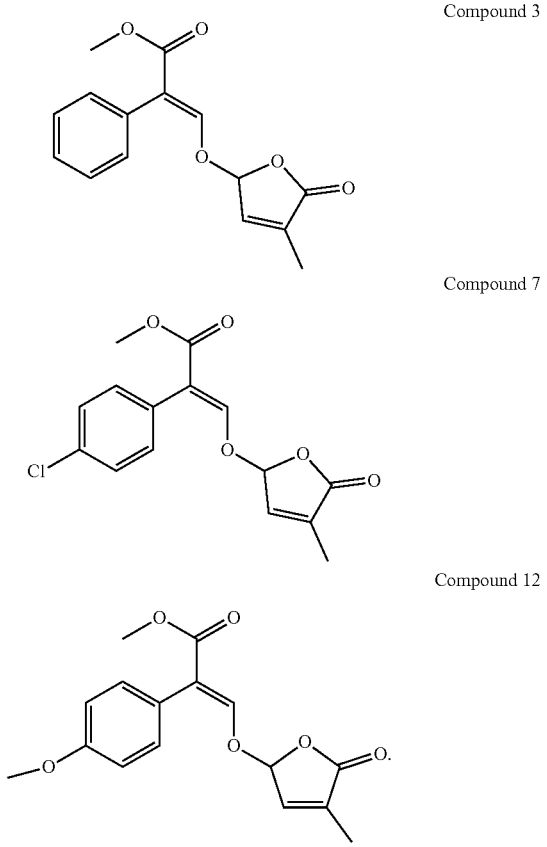

Compound 3

Compound 7

Compound 12

Compounds MP3, MP7, and MP14 (FIG. 1A) were reported to have weak *Striga* germination activity (20-30% germination at millimolar concentrations) (Hearne, 2009). However, for the presently claimed inventions, the germination tests of the working examples have very high activity in inducing seed germination of *Striga* seeds.

In some embodiments, for example, Compounds A (FIG. 1A, minus MP12) can be used for certain compositions, methods, and applications, but in other embodiments, the smaller group of compounds B (which do not include the Mangnus 1992 compounds 8-12, FIG. 19) can be used in other compositions, methods, and applications.

Compositions

For purposes herein, the term "composition" includes both a compound (e.g, those of Formula II) and also a compound mixed with one or more other components. In particular, agriculturally acceptable or agrochemically acceptable ingredients can be used as known by those skilled in the art. The compound such as those of Formula II can be called an "active ingredient" or "active compound" as known in the art. Mixtures of active ingredients can be used. For the methods of use and applications described herein, one skilled in art is aware of other components which can be included. For example, U.S. Pat. No. 8,980,795 describes other components which can be included including insecticides, fungicides, herbicides, and additives.

In many cases, at least one active compound is in the composition, and a mixture of two or more active compounds can be used. Additional ingredients can include a carrier system including one or more carrier solvents including water. Examples of additional ingredients include supports, fillers, surfactants, protective colloids, adhesives, thickeners, stabilizers, thixotropic agents, penetration agents, and sequestering agents. Examples of additives are given in WO 2008/152091 and WO 2008/152092. Other ingredients which can be included in the composition include those known in the art.

In one preferred embodiment, the composition further comprises at least one second active ingredient. For example, in some embodiments, the composition further comprises at least one insecticide compound or fungicide compound.

The molar and weight ratios of the different components can be adjusted for the particular need as known in the art. For example, the amount of active ingredient can be 0.5 wt. % to 99 wt. %, or 10 wt. % to 90 wt. %.

The particular form of the composition is not particularly limited and can be adapted as known in the art.

Methods of Making

The compounds can be made by methods known in the art. Chemical methods can be used, and FIG. 2 illustrates methods for making the compounds. See also working examples herein.

Methods of Using/Applications

Many methods of uses of the compositions and compounds can be carried out, both for compounds A and compounds B. Methods are generally known such as found in the technical literature, e.g., see U.S. Pat. No. 8,980,795 and US Patent Publications 2015/0274690; 2015/0141255.

Target plants are known in the art. Examples of useful plants include rice, wheat, barley, rye, triticale, sugarcane, soybean, peanut, pulse crops, cotton, rape, sunflower, linseed, sugarbeet, fodder beet, potato, and/or dicotyledonous vegetables. Seeds can also be targeted.

Target plants also can be weeds or generally unwanted plants.

A variety of methods are provided comprising applying a composition as described herein for the control of a target plant growth.

A lead embodiment, for example, is a method comprising applying a composition as described herein for the control of a target parasitic plant growth. Compounds B in particular, can be used in this method.

Another embodiment is a method, wherein the control of target plant growth is to encourage the target plant growth.

Another embodiment is a method, wherein the control of target plant growth is to discourage the target plant growth. Compounds B in particular, can be used in this method.

Another embodiment is a method, wherein the control of target plant growth is for controlling the germination of parasitic root plants. Compounds B in particular, can be used in this method.

Another embodiment is a method, wherein the control of target plant growth is for regulating branching, tillering, and root development of plants.

Another embodiment is a method, wherein the control of target plant growth is for controlling hyphal growth of symbiotic mycorrhizal fungi.

Working Examples

Additional embodiments are provided in the following non-limiting working examples.

Chemical Synthesis of Methyl Phenlactonoates

All compounds (FIG. 1A) synthesized here were produced and applied as a racemic mixture of two stereoisomers that differ in the configuration of C2' atom (2'R and 2'S configuration). For the synthesis of MP3 ((E)-methyl 3-(4-methyl-5-oxo-2,5-dihydrofuran-2-yloxy)-2-phenylacrylate), we used a previously described protocol (Mangnus et al., 1992). Sodium hydride (372 mg, 3.32 mM) was added to a cooled (0° C.) and stirred solution of methyl phenylacetate (2.0 g, 13.3 mM) and methyl formate (1.1 ml, 18.0 mM) in dry THF (27 ml) in a 100 ml Erlenmeyer flask. After 10 min, the reaction mixture was warmed to room temperature and stirred overnight under elevated ambient nitrogen. Then reaction mixture was cooled again with an ice bath, and 5-bromo-3-methyl-2(5H)-furanone (2.4 g, 13.3 mM) in THF (5 ml) was gradually added. The mixture was stirred at room temperature for 2 h. The reaction mixture was poured into ethyl acetate (70 ml), and organic layer was washed successively with water (80 ml) and saturated sodium chloride solution (80 ml), dried with sodium sulfate, and concentrated in vacuo. Oily residue was purified with silica gel Wakosil®C-300HG) column with hexane and ethyl acetate as eluent to give title compound MP3 (FIG. 2A). Physicochemical properties of MP3 are shown in Table 1. The compounds MP2, MP4-11, MP13 and MP14 were synthesized following same procedure by using accordingly substituted methyl phenylacetates as starting materials.

MP1 ((E)-methyl 3-(4-methyl-5-oxo-2,5-dihydrofuran-2-yloxy)-2-(4-nitrophenyl) acrylate) was prepared by nitration of MP3 (FIG. 2B). In a 10 ml round-bottom flask, 0.4 ml of concentrated sulfuric acid was added drop-wise to 1 mM of MP3, and cooled with an ice bath. After complete addition of sulfuric acid, approximately 0.2 ml of concentrated nitric acid was added drop-wise with cooling by a small graduated plastic pipette and mixed by gentle swirling. The reaction mixture was then allowed to stand at room temperature for about 15 min and poured into 10 ml of ice water with stirring. Organic chemicals were then extracted three times with ethyl acetate. After evaporation in vacuo, the residue was purified using a silica gel column with ethyl acetate-hexane as eluents to give nitrated compounds (65% yield). This nitrated compounds, 2-nitro (MP2) and 4-nitro (MP1), were separated by reverse-phase column (ODS) with MeOH:water=1:1. Final yield of MP1 is 23%. Physicochemical properties of MP1 are shown in Table 1.

MP12 was a comparative compound. MP12 ((E)-3-(4-methyl-5-oxo-2,5-dihydrofuran-2-yloxy)-2-(4-nitrophenyl) acrylaldehyde) was synthesized as follows. To a stirred solution of 4-nitrophenyl acetic acid (1.8 g) in DMF (5 ml), $POCl_3$ (2.9 ml, 30 mM) was added slowly (over 15 min) so that the reaction temperature was kept below 70° C. Then reaction mixture was stirred at 70° C. for another 12 h. The mixture was poured into 10 g of ice and neutralized by $K_2CO_3$ solution (200 ml). Resultant solid was isolated by filtration, dried to give (Z)-3-(dimethylamino)-2-(4-nitrophenyl)acrylaldehyde, which was used in the next reaction without further purification. (Z)-3-(dimethylamino)-2-(4-nitrophenyl)acrylaldehyde (150 mg, 0.68 mM) and 7.7 N NaOH aq 97 µl (1.1 eq, 0.75 mM) was heated at 70° C. until reaction mixture became homogeneous. Then reaction mixture was dried by evaporation under reduced pressure. To the solution of resultant residue in DMSO (1.5 ml), 5-bromo-3-methyl-2(5H)-furanone (120 mg, 0.68 mM) was added slowly and stirred overnight. The reaction mixture was diluted with diethylether and organic layer was washed successively with water and saturated sodium chloride solution, dried ($Na_2SO_4$) and evaporated (FIG. 2C). The residue was column chromatographed on silica gel using a mixture of hexane and ethyl acetate as eluent to give (E)-3-(4-methyl-5-oxo-2,5-247 dihydrofuran-2-yloxy)-2-(4-nitrophenyl)acrylaldehyde (MP12). Final yield is 51%. Physicochemical properties of MP12 are shown in Table 1.

Chemical Stability

Aqueous solutions of MPs (50 µg ml-1; pH 6.8) were incubated at 21° C. in amber HPLC vials. For sample preparation, 50 µl of an acetone solution (1 mg ml-1) was diluted to the final concentration with methanol (425 µl), water (500 µl) and 25 µl of 1-Indanol (1.0 mg ml-1 solution in acetone) as internal standard. The time course of degradation was monitored by HPLC analysis on a Dionex Ultimate 3000 using a Zorbax Eclipse Plus C18 column (3.5 µm, 2.1×150 mm), eluted by a gradient from 5% to 95% acetonitrile in water within 15 min, and then kept final mobile phase for 4 min. The column was operated at 35° C. with a flow rate of 0.25 ml per min. Compounds eluted from the column were detected with a Diode array detector. Relative quantity of remaining (non-degraded) product was determined by comparison to the internal standard. Stability was monitored at 24 h intervals up to 3 weeks.

Parasitic Weed Seeds Germination Bioassays

Parasitic weed seeds (S. hermonthica and P. ramosa) germination activity was recorded as described previously (Jamil et al., 2012). Six pre-conditioned seed discs were placed in a 90 mm petri-dish containing a filter paper ring wetted with 0.9 ml sterile MilliQ water. Then 50 µl of SL analog solution (10-5 M to 10-12 M) was applied on each six disc, for each concentration. GR24 solutions with equal concentrations and sterile MilliQ water were included as a positive and negative control, respectively. After application, seeds were incubated at 30° C./25° C. in the dark for two days. Germination (seeds with radical emerging through seed coat) was scored under a binocular microscope, and germination rate (%) was calculated.

Rice Micro Tillering Bioassays

Rice seeds (WT, d3, d10) were surface-sterilized by washing with 70% ethanol for 1 min and then with 2.5% sodium hypochlorite for 15 min. Seeds were then rinsed thoroughly with sterile MilliQ water and incubated in water for 2 days at 30° C. in the dark. Pre-germinated seeds were transferred to filter papers containing ½ strength MS medium in 90 mm petri dishes and incubated at 30° C. under fluorescent white light (130-180 µM $m^{-2}$ $s^{-1}$) for one week. Seven day-old seedlings were transferred to 50 ml falcon tubes (one seedling per tube) containing modified half-strength Hoagland nutrient solution and grown in greenhouse. Plants were treated with MPs at 2.5 µM-2.5×10-7 µM, using GR24 as positive control. The compounds were applied six times, twice a week. Number of tillers per plant, plant height and fresh biomass were measured at final harvest.

Protein Expression and Purification

Striga hermonthica ShHTL7 cDNA, GenBank accession KR013127 was kindly provided by Prof. Tadao Asami (The University of Tokyo, Japan). Arabidopsis thaliana D14 (AtD14) cDNA, GenBank accession AY097402 was synthesized and cloned into pUC57 (GenScript). ShHTL7 and OsD14 cDNAs were amplified by RT-PCR using the primers shown in Table 2, digested with BamHI and XhoI, and ligated into BamHI/XhoI digested pGEX-6P-1 expression vector (GE Healthcare). Integrity of plasmids was confirmed by sequencing (KAUST Bioscience Core Lab). The plasmids were then transformed into E. coli BL21 (DE3) cells. The cells were grown in LB broth containing ampicillin (100 mg $ml^{-1}$), incubated at 37° C. until OD600 of 0.6 and induced with 0.1 mM isopropyl-β-D-thiogalactopyranoside (IPTG) at 16° C. for 16 h. Harvested cells were re-suspended in lysis buffer: 50 mM Tris-HCl (pH 8.0), 200 mM NaCl, 0.5% Tween-20 and 2 mM dithiothreitol (DTT). After sonication on ice for 10 mins, the lysate was centrifuged at 25,000 rpm for 30 min at 4° C. Supernatant was allowed to bind to glutathione-sepharose beads (GE Healthcare) for 2 h at 4° C., washed 3 times with buffer (50 mM Tris-HCl (pH 8.0), 200 mM NaCl, 2 mM DTT), and eluted by cleaving GST moiety with PreScission™ Protease (GE Healthcare) at 4° C. overnight. Eluted protein was further purified by gel filtration using HiLoad 16/60 Superdex200 prep grade column (GE Healthcare) on an AKTA prime system (GE Healthcare) in gel filtration buffer (10 mM HEPES pH 7.5, 50 mM KCl and 2 mM DTT). Protein eluted as a sharp single peak and purity was judged by 4-15% SDS-PAGE (Bio-Rad). Purified protein was concentrated using an Amicon 10K filter unit (Merck Millipore) and stored at −80° C. until use. Similar expression and purification protocol was followed for OsD14 protein, except that OsD14 was eluted from Glutathione resins using 0.2 mM reduced Glutathione (Sigma) without cutting GST tag.

Measurement of Dark-Induced Leaf Senescence

One week old rice (*O. sativa*, var. Shiokari) seedlings were established as mentioned above. Uniform seedlings were transferred to 50 ml tubes containing half strength Hoaglands nutrient solution for 7 days and grown in an incubator under white fluorescent light (130-180 µM m$^{-2}$ s$^{-1}$) with 16 h:8 h (L/D) at 28° C. for one week. Leaf segments of 2 cm were cut from middle part of third leaves of rice plants. Each segment was put in a well (in 24-well plates) containing 2 ml of 2.5 mM MES buffer with 0.05% Tween-20, and incubated at 30° C. in the dark for 7 days. After application of MPs, color change, chlorophyll content, ion leakage and gene expression were monitored daily for 7 days.

*Arabidopsis* Hypocotyl Elongation Assays

Sterilized *Arabidopsis* seeds were sown on half strength MS (with 0.5% sucrose+1% agar, 0.5 g L-1 MES, pH 5.7) plates supplemented with MPs or GR24 (at 1.0 µM). Plates were stored at 4° C. in darkness for 3 days. To initiate germination, plates were exposed to continuous white light for 24 h then transferred to continuous monochromatic red light (160 Lux, 22° C.) conditions for another 4 days. For hypocotyl length measurement, at least 30 seedlings were measured using the publically available ImageJ software (http://rsbweb.nih.gov/ij/) after taking digital photographs. Monochromatic red light source was applied as described previously (Wu and Yang, 2010). Light flow rates were measured using a Li250 quantum photometer (Li-Cor, Lincoln, NE, USA).

Measurement of *Arabidopsis* Lateral Root Density and Primary Root Length

Sterilized *Arabidopsis* seeds were sown on half strength MS (with 0.5% sucrose+1% agar, 0.5 g L$^{-1}$ MES, pH 5.7) plates supplemented with GR24 or MPs (at 1.0 µM). Plates were stored at 4° C. in darkness for 3 days and then vertically grown at 22° C. in Percival incubator under long day condition (16 h at 22° C./8 h at 16° C. day/night, 60% relative humidity, 4000-5000 LUX white light) for 8 days. For determining the effect on lateral root density and primary root length, at least 30 seedlings were measured using publically available ImageJ software (http://rsbweb.nih.gov/ij/) after scanning roots.

Intrinsic Tryptophan Fluorescence Assays

ShHTL7 tryptophans were excited at 280 nm and 347 emission intensity was measured at 333 nm. ShHTL7 (10 µM) was incubated at various dilutions (0.2, 0.4, 0.8, 1.6, 3.12, 6.25, 12.5, 25 and 50 µM) of GR24 and MPs for 30 minutes at room temperature before measurement. Each concentration point was measured in triplicates. Emitted fluorescence was monitored using spectraMaxi3 (Molecular Devices) plate reader in 96-wells black plates. Changes in tryptophan fluorescence intensity occur due to conformational changes in protein when it is bound to ligand; differences in fluorescence intensity were recorded and analyzed. Data were normalized and dissociation coefficient (Kd) values were calculated by fitting to a binding saturation single-site model with GraphPad (PRISM 6).

In Vitro Hydrolysis Assays

The hydrolysis of GR24 and MPs by ShHTL7/OsD14 was performed in a total volume of 0.5 ml of PBS buffer containing 10 µM of substrate. Purified ShHTL7/OsD14 was added at a concentration of 50 µg ml$^{-1}$ and incubated for indicated time at 37° C. After adding 1-Indanol (10 µl of a 2.5 mg ml$^{-1}$ solution in methanol), as internal standard, solutions were filtered and transferred to HPLC vials. Hydrolysis of substrates was monitored by HPLC analysis using an Zorbax Eclipse Plus C18 column (3.5 µm, 2.1×150 mm), eluted by a gradient from 10% to 90% acetonitrile in water within 15 min and keeping final condition for 4 min. The column was operated at 30° C. with a flow rate of 0.2 ml min$^{-1}$. Eluted compounds were detected using a Diode Array Detector. Amounts of remaining substrates were determined by calculating corresponding peaks, in comparison to that of internal standard.

YLG (Yoshimulactone Green) In Vitro Assays

In vitro YLG hydrolysis assays were performed as described by Tsuchiya et al., 2015. Hydrolysis assays were carried out using 0.15 µM of recombinant protein OsD14 in a reaction buffer (100 mM PBS buffer, pH 7.3) with 0.1% dimethylsulfoxide (DMSO) at a 300 µl volume on a 96-well black plate (Thermo). For competitive assays, (±) GR24 and (±) MPs at range between 0.03 to 10 µM (or 100 µM) were co-incubated with 0.3 µM of YLG and reacted at 30° C. incubator for 15 min. Fluorescent intensity was measured with excitation at 485 nm and detected at 535 nm. IC50 values were calculated online (http://www.ic50.tk/index.html). Later, values were converted to the existing conditions when treated by 1.0 µM of recombinant proteins.

Statistical Analyses

Statistical analyses were carried out using statistical software package R (version 3.2.2). Dose-response curves and Half Maximum Effective Concentrations (EC50) were calculated to determine optimum amount of MPs. Synthetic strigolactone analog GR24 was used as reference to estimate efficacy of selected compounds. EC50 and estimated response were calculated using drc package (https://cran.r390 project.org/web/packages/drc/) with a Four Parameter Logistic Curve (Dose Response Curve) (Ritz and Streibig, 2005).

The results of the working examples are further described and discussed.

Synthesis and Chemical Stability of MPs

Figure 9:
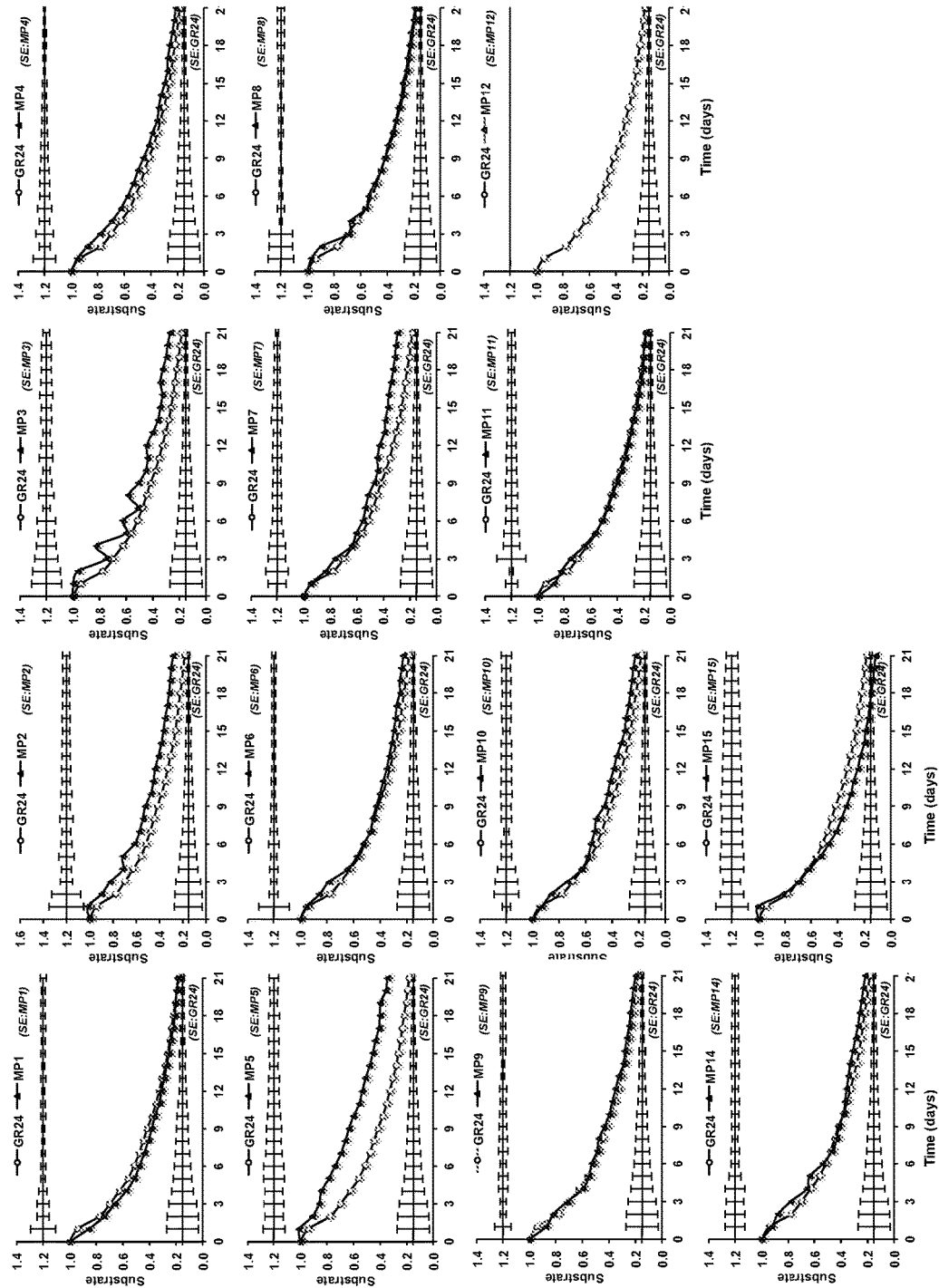
FIG. 9. Stability analysis of MPs in comparison to GR24. The stability of MPs was monitored daily for 3 weeks. Data are means±SE (n=3). X-axis (time (days)); Yaxis (substrate).

The 14 methyl-phenlactonoates (MPs) were synthesized as described above in material and methods section (structures are shown in FIG. 1 and synthesis steps in FIG. 2) and determined their stability, which is a decisive factor for their activity and application. Stability measurements were performed in comparison to GR24, using aqueous solution (pH 6.8) of the different compounds. MP2, MP3, MP4, MP5, MP7, and MP10 were more stable than GR24, with MP5 being the most stable compound (FIG. 9). MP12 that carries an aldehyde function instead of carboxy methyl group was quite unstable and not detectable even after only 24 h. Hence, MP12 was considered comparative. MP1 and MP15 were slightly less stable than GR24, while the stability of MP6, MP8, MP9, MP11, and MP14 was very similar to that of GR24.

MPs are Potent Inducer of Seed Germination in Root Parasitic Weeds

Figure 3:
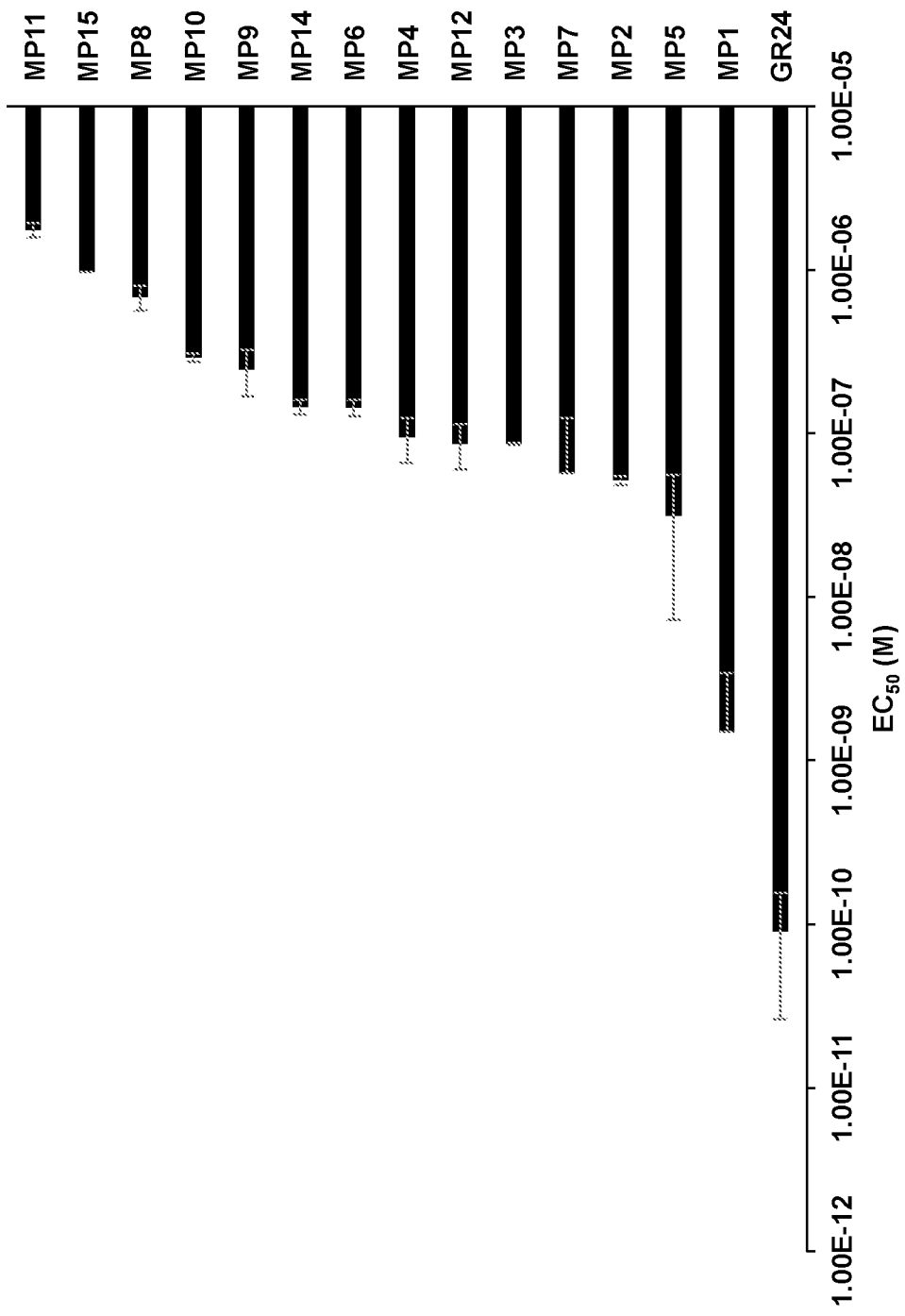
FIG. 3. EC50 (Half Maximal Effective Concentration) of methyl-phenlactonoates for *Striga* seed germination. Concentrations ranging from 10-5 M to 10-12 M were applied in a 50 µl volume on a disc containing 50-100 pre-conditioned *Striga* seeds. GR24 is included as positive control.

The activity of MPs in inducing seed germination of the root parasitic weeds S. hermonthica and P. ramose was determined. In the first assay, MPs at a 1.0 µM concentration were applied. All compounds showed considerable activity in S. hermonthica germination assay (FIG. 10) with rates ranging from 32% (MP11) to 75% (MP1). Differences between MPs were more pronounced in P. ramose germination assay where we observed much higher activity with MP1, MP2, and MP8, compared to other MPs (FIG. 10). Next, half maximal effective concentration (EC50) for S. hermonthica seed germination was established, using concentrations ranging from $10^{-5}$ to $10^{-12}$ M. Among MPs, the highest activity with MP1 that exhibited an EC50 value of $1.5 \times 10^{-9}$ M was observed. Other MPs were at least about five-fold weaker, showing EC50 values ranging from $3.2 \times 10^{-8}$ (MP2) to $1.7 \times 10^{-6}$ M (MP11). The EC50 of the lead compound MP3 was $8.7 \times 10^{-8}$ M. GR24 was the most active analog exhibiting an EC50 value of $9.1 \times 10^{11}$ M (FIG. 3).

MPs Rescue the Tillering Phenotype in Rice d10 Mutant

Figure 4:
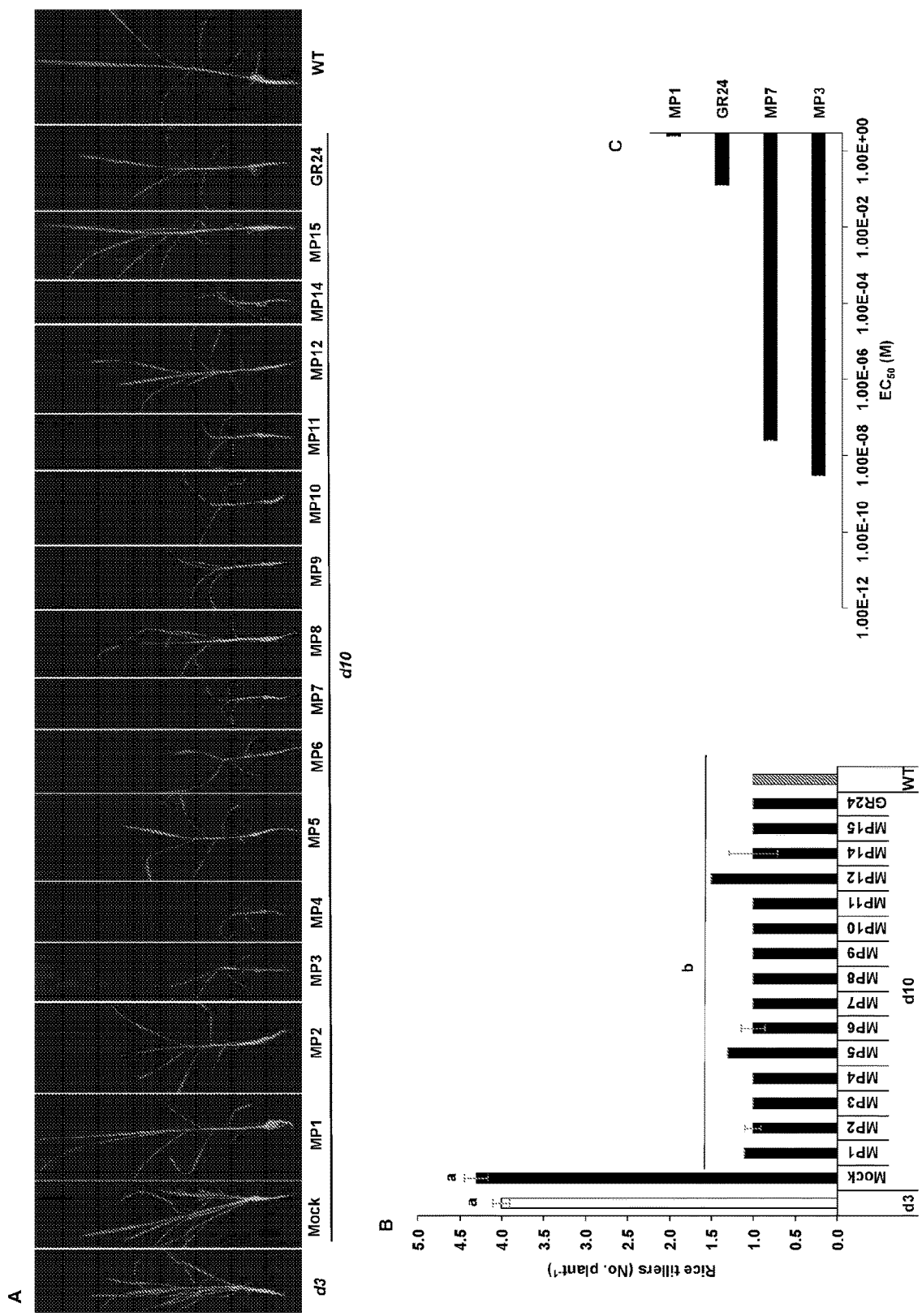
FIG. 4. Rice tillering inhibition by methyl-phenlactonoates. (A) Tillering phenotype of d10 mutant in response to MPs. Methyl-phenlactonoates were applied (2.5 µM) to one week old rice seedlings (Shiokari, d3, d10) grown hydroponically in 50 ml tube twice a week up to three weeks. MP3 treatment led to growth retardation and senescence. (B) Number of tillers per plant counted after three weeks of MPs application. Data are means±SE (n=8) (C) EC50 (Half Maximal Effective Concentration) of selected MPs for tillering inhibition of the rice d10 mutant.
Figure 11:
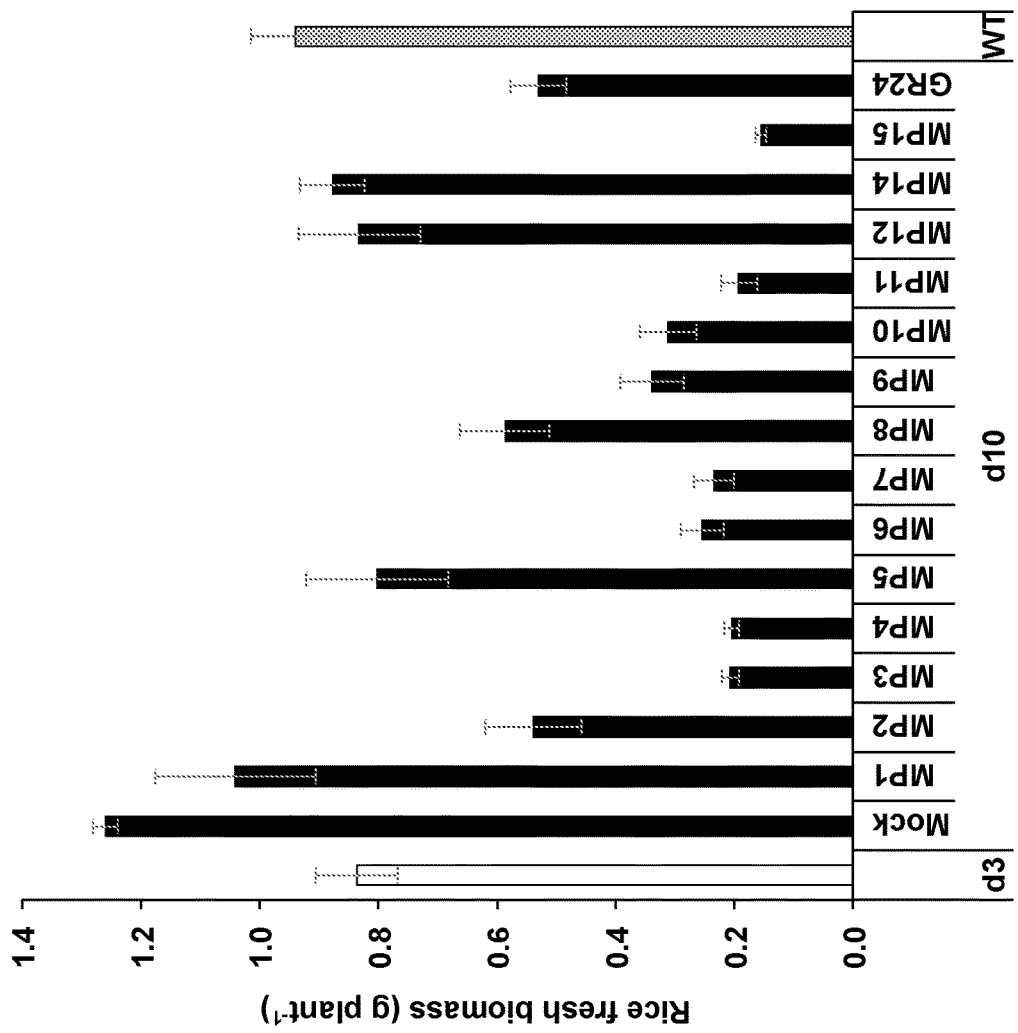
FIG. 11. Effect of MPs on rice fresh biomass. MPs were applied (2.5 µM) to one week old hydroponically grown rice seedlings (Shiokari, d3, d10) twice a week for three weeks. Bars represent means±SE (n=8).
Figure 12:
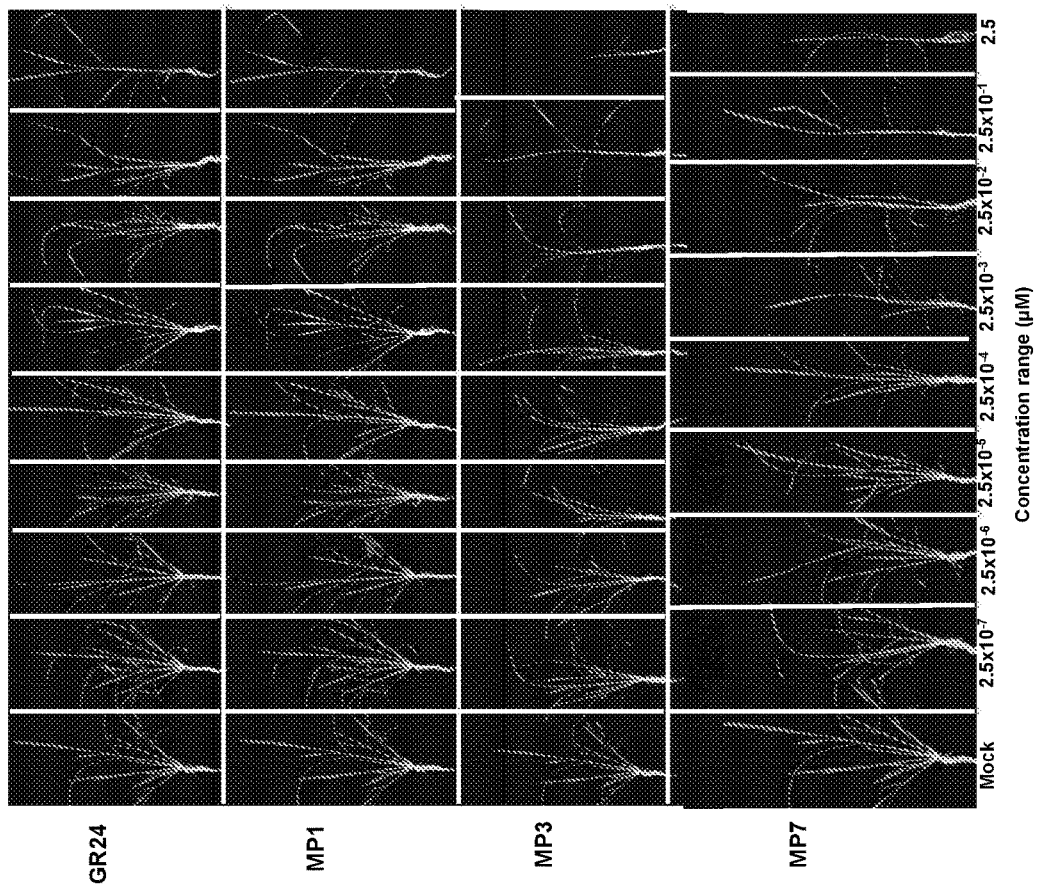
FIG. 12. Picture showing the effect of MPs (MP1, MP3, MP7) and GR24, applied at concentration ranging from 2.5 µM-2.5×10-7 µM, on tillering and growth of d10 seedlings.

Next, it was tested whether MPs restore wild type tillering in the rice d10 mutant. For this purpose, the plants were grown in hydroponic culture, and the compounds were applied at a 2.5 µM concentration. As shown in FIG. 4, all MPs rescued the high tillering phenotype of the d10 mutant, similar to GR24. The recorded number of tillers of d10 was 4 tillers per plant on average in untreated (Mock) plants; this was reduced to 1 tiller per plant in all MPs and GR24 treated samples (FIG. 4A). In contrast, neither MPs nor GR24 could restore the high-tillering phenotype of the SL insensitive d3 mutant that maintained an average of 4 tillers per plant (overall average of all tested compounds) in treated and untreated samples (FIGS. 4A and 4B). This result suggested that MPs act through the SL signaling pathway that requires the D3 protein. The EC50 values of MP1, MP3, and MP7 for reducing the high-tillering phenotype of the d10 mutant were determined, using concentrations ranging from $2.5 \times 10^{-6}$ to $2.5 \times 10^{-12}$ M and in comparison to GR24. MP3 showed the lowest EC50 value ($2.98 \times 10^{-9}$ M), followed by MP7 ($2.54 \times 10^{-8}$ M), GR24 ($1.24 \times 10^{-1}$ M) and MP1 (2.38 M) (FIG. 4C). This result suggests that MP3 and MP7 are more active than GR24 in inhibiting rice tillering, with MP3 being the most active compound (FIG. 4C; FIG. 12). Besides reducing the number of tillers, it was observed that treatment with MP2, MP3, MP6, MP9, and MP10 at 2.5 µM, concentration stunted the growth and caused senescence symptoms of rice seedlings, leading to an obvious decrease in biomass (FIG. 11). It was assumed that this effect is caused by the high activity of these compounds in inducing senescence.

MP3 Accelerates Dark-Induced Leaf Senescence

Figure 5:
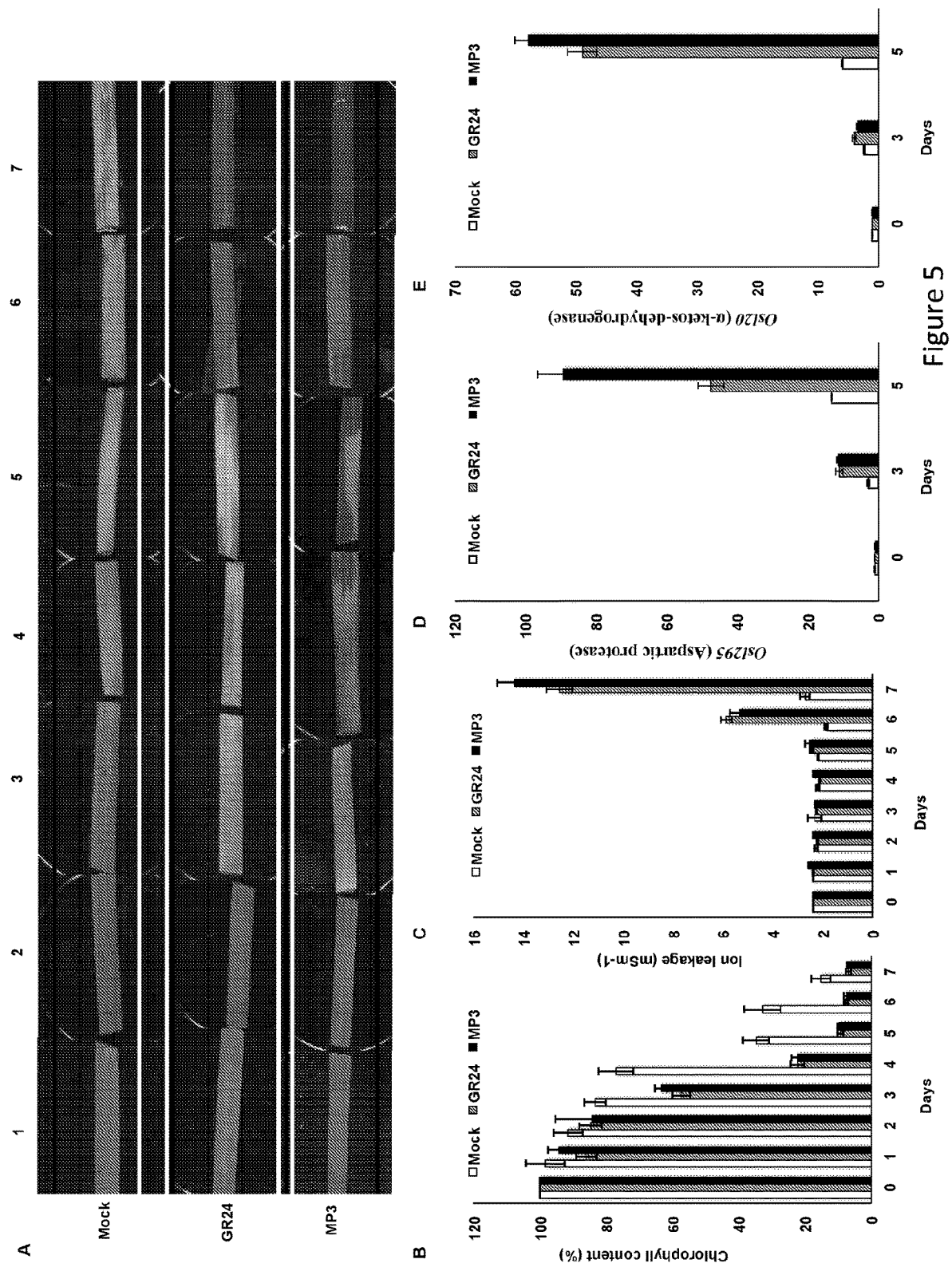
FIG. 5. Measurement of dark-induced leaf senescence, chlorophyll content, ion leakage and transcript level of SAGs in response to MP3 and GR24. (A) Changes in rice leaf color in response to MP3 and GR24. Treated leaf segments were monitored over a 7 day period. (B) Chlorophyll content (C) Membrane ion leakage (D, E) Transcript level of SAGs (Osl20 and Osl295) in the leaf segments was measured on the 1st, 3rd and 5$^{th}$ day after application. Data are means±SE (n=3).

Also investigated was the effect of MP3 on dark-induced leaf senescence, in comparison with GR24. A change in color was observed in GR24 and MP3 treated leaf segments already on the third day after treatment and about two days earlier than the control (FIG. 5A). Consistently, measurement of the chlorophyll content showed a clear reduction in GR24 and MP3 treated segments on the third day, which further increased in the following days (FIG. 5B). Also measured was the ion leakage that is usually caused by senescence. As shown in FIG. 5C, one did not detect a difference between GR24 or MP3 treated segments and the control in the first five days. However, on the sixth and seventh day, both GR24 and MP3 treated leaf segments showed a striking increase, compared to the control. Finally, the transcript levels of the Senescence Associated Genes (SAG) Osl20 (coding for branched chain α-keto dehydrogenase) and Osl295 (coding for aspartic protease) (Lee et al. 2001) were determined. After 5 days of treatment, both genes showed a striking increase in their transcripts, which was more pronounced in MP3 treated samples (FIG. 5D, E).

Effect of MPs on Seedlings Development in Arabidopsis

Figure 6:
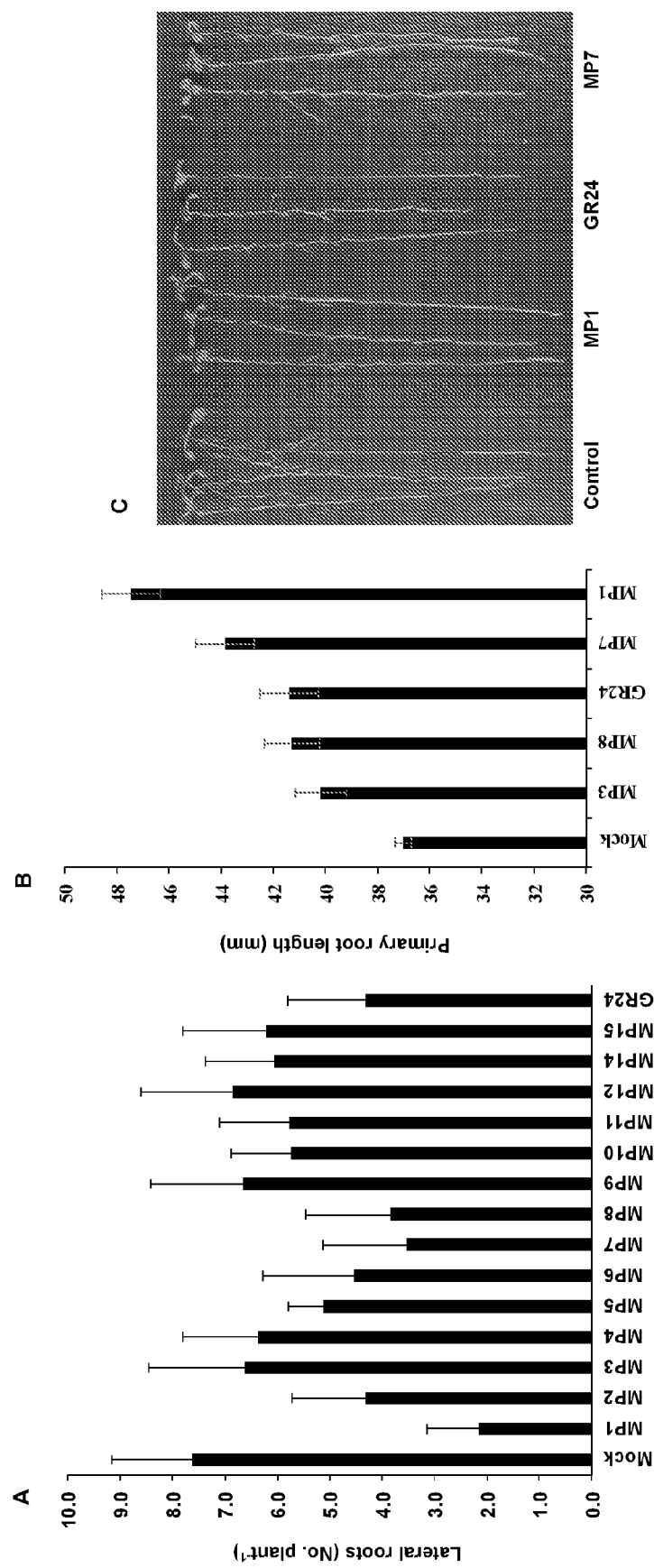
FIG. 6. Effect of MPs on *Arabidopsis* lateral root density and primary root length. (A) Number of lateral roots per plant after MPs application. Eight days old seedlings (at least 30) were photographed digitally, and then measurement was conducted using ImageJ software. Bars represent means±SE. (B) Primary root length in response to the application of MP1, MP3, MP7, MP8 and GR24. Bars represent means±SE. (C) A representative picture showing effect of MP1, MP7 and GR24 on roots architecture.
Figure 13:
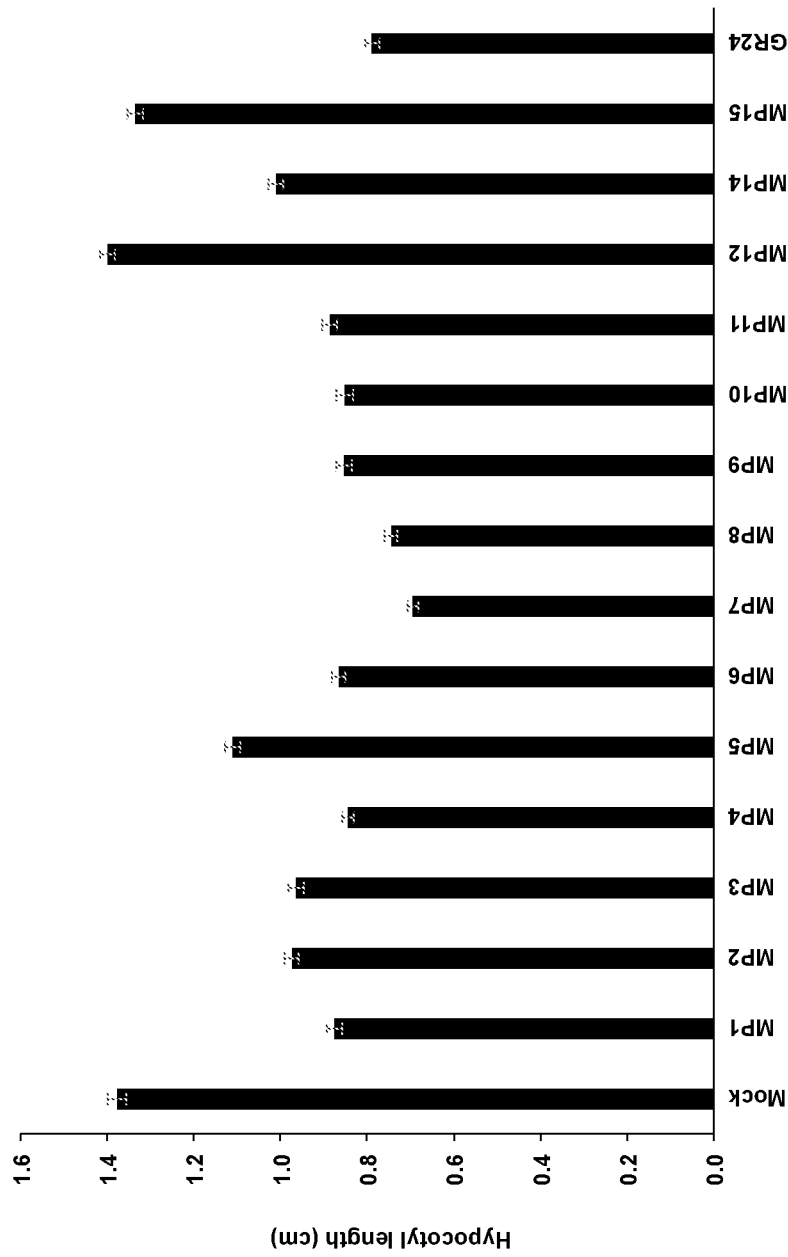
FIG. 13. Effect of MPs on *Arabidopsis* hypocotyl length. Eight days old *Arabidopsis* seedlings (at least 30) were photographed digitally and, measurement of the hypocotyl length was conducted using ImageJ software. Bars represent means±SE.

Also, the effect of MPs on hypocotyl elongation in Arabidopsis seedlings was tested. Apart from MP12 and MP15, all MPs showed significant inhibition of hypocotyl growth, particularly MP7 that displayed a stronger inhibitory effect than GR24 that was applied at the same concentration (1.0 µM; FIG. 13). The effect on lateral roots density was also investigated. Here again, all compounds reduced the number of lateral roots with different efficiencies. MP1 was the most efficient compound and showed an activity higher than that of GR24, followed by MP7 and MP8 that were slightly more active than GR24 (FIG. 6A). Also tested was the activity of MPs in increasing primary root length (FIG. 6B). In this experiment, one evaluated the lead molecule MP3 and three compounds MP1, MP7 and MP8 that showed the highest activity in decreasing lateral root densities. MP1 was the most active compound, followed by MP7 and the positive control GR24. MP3 showed a weaker activity than GR24 and MP8. The latter two caused a similar increase in primary root length (FIG. 6C).

MP1 is the Preferred Substrate for ShHTL7 and OsD14

Figure 7:
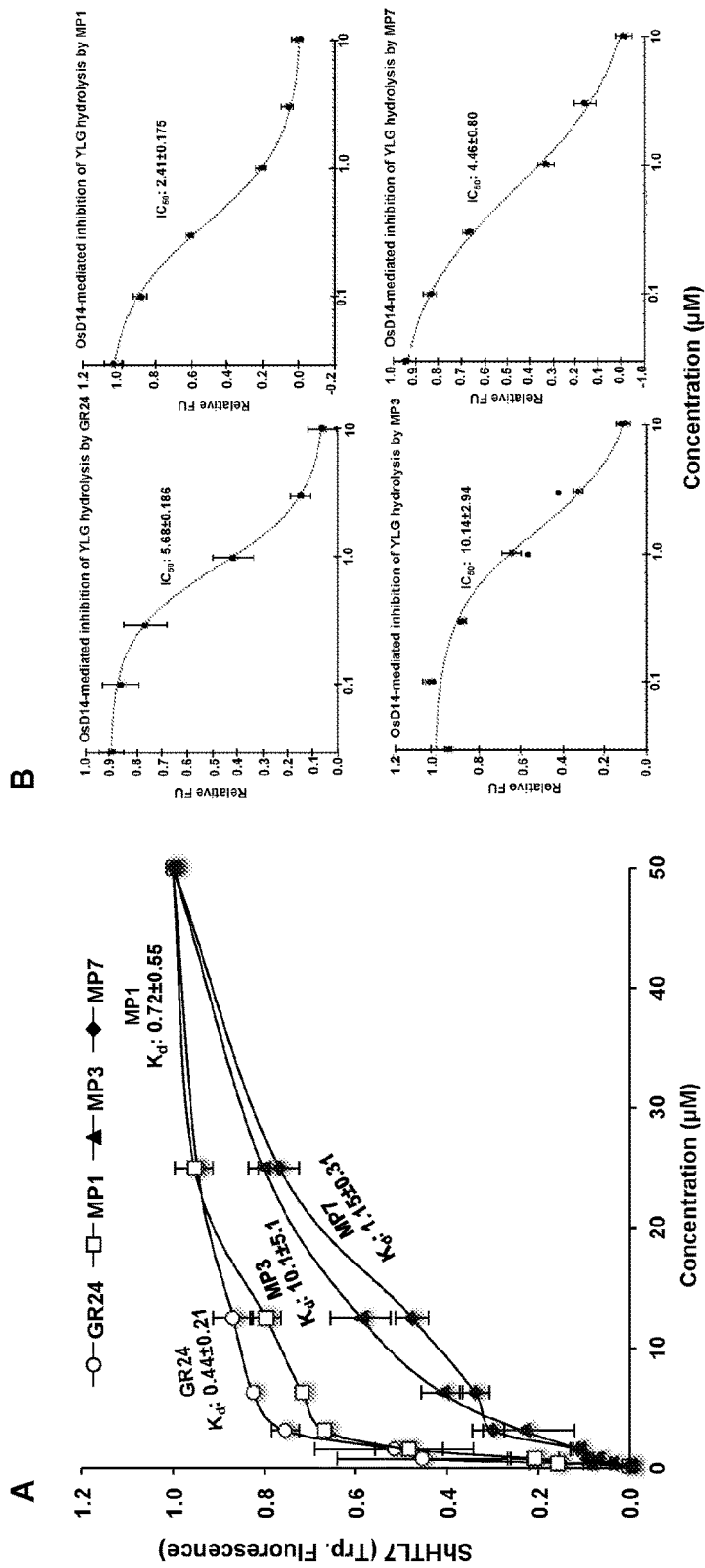
FIG. 7. Affinity of ShHTL7 and OsD14 to MPs. (A) Determination of the affinity of ShHTL7 to GR24 and selected MPs using intrinsic tryptophan fluorescence assay. Changes in fluorescence were used to calculate the dissociation coefficient (Kd). Bars represent means±SE (n=3). (B) Competitive inhibition of OsD14 mediated YLG hydrolysis by GR24 and selected MPs. FU, fluorescence unit. IC50 values for GR24 and MPs are presented with SE (n=3).
Figure 8:
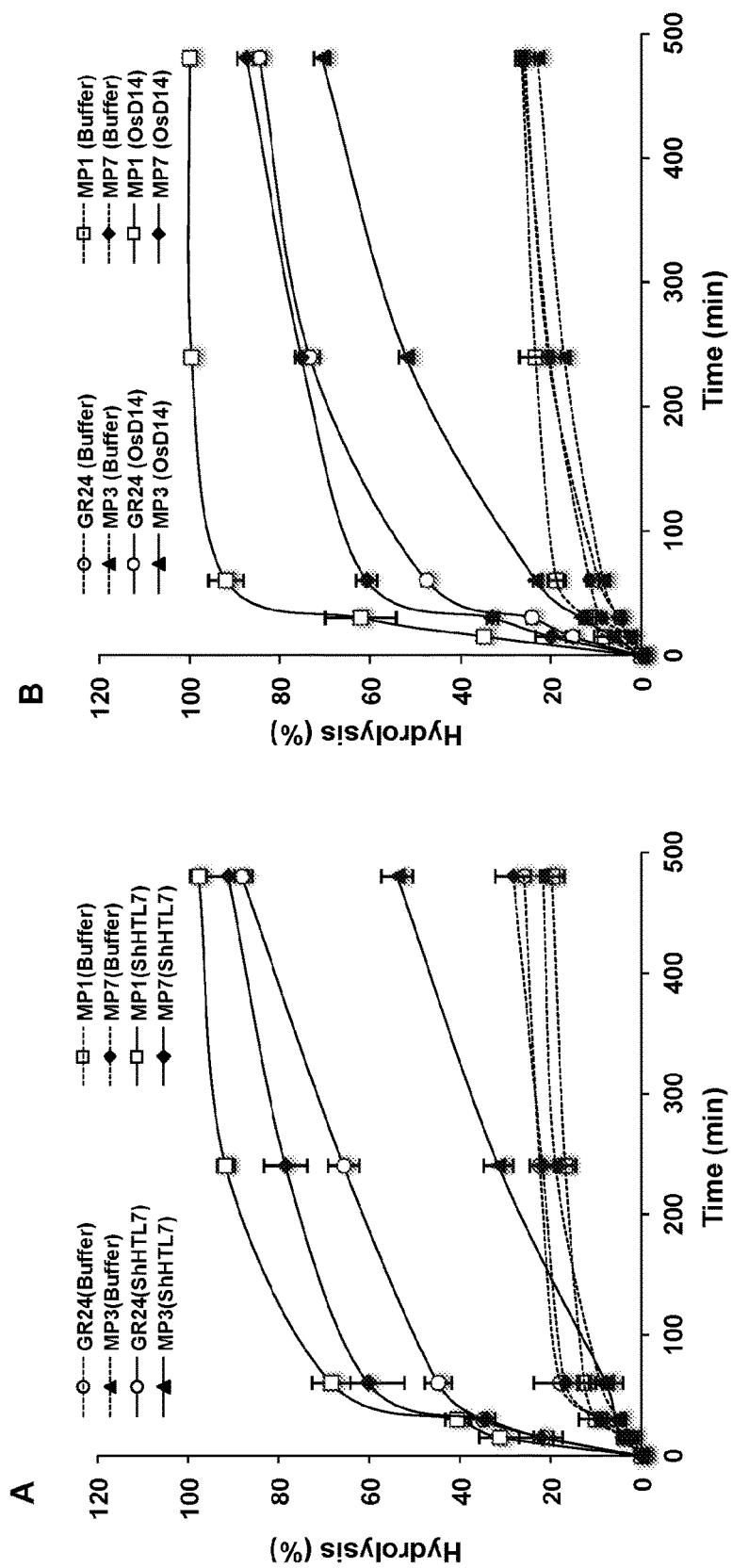
FIG. 8. Hydrolysis of MPs by ShHTL7 and OsD14. (A) Hydrolysis of GR24 and selected MPs by ShHTL7 and (B) OsD14 was monitored by HPLC at the indicated time points (with or without purified ShHTL7 or OsD14). Values represent means±SE (n=3).

To better understand the differences 483 in inducing germination of S. hermonthica seeds, the affinity of ShHTL7 for MP1, MP3, and MP7 was determined by measuring its intrinsic tryptophan fluorescence upon binding to different concentrations of these compounds and in comparison to GR24. ShHTL7 exhibited the highest affinity towards GR24 with a Kd value of 0.44±0.21 µM (FIG. 7A). One observed a slightly weaker affinity to MP1 (Kd: 0.72±0.55 µM), followed by MP7 (Kd: 1.15±0.31 µM), and the lowest affinity to MP3 (Kd: 10.1±5.1 µM) (FIG. 7A). To test affinity of MPs towards OsD14, a competition hydrolysis assay was performed using the fluorescent analog YLG and IC50 values were determined. As depicted in FIG. 7B, OsD14 showed the highest affinity towards MP1 (2.41±0.175 µM), followed by MP7 (4.46±0.80 µM), GR24 (5.68±0.183 µM) and finally MP3 (10.14±2.94 µM). The hydrolysis rates of three MPs by SHTL7, in comparison to GR24, were investigated. For this purpose, one incubated purified SHTL7 with the compounds and monitored hydrolysis by HPLC after defined time intervals. As shown in FIG. 8A, one observed the highest hydrolysis rates with MP1, followed by MP7, GR24 and finally MP3. Also tested was hydrolysis of three MPs by purified OsD14. Here again, one observed the same tendency, by detecting the highest hydrolysis rate with MP1, followed by MP7, GR24 and finally MP3 (FIG. 8b).

Further discussion of the working examples is provided. SLs regulate different aspects of plant development and responses to environmental changes. Moreover, they play a key role in the life cycle of root parasitic weeds and in establishing the plant beneficial mycorrhizal symbiosis. Therefore, SLs can be used for application in agriculture, horticulture and forestry (Screpanti et al., 2016). Sources of natural SLs are quite limited, since plants usually produce these compounds at very low concentrations (exudates of 300,000 sorghum plants were required to isolate only 5 µg sorgolactone (Humphrey et al., 2006)). Moreover, organic synthesis of natural SLs is challenging, due to their complex structures that also contains several chiral centers (Zwanenburg et al., 2013). Therefore, there is a need for low-cost and efficient SL analogs/mimics. Developing SL analogs with specificity for particular function(s) would also imply an important step in translating SL research into applications.

Particular interest is in developing SLs analogs that can be applied as a suicidal seed germination agent to combat the root parasites *S. hermonthica* and *P. ramosa*. The suicidal germination approach would address a major constraint in the control of root parasitic weeds, which is the generally observed large size of seed bank of parasite-infested soil. Seasonal applications of germination stimulants in the absence of a host would gradually deplete this seed bank. This strategy has been recently tested in *P. ramosa* and *S. hermonthica* infested tobacco and sorghum fields, respectively (Samejima et al., 2016; Zwanenburg et al., 2016). Results obtained from these field trials are both uncertain and promising and demonstrate the feasibility of suicidal germination approach and consequently the importance of developing optimized SLs analogs.

Most knowledge about SLs functions was deducted from experiments performed with the widely used SL analog GR24. However, the synthesis of this compound is laborious and requires 6-8 steps (Malik et al., 2011). Similarly, the synthesis of potent fluorescent analog CISA-1 requires 8 steps (Rasmussen et al., 2012). Other compounds, such as AR36 (Boyer et al., 2014) and 4-Br debranone (4BD) (Fukui et al., 2013), which contain a D-ring connected by an enol ether bridge to less complex second moieties, showed moderate activity in inducing parasite seed germination. Nijmegen-1 is a potent inducer of seed germination in *P. ramosa*, but with an EC50 that is 3 orders of magnitude higher than GR24, it causes a weak germination response of *S. hermonthica* (Wigchert et al., 1999). In this working example study, a new series of SL analogs, MPs, which resemble non-canonical SL methyl carlactonoate, were developed. MPs are easy to prepare and very potent in inducing seed germination of *S. hermonthica* seeds and in exerting several SL developmental functions, such as inhibition of tillering, triggering senescence and regulation of root architecture in *Arabidopsis*.

Previously, a carlactone-based analog, nitro-phenlactone, was designed that showed very weak activity in stimulating *S. hermonthica* germination (Jia et al., 2016). In the above working examples, the structure of nitro-phenlactone was modified by replacing the methyl group by a methyl carboxyl group, which led to MP1, the most efficient *Striga* germination stimulant (EC50=$1.5 \times 10^{-9}$ M) among the MPs tested herein. This activity was just around 17 times weaker than that of GR24, pointing to MP1 as a suitable candidate for the suicidal germination approach.

Very recently, the activity of MP1 was also evaluated in a trial conducted in Burkina Faso, in which $1 \times 1$ m$^2$ wooden boxes were used which were filled with artificially infested soil and pearl millet as a host. In this experiment, MP1 showed even significantly higher germination activity than GR24. The activity of MP1 in inducing seed 549 germination in *P. ramosa* was quite similar to that of GR24 and only slightly weaker than that of MP2 that carries the nitro group at the ortho position and of the chlorophenyl compound MP8. Apart from these three compounds, one observed lower germination activity with *P. ramosa* seeds than with those of *S. hermonthica*.

To test whether MPs can recover the high-tillering phenotype of SL deficient d10/CCD8 mutant, a hydroponic culture system was used (FIG. 4). The tillering inhibition observed with all MPs in d10 mutant and insensitivity of high-tillering perception mutant d3 prove that these compounds act as SL analogs via the F-box protein D3/MAX2-dependent signaling pathway. The high activity of MP3 and MP7 prompted a quantification of the effect on tillering in more detail and to determine the corresponding EC50 value. The results obtained demonstrate that both MP3 (EC50=$2.98 \times 10^{-9}$ M) and MP7 (EC50=$2.54 \times 10^{-8}$ M) are more efficient than GR24 (EC50=$1.24 \times 10^{-1}$ M) in restoring wild type tillering to d10 mutant. MP1, that showed the highest activity in *S. hermonthica* seed germination test, was weaker than GR24. One also observed that the treatment with several MPs (at 2.5 µM), particularly MP3, leads to growth retardation and senescence. Therefore, the activity of MP3 was tested in accelerating dark-induced leaf senescence, as reported for SLs before (Yamada et al., 2014). In this experiment, treatment with MP3 accelerated the change in leaf color and led to a decrease in chlorophyll content and an increase in electrolytes leakage, similar to GR24. Supporting data were also obtained by investigating the changes in transcript levels of senescence-associated genes Osl295 and Osl20. These results suggest the possibility of developing MP-based post emergence herbicides.

The growth promoting effect of widely used GR24 on primary roots is subtle and depends on the plant species and growth conditions (Ruyter-Spira et al., 2013). Moreover, it is less pronounced than the inhibitory effect of this compound on lateral root densities (Matthys et al., 2016). This study on the activity of MPs on root architecture in *Arabidopsis* demonstrates that MP7 and particularly MP1 are more efficient than GR24 in inducing the growth of primary roots and reducing the lateral root density. These results suggest that MP1 and, to a lesser extent, MP7 are better analogs for investigating the role of SLs in regulating root architecture in *Arabidopsis* and, likely, in other species. Interestingly, nitro-phenlactone that lacks the enone moiety did not affect lateral roots density as reported by Jia et al., 2016. To the best of our knowledge, MP1 is the first reported analog 582 that outperforms GR24 in impacting root development.

Comparison of the activities of different MPs unraveled the impact of substitutions in phenyl ring on the efficiency of these compounds in exerting specific SL functions. The lead compound MP3 was less active than MP1 in inducing *S. hermonthica* seed germination but showed the most pronounced inhibitory effect on tillering. Substitutions increased the efficiency of the compounds in inducing seed germination and in regulating root architecture. Besides being the most potent compound in the *S. hermonthica* seed germination assay, MP1 also showed the highest activities in repressing the number of lateral roots and enhancing the length of primary roots, followed by the chlorophenyl-containing MP7 and MP8. The position of the modification can be decisive. Among the chlorophenyl compounds MP7, MP8 and MP9, one observed highest germination activity with MP7 (Cl in para position) followed by MP9 (ortho position) and MP8 (meta position).

To shed light on molecular events underlying the differences in activity between MP1, MP3 and MP7, the affinity of *S. hermonthica* SL receptor ShHTL7 for these compounds was determined. The results obtained were consistent with the *S. hermonthica* germination assay, with GR24 being the most active ligand followed by slightly weaker MP1, MP7 and finally MP3. However, one observed higher hydrolysis activities with MP3 and MP7 than with GR24. These compounds were also compared regarding their hydrolysis by rice SL receptor D14, and a competition assay with fluorescent analog YLG was performed. MP1 exhibited the highest hydrolysis rate and the lowest IC50, followed by MP7, GR24 and finally MP3. It may be that the high conversion of MP1 and MP7 is due to the presence of electron withdrawing groups $NO_2$ (MP1) and Cl (MP7), which alleviate the hydrolysis by the two receptors. In the case of ShHTL7 assays, hydrolysis and affinity results are consistent with the determined biological activity. In contrast, MP3 was the less preferred substrate in the incubations with OsD14, although it showed the highest activity in the tillering assay. This difference indicates that other factors, such as uptake and transport, are also decisive for the tillering inhibitory and growth retarding activity. However, it is also possible that hydrolysis rates determined here do not accurately reflect the situation in planta where D14 is part of a protein complex that may impact/modulate hydrolysis activity of this receptor.

In conclusion, the working example findings showed that MPs are highly efficient SL analogs which can be used to investigate the biological functions of SLs and employed to combat root parasitic weeds or to modulate plant architecture. Moreover, the working example study demonstrated that type and position of substitutions in the phenol-ring, which corresponds to A-ring in SLs, determine and modulate the efficiency of MPs in exerting specific SLs functions.

TABLE 1

Physico-Chemical Properties of Methyl Phenlactonoates

| MPs# | Physico-Chemical Property |
|---|---|
| MP1 | $^1$H NMR (500 MHz, CDCl3): d 7.74 (1H, s), 7.34 (2H, d, J = 7.5 Hz), 7.30 (3H, m,), 6.85(1H, s), 6.14 (1H, s), 3.76 (3H, s), 1.97 (3H, s). HRMS-Esi: m/z [M − Na]− Calcd for C15H14Na1O5: 297.07389, found: 297.07252. |
| MP2 | $^1$H NMR (500 MHz, CDCl3): d 8.05 (1H, d, J = 8 Hz), 7.75 (1H, s), 7.60 (1H, t, J = 7.5 Hz), 7.48 (1H, t, J = 8 Hz), 7.37 (1H, d, J = 7.5 Hz), 6.83 (1H, s), 6.13 (1H, s), 3.72 (3H, s), 1.97 (3H, s). HRMS-Esi: m/z [M − Na]− Calcd for C15H13N1Na1O7: 342.05897, found: 342.05710. |
| MP3 | $^1$H NMR (500 MHz, CDCl3): d 8.20 (2H, d, J = 9 Hz), 7.84 (1H, s), 7.49 (2H, d, J = 8.5 Hz), 6.87 (1H, s), 6.17 (1H, s), 3.79 (3H, s), 2.00 (3H, s). HRMS-Esi: m/z [M − Na]− Calcd for C15H13N1Na1O7: 342.05897, found: 342.05741. |
| MP4 | $^1$H NMR (500 MHz, CDCl3): d 7.71 (1H, s), 7.18 (4H, m), 6.85 (1H, s), 6.13 (1H, s), 3.76 (3H, s), 2.35 (3H, s), 1.97 (3H,s). HRMS-Esi: m/z [M − Na]− Calcd for C16H16Na1O5: 311.0895, found: 311.08907. |
| MP5 | $^1$H NMR (500 MHz, CDCl3): d 7.90 (1H, s), 7.81 (1H, d, J = 7.5 Hz), 7.34 (1H, t, J = 8 Hz), 7.27 (1H, t, J = 8 Hz), 7.17 (1H, d, J = 7.5 Hz), 7.03 (1H, s), 6.29 (1H, s), 5.29 (2H, dd, J = 18.5, 8.5 Hz), 2.05 (3H, s). HRMS-Esi: m/z [M − Na]− Calcd for C15H12Na1O5: 295.05824, found: 295.05756. |
| MP6 | $^1$H NMR (500 MHz, CDCl3): d 7.75 (1H, s), 7.30 (1H, q, J = 7 Hz), 7.08 (1H, d, J = 6.5 Hz), 7.01 (2H, m), 6.87 (1H, s), 6.14 (1H, s) 3.77 (3H, s), 1.99 (3H, s). HRMS-Esi: m/z [M − Na]− Calcd for C15H13F1Na1O5: 315.06447, found: 315.06407. |
| MP7 | $^1$H NMR (500 MHz, CDCl3): d 7.74 (1H, s), 7.31 (2H, d, J = 8.5 Hz), 7.24 (2H, d, J = 8.5 Hz), 6.86 (1H, s), 6.13 (1H, s), 3.77 (3H, s), 1.99 (3H, s). HRMS-Esi: m/z [M − Na]− Calcd for C15H13Cl1Na1O5: 33103492, found: 331.03461. |
| MP8 | $^1$H NMR (500 MHz, CDCl3): d 7.77 (1H, s), 7.30 (3H, m), 7.20 (1H, m), 6.89 (1H, s), 6.16 (1H, s), 3.79 (3H, s), 2.01 (3H, s). HRMS-Esi: m/z [M − Na]− Calcd for C15H13Cl1Na1O5: 33103492, found: 331.03503. |
| MP9 | $^1$H NMR (500 MHz, CDCl3): d 7.75 (1H, s), 7.41 (1H, m), 7.26 (2H, m), 7.21 (1H, m), 6.84 (1H, s), 6.13 (1H, s), 3.74 (3H, s), 1.96 (3H, s). HRMS-Esi: m/z [M − Na]− Calcd for C15H13Cl1Na1O5: 33103492, found: 331.03401. |
| MP10 | $^1$H NMR (500 MHz, CDCl3): d 7.39 (1H, d, J = 7 Hz), 7.28 (3H, m), 7.06 (1H, s), 6.82 (1H, s), 6.16 (1H, s), 3.71 (3H, s), 2.01 (3H, s). HRMS-Esi: m/z [M − Na]− Calcd for C15H13Cl1Na1O5: 33103492, found: 331.03452. |

TABLE 1-continued

Physico-Chemical Properties of Methyl Phenlactonoates

| MPs# | Physico-Chemical Property |
|---|---|
| MP11 | $^1$H NMR (500 MHz, CDCl3): (E- and Z- stereoisomers are the major and minor products, respectively) d 7.96 (1H major isomer, s), 7.79-7.88(2H major isomer and 3H minor isomer of aromatic rings, m), 7.69(1H major isomer, m), 7.43-7.51(3H major isomer and 3H minor isomer of aromatic rings, m), 7.37(1H minor isomer, d, J = 7 Hz), 7.32(1H major isomer, d, J = 7 Hz), 7.17(1H minor isomer, s), 6.89(1H minor isomer, s), 6.70(1H major isomer, s), 6.16(1H minor isomer, s), 6.11(1H major isomer, s), 3.70(3H major isomer, s), 3.64(3H minor isomer, s), 2.01(3H minor isomer, s) 1.89(3H major isomer, s). HRMS-Esi: m/z [M − Na]− Calcd for C19H16Na1O5: 347.08954, found: 347.08909. |
| MP12 | Final yield is 51%. 1H NMR (500 MHz, CDCl3): d 9.15 (1H, s), 8.23 (2H, d, J = 9 Hz), 7.60 (2H, d, J = 8.5 Hz), 7.44 (1H, s), 6.97 (1H, s), 6.29 (1H, s), 2.04 (3H, s). |
| MP14 | $^1$H NMR (500 MHz, CDCl3): (E- and Z- stereoisomers are the major and minor products, respectively) d 7.70 (1H major isomer, s), 7.24 (2H d, J = 8.5 Hz major isomer) 7.21 (2H d, J = 8.5Hz minor isomer), 7.03(1H minor isomer, s), 6.90-6.86(3H major isomer and 2H minor isomer, m), 6.82(1H minor isomer, s), 6.13(1H major isomer, s), 6.12(1H minor isomer, s), 3.81(3H minor isomer, s), 3.80(3H major isomer, s), 3.77(3H minor isomer, s), 3.76(3H major isomer, s), 2.00(3H minor isomer, s), 1.98(3H major isomer, s). HRMS-Esi: m/z [M − Na]− Calcd for C16H16Na1O6: 327.08446, found: 327.08362. |
| MP15 | $^1$H NMR (500 MHz, CDCl3): d 7.71 (1H, s), 7.19 (2H, d, J = 8.5 Hz), 6.87 (1H, s), 6.81 (2H, d, J = 9 Hz), 6.14 (1H, s), 5.04 (1H, bs), 3.77 (3H, s), 1.99 (3H, s). HRMS-Esi: m/z [M − Na]− Calcd for C15H14Na1O6: 313.06881, found: 313.06760. |

TABLE 2

List primers sequences used in this study

| Primer name | Sequences (5'-3') | Restriction site | Purpose |
|---|---|---|---|
| ShHTL7-F | CGggatccATGAGCTCAATTGGATTAGCCCBamHI (SEQ ID NO: 1) | | Protein cloning |
| ShHTL7-R | CCGctcgagTCAGTGATCCGTGATGTCCTGXhoI (SEQ ID NO: 2) | | Protein cloning |
| Osl20-F | TCAGGAACAATGTGAGGCAAGAG (SEQ ID NO: 3) | | qRTPCR |
| Osl20-R | CGCGGTTTCGGCATTCTTTCTG (SEQ ID NO: 4) | | qRTPCR |
| Osl295-F | TGATGGGAAGCATGGTGTTAGTG (SEQ ID NO: 5) | | qRTPCR |
| Osl295-R | CACTTTGGAGACCATTCGATTCC (SEQ ID NO: 6) | | qRTPCR |
| Ubi-F | GCCCAAGAAGAAGATCAAGAAC (SEQ ID NO: 7) | | qRTPCR |
| Ubi-R | AGATAACAACGGAAGCATAAAAGTC (SEQ ID NO: 8) | | qRTPCR |

REFERENCES

Abe S, Sado A, Tanaka K, Kisugi T, Asami K, Ota S, II Kim H, Yoneyama K, Xie X, Ohnishi T, Seto Y, Yamaguchi S, Akiyama K, Yoneyama K, Nomura T. 2014. Carlactone is converted to carlactonoic acid by MAX1 in *Arabidopsis* and its methyl ester can directly interact with AtD14 in vitro. *Proceedings of the National Academy of Sciences of the United States of America* 111, 18084-18089.

Agusti J, Herold S, Schwarz M, Sanchez P, Ljung K, Dun E A, Brewer P B, Beveridge C A, Sieberer T, Sehr E M, Greb T. 2011. Strigolactone signaling is required for auxin-dependent stimulation of secondary growth in plants. *Proceedings of the National Academy of Sciences of the United States of America* 108, 20242-20247.

Akiyama K, Matsuzaki K, Hayashi H. 2005. Plant sesquiterpenes induce hyphal branching in arbuscular mycorrhizal fungi. *Nature* 435, 824-827.

Al-Babili S, Bouwmeester H J. 2015. Strigolactones, a novel carotenoid-derived plant hormone. *Annual Review of Plant Biology* 66, 161-186.

Alder A, Jamil M, Marzorati M, Bruno M, Vermathen M, Bigler P, Ghisla S, Bouwmeester H, Beyer P, Al-Babili S. 2012. The path from beta-carotene to carlactone, a strigolactone-like plant hormone. *Science* 335, 1348-1351.

Beveridge C A. 2014. Strigolactones. *Current Biology* 24, 987-988.

Booker J, Sieberer T, Wright W, Williamson L, Willett B, Stirnberg P, Turnbull C, Srinivasan M, Goddard P, Leyser O. 2005. MAX1 encodes a cytochrome P450 family member that acts downstream of MAX3/4 to produce a carotenoid-derived branch-inhibiting hormone. *Developmental Cell* 8, 443-449.

Boyer F D, de Saint Germain A, Pouvreau J B, Clave G, Pillot J P, Roux A, Rasmussen A, Depuydt S, Lauressergues D, Frey N F D, Heugebaert T S A, Stevens C V, Geelen D, Goormachtig S, Rameau C. 2014. New strigolactone analogs as plant hormones with low activities in the rhizosphere. *Molecular Plant* 7, 675-690.

Brewer P B, Yoneyama K, Filardo F, Meyers E, Scaffidi A, Frickey T, Akiyama K, Seto Y, Dun E A, Cremer J E, Kerr S C, Waters M T, Flematti G R, Mason M G, Weiller G, Yamaguchi S, Nomura T, Smith S M, Yoneyama K, Beveridge C A. 2016. LATERAL BRANCHING OXIDOREDUCTASE acts in the final stages of strigolactone biosynthesis in *Arabidopsis*. *Proceedings of the National Academy of Sciences* 113, 6301-6306.

Bruno M, Hofmann M, Vermathen M, Alder A, Beyer P, Al-Babili S. 2014. On the substrate and stereospecificity of the plant CAROTENOID CLEAVAGE DIOXYGENASE 7. *FEBS Letters* 588, 1802-1807.

Bruno M, Al-Babili S. 2016. On the substrate specificity of the rice strigolactone biosynthesis enzyme DWARF27. *Planta* 243, 1429-1440.

Bruno M, Vermathen M, Alder A, Wüst F, Schaub P, Steen R, Beyer P, Ghisla S, Al-Babili S. 2017. Insights into the formation of carlactone from in☐depth analysis of the CCD8☐catalyzed reactions. *FEBS Letters* 591, 792-800.

Charnikhova T V, Gaus K, Lumbroso A, Sanders M, Vincken J-P, De Mesmaeker A, Ruyter-Spira C P, Screpanti C, Bouwmeester H J. 2017. Zealactones. Novel natural strigolactones from maize. *Phytochemistry* 137, 123-131.

Conn C E, Bythell-Douglas R, Neumann D, Yoshida S, Whittington B, Westwood J H, Shirasu K, Bond C S, Dyer K A, Nelson D C. 2015. Convergent evolution of strigolactone perception enabled host detection in parasitic plants. *Science* 349, 540-543.

de Saint Germain A, Clave G, Badet-Denisot M A, Pillot J P, Cornu D, Le Caer J P, Burger M, Pelissier F, Retailleau P, Turnbull C, Bonhomme S, Chory J, Rameau C, Boyer F D. 2016. An histidine covalent receptor and butenolide complex mediates strigolactone perception. *Nature Chemical Biology* 12, 787-795.

Decker E L, Alder A, Hunn S, Ferguson J, Lehtonen M T, Scheler B, Kerres K L, Wiedemann G, Safavi-Rizi V, Nordzieke S. 2017. Strigolactone biosynthesis is evolutionarily conserved, regulated by phosphate starvation and contributes to resistance against phytopathogenic fungi in a moss, *Physcomitrella patens*. *New Phytologist doi:* 10.1111/nph.14506.

Delavault P, Montiel G, Brun G, Pouvreau J-B, Thoiron S, Simier P. 2016. Communication between host plants and parasitic plants. *Advances in Botanical Research* 82, 1-28.

Dor E, Joel D M, Kapulnik Y, Koltai H, Hershenhorn J. 2011. The synthetic strigolactone GR24 influences the growth pattern of phytopathogenic fungi. *Planta* 234:419-27.

Ejeta G. 2007. Breeding for *Striga* resistance in sorghum: Exploitation of an intricate host-parasite biology. *Crop Science* 47, 216-227.

Foo E, Davies N W. 2011. Strigolactones promote nodulation in pea. *Planta* 234:1073-81.

Fukui K, Ito S, Asami T. 2013. Selective mimics of strigolactone actions and their potential use for controlling damage caused by root parasitic weeds. *Molecular Plant* 6, 88-99.

Gomez-Roldan V, Fermas S, Brewer P B, Puech-Pages V, Dun E A, Pillot J P, Letisse F, Matusova R, Danoun S, Portais J C, Bouwmeester H, Becard G, Beveridge C A, Rameau C, Rochange S F. 2008. Strigolactone inhibition of shoot branching. *Nature* 455, 189-194.

Gutjahr C, Parniske M. 2013. Cell and developmental biology of arbuscular mycorrhiza symbiosis. *Annual review of cell and developmental biology* 29:593-617.

Ha C V, Leyva-Gonzalez M A, Osakabe Y, Tran U T, Nishiyama R, Watanabe Y, Tanaka M, Seki M, Yamaguchi S, Dong N V, Yamaguchi-Shinozaki K, Shinozaki K, Herrera-Estrella L, Tran L S P. 2014. Positive regulatory role of strigolactone in plant responses to drought and salt stress. *Proceedings of the National Academy of Sciences of the United States of America* 111, 851-856.

Hamiaux C, Drummond R S M, Janssen B J, Ledger S E, Cooney J M, Newcomb R D, Snowden K C. 2012. DAD2 Is an alpha/beta hydrolase likely to be involved in the perception of the plant branching hormone, strigolactone. *Current Biology* 22, 2032-2036.

Hearne S J. 2009. Control—the *Striga* conundrum. *Pest management science* 65:603-14.

Humphrey A J, Galster A M, Beale M H. 2006. Strigolactones in chemical ecology: waste products or vital allelochemicals? *Natural Product Reports* 23, 592-614.

Jamil M, Kanampiu F K, Karaya H, Charnikhova T, Bouwmeester H J. 2012. *Striga* hermonthica parasitism in maize in response to N and P fertilisers. *Field Crops Research* 134, 1-10.

Jia K P, Kountche B A, Jamil M, Guo X J, Ntui V O, Rufenacht A, Rochange S, Al-Babili S. 2016. Nitro-Phenlactone, a carlactone analog with pleiotropic strigolactone activities. *Molecular Plant* 9, 1341-1344.

Jiang L, Liu X, Xiong G S, Liu H H, Chen F L, Wang L, Meng X B, Liu G F, Yu H, Yuan Y D, Yi W, Zhao L H, Ma H L, He Y Z, Wu Z S, Melcher K, Qian Q, Xu H E, Wang Y H, Li J Y. 2014. DWARF 53 acts as a repressor of strigolactone signalling in rice *Nature* 506, 401-411.

Joel D M. 2000. The long-term approach to parasitic weeds control: manipulation of specific developmental mechanisms of the parasite. *Crop Protection* 19, 753-758.

Kgosi R L, Zwanenburg B, Mwakaboko A S, Murdoch A J. 2012. Strigolactone analogues induce suicidal seed germination of *Striga* spp. in soil. *Weed Research* 52, 197-203.

Lopez-Obando M, Ligerot Y, Bonhomme S, Boyer F D, Rameau C. 2015. Strigolactone biosynthesis and signaling in plant development. *Development* 142:3615-9.

Lumba S, Holbrook-Smith D, McCourt P. 2017. The perception of strigolactones in vascular plants. *Nature Chemical Biology* 13, 599-606.

Malik H, Kohlen W, Jamil M, Rutjes F, Zwanenburg B. 2011. Aromatic A-ring analogues of orobanchol, new germination stimulants for seeds of parasitic weeds. *Organic & Biomolecular Chemistry* 9, 2286-2293.

Mangnus E M, Vanvliet L A, Vandenput D A L, Zwanenburg B. 1992. Structural modification of strigol analogs-influence of the B and C rings on the bioactivity of the germination stimulant GR24. *Journal of Agricultural and Food Chemistry* 40, 1222-1229.

Matthys C, Walton A, Struk S, Stes E, Boyer F-D, Gevaert K, Goormachtig S. 2016. The Whats, the Wheres and the Hows of strigolactone action in the roots. *Planta* 243, 1327-1337.

Matusova R, Rani K, Verstappen F W, Franssen M C, Beale M H, Bouwmeester H J. 2005. The strigolactone germination stimulants of the plant-parasitic *Striga* and *Orobanche* spp. are derived from the carotenoid pathway. *Plant physiology* 139:920-34.

Morffy N, Faure L, Nelson D C. 2016. Smoke and Hormone Mirrors: Action and Evolution of Karrikin and Strigolactone Signaling. *Trends in genetics: TIG* 32:176-88.

Nelson D C, Flematti G R, Ghisalberti E L, Dixon K, Smith S M. 2012. Regulation of seed germination and seedling growth by chemical signals from burning vegetation. *Annual Review of Plant Biology* 63, 107-130.

Parker C. 2009. Observations on the current status of *Orobanche* and *Striga* problems worldwide. *Pest Management Science* 65, 453-459.

Parker C. 2012. Parasitic weeds: a world challenge. *Weed Science* 60, 269-276.

Pennisi E. 2010. Armed and dangerous. *Science* 327, 1200-1200.

Rasmussen A, Mason M G, De Cuyper C, Brewer P B, Herold S, Agusti J, Geelen D, Greb T, Goormachtig S, Beeckman T, Beveridge C A. 2012. Strigolactones suppress adventitious rooting in *Arabidopsis* and Pea. *Plant Physiology* 158, 1976-1987.

Reizelman A, Scheren M, Nefkens G H L, Zwanenburg B. 2000. Synthesis of all eight stereoisomers of the germination stimulant strigol. *Synthesis-Stuttgart* 13, 1944-1951.

Ritz C, Streibig J C. 2005. Bioassay analysis using R. *Journal of Statistical Software* 12, 1-22.

Rodenburg J, Cissoko M, Kayongo N, Dieng I, Bisikwa J, Irakiza R, Masoka I, Midega C A, Scholes J D. 2017. Genetic variation and host-parasite specificity of *Striga* resistance and tolerance in rice: the need for predictive breeding. *New Phytologist* 214, 1267-1280.

Ruyter-Spira C, Al-Babili S, van der Krol S, Bouwmeester H. 2013. The biology of strigolactones. *Trends in Plant Science* 18, 72-83.

Samejima H, Babiker A G, Takikawa H, Sasaki M, Sugimoto Y. 2016. Practicality of the suicidal germination approach for controlling *Striga* hermonthica. *Pest Management Science* 72, 2035-2042.

Screpanti C, Fonné-Pfister R, Lumbroso A, Rendine S, Lachia M, De Mesmaeker A. 2016. Strigolactone derivatives for potential crop enhancement applications. *Bioorganic & Medicinal Chemistry Letters* 26, 2392-2400.

Seto Y, Sado A, Asami K, Hanada A, Umehara M, Akiyama K, Yamaguchi S. 2014. Carlactone is an endogenous biosynthetic precursor for strigolactones. *Proceedings of the National Academy of Sciences* 111, 1640-1645.

Stirnberg P, Furner I J, Leyser H M O. 2007. MAX2 participates in an SCF complex which acts locally at the node to suppress shoot branching. *Plant Journal* 50, 80-94.

Tank D C, Beardsley P M, Kelchner S A, Olmstead R G. 2006. Review of the systematics of Scrophulariaceae s.l. and their current disposition. *Australian Systematic Botany* 19:289-307.

Torres-Vera R, Garcia J M, Pozo M J, Lopez-Raez J A. 2014. Do strigolactones contribute to plant defense? *Molecular Plant Pathology* 15, 211-216.

Tsuchiya Y, Yoshimura M, Sato Y, Kuwata K, Toh S, Holbrook-Smith D, Zhang H, McCourt P, Itami K, Kinoshita T, Hagihara S. 2015. Probing strigolactone receptors in *Striga hermonthica* with fluorescence. *Science* 349, 864-868.

Ueno K, Fujiwara M, Nomura S, Mizutani M, Sasaki M, Takikawa H, Sugimoto Y. 2011. Structural requirements of strigolactones for germination induction of *Strigagesnerioides* seeds. *Journal of Agricultural and Food Chemistry* 59, 9226-9231.

Ueno K, Furumoto T, Umeda S, Mizutani M, Takikawa H, Batchvarova R, Sugimoto Y. 2014. Heliolactone, a non-sesquiterpene lactone germination stimulant for root parasitic weeds from sunflower. *Phytochemistry* 108, 122-128.

Umehara M, Hanada A, Yoshida S, Akiyama K, Arite T, Takeda-Kamiya N, Magome H, Kamiya Y, Shirasu K, Yoneyama K, Kyozuka J, Yamaguchi S. 2008. Inhibition of shoot branching by new terpenoid plant hormones. *Nature* 455, 195-200.

Waters M. T., Gutjahr C., Bennett T., D. C. N. 2017. Strigolactone signaling and evolution. *Annu. Rev. Plant Biol.* 68, 916-925.

Wigchert S C M, Kuiper E, Boelhouwer G J, Nefkens G H L, Verkleij J A C, Zwanenburg B. 1999. Dose-response of seeds of the parasitic weeds *Striga* and *Orobanche* toward the synthetic germination stimulants G R 24 and Nijmegen-1. *Journal of Agricultural and Food Chemistry* 47, 1705-1710.

Wu L, Yang H Q. 2010. CRYPTOCHROME 1 Is Implicated in promoting R protein mediated plant resistance to *Pseudomonas syringae* in *Arabidopsis*. *Molecular Plant* 3, 539-548.

Xie X, Yoneyama K, Kisugi T, Uchida K, Ito S, Akiyama K, Hayashi H, Yokota T, Nomura T, Yoneyama K. 2013. Confirming stereochemical structures of strigolactones produced by rice and tobacco. *Molecular Plant* 6, 153-163.

Xie X N, Yoneyama K, Yoneyama K. 2010. The strigolactone story. *Annual Review of Phytopathology* 48, 93-117.

Yamada Y, Furusawa S, Nagasaka S, Shimomura K, Yamaguchi S, Umehara M. 2014. Strigolactone signaling regulates rice leaf senescence in response to a phosphate deficiency. *Planta* 240, 399-408.

Yao R F, Ming Z H, Yan L M, Li S H, Wang F, Ma S, Yu C T, Yang M, Chen L, Chen L H, Li Y W, Yan C, Miao D, Sun Z Y, Yan J B, Sun Y N, Wang L, Chu J F, Fan S L, He W, Deng H T, Nan F J, Li J Y, Rao Z H, Lou Z Y, Xie D X. 2016. DWARF14 is a non-canonical hormone receptor for strigolactone. *Nature* 536, 469-473.

Yoneyama K, Awad A A, Xie X, Yoneyama K, Takeuchi Y. 2010. Strigolactones as germination stimulants for root parasitic plants. *Plant & cell physiology* 51:1095-103.

Zhang Y X, van Dijk A D J, Scaffidi A, Flematti G R, Hofmann M, Charnikhova T, Verstappen F, Hepworth J, van der Krol S, Leyser O, Smith S M, Zwanenburg B, Al-Babili S, Ruyter-Spira C, Bouwmeester H J. 2014. Rice cytochrome P450 MAX1 homologs catalyze distinct steps in strigolactone biosynthesis. *Nature Chemical Biology* 10, 1028-1033.

Zhou F, Lin Q B, Zhu L H, Ren Y L, Zhou K N, Shabek N, Wu F Q, Mao H B, Dong W, Gan L, Ma W W, Gao H, Chen J, Yang C, Wang D, Tan J J, Zhang X, Guo X P, Wang J L, Jiang L, Liu X, Chen W Q, Chu J F, Yan C Y, Ueno K, Ito S, Asami T, Cheng Z J, Wang J, Lei C L, Zhai H Q, Wu C Y, Wang H Y, Zheng N, Wan J M. 2013. D14-SCFD3-dependent degradation of D53 regulates strigolactone signalling. *Nature* 504, 406-410.

Zwanenburg B, Mwakaboko A S, Reizelman A, Anilkumar G, Sethumadhavan D. 2009. Structure and function of natural and synthetic signalling molecules in parasitic weed germination. *Pest management science* 65:478-91.

Zwanenburg B, Nayak S K, Charnikhova T V, Bouwmeester H J. 2013. New strigolactone mimics: Structure-activity relationship and mode of action as germinating stimulants for parasitic weeds. *Bioorganic & Medicinal Chemistry Letters* 23, 5182-5186.

Zwanenburg B, Pospisil T. 2013. Structure and activity of strigolactones: New plant hormones with a rich future. *Molecular Plant* 6, 38-62.

Zwanenburg B, Pospisil T, Zeljkovic S C. 2016. Strigolactones: new plant hormones in action. *Planta* 243, 1311-1326.

What is claimed is:

1. A composition comprising at least one compound which is represented by formula II:

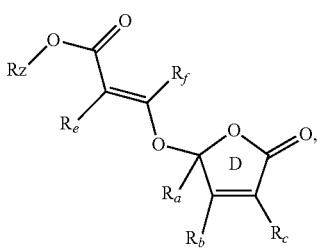

Formula II wherein Re is an optionally substituted C6-C24 aryl group or an optionally substituted C6-C24 alkylaryl group;

wherein Rz is (i) a monovalent optionally substituted C1-C12 alkyl group, or (ii) a bivalent optionally substituted C1-C12 alkylene group, which bonds to the optionally substituted C6-C24 aryl group or the optionally substituted C6-C24 alkylaryl group of the Re moiety forming a ring, wherein the ring is an unsaturated lactone;

wherein when Re and/or Rz is a substituted functional group, the substituent is nitro, alkyl, halogen, amino, nitrile, alkoxy, aldehyde, carboxylic acid, ester, or hydroxyl;

wherein $R_f$ represents a hydrogen atom, a halogen atom, a nitro group, a cyano group or C1-C8-alkyl, C2-C8 alkenyl, C2-C8-alkynyl, or C3-C8-cycloalkyl;

wherein when Ra is hydrogen, Rb is hydrogen, and Rc is methyl, Rf is hydrogen; and wherein $R_a$, $R_b$ and $R_c$, independently from each other, represent:

(a) a hydrogen atom, a halogen atom, a nitro group, a cyano group, a formyloxy group, a formylamino group or a carbamate group, (b) a substituent $R_1$, wherein $R_1$ represents C1-C8-alkyl, C2-C8 alkenyl, C2-C8-alkynyl, C3-C8-cycloalkyl, or C1-C8-alkoxy, each of which are optionally substituted, (c) a substituent —$OR_2$, wherein $R_2$ represents a hydrogen atom, C1-C8-alkyl, C2-C8-alkenyl, C2-C8-alkynyl, C1-C8-alkylcarbonyl, C1-C8-alkylaminocarbonyl or C1-C8-alkoxycarbonyl, each of which are optionally substituted, (d) a substituent —$NR_3R_4$, wherein $R_3$ and $R_4$, independently from each other, represent a hydrogen atom, C1-C8 alkyl, C1-C8-alkylcarbonyl, C1-C8-halogenoalkylcarbonyl, phenyl or benzyl, each of which are optionally substituted, (e) a substituent —(O)—R$_5$, wherein R$_5$ represents a hydrogen atom, C1-C8-alkyl or C1-C8-alkyloxy, each of which are optionally substituted, —NH$_2$, NHR$_5$ or NR$_5$R$_5$ where the two substituents R$_5$ may be the same or different, —NR$_5$ (OH), (f) a substituent —S(O)$_n$—R$_6$, wherein n is 0, 1 or 2 and R$_6$ represents C1-C8-alkyl which is optionally substituted, —NH$_2$, —NHR$_6$ or NR$_6$R$_6$ where the two substituents R$_6$ may be the same or different, or (g) a 4-, 5-, 6- or 7-membered heterocyclic ring comprising up to 4 heteroatoms selected from nitrogen, oxygen or sulfur, each of which are optionally substituted, wherein substituents in (a)-(g) are halogen, nitro, amino, nitrile, alkoxy, or hydroxyl; and wherein compounds formula (VI) are excluded:

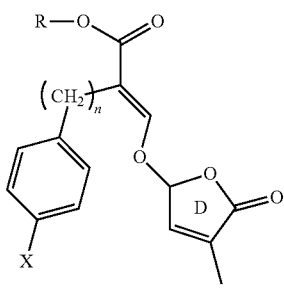

Formula VI wherein:
(i) R is methyl, X is H and n=0;
(ii) R is methyl, X is H, and n=1;
(iii) R is methyl, X is H, and n=2;
(iv) R is methyl, X is Cl, and n=0;
(v) R is methyl, X is —OCH$_3$ and n=0; and
(vi) R is methyl, X is H, n=1, and R is bonded to —(CH$_2$)$_n$-forming a ring.

2. The composition according to claim 1, wherein Re is represented by Formula III:

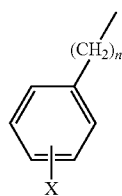

Formula III wherein X of Formula III is a monovalent group which is ortho, meta, or para-substituted, and n is 0, 1, or 2.

3. The composition according to claim 1, wherein Rz is the monovalent optionally substituted C1-C12 alkyl group.

4. The composition according to claim 1, wherein the compound is represented by Formula (IV):

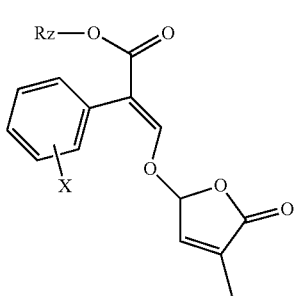

Formula IV wherein Rz a monovalent optionally substituted C1-C12 alkyl group, and X of Formula IV is a monovalent group in the ortho, meta, or para position.

5. The composition of claim 1, wherein Rz is the bivalent optionally substituted C1-C12 alkylene group, which bonds to the aryl moiety of the optionally substituted C6-C24 aryl group or the optionally substituted C6-C24 alkylaryl group of the Re moiety forming a ring, wherein the ring is an unsaturated lactone ring.

6. The composition of claim 1, wherein:
Re is an optionally substituted C6-C24 aryl group;
Rz is (i) a monovalent optionally substituted C1-C12 alkyl group, or (ii) a bivalent optionally substituted C1-C12 alkylene group, which bonds to the optionally substituted C6-C24 aryl group of the Re moiety forming a ring, wherein the ring is an unsaturated lactone ring.

7. A method of controlling a target plant growth, the method comprising applying the composition of claim 1 to the target plant or its habitat, wherein the control of the target plant growth is to discourage or encourage the target plant growth.

8. The method according to claim 7, wherein the control of target plant growth is to encourage the target plant growth.

9. The method according to claim 7, wherein the control of target plant growth is to discourage the target plant growth.

10. The method according to claim 7, wherein the composition stimulates the germination of parasitic root plants.

11. A method of controlling a target plant growth, the method comprising applying the composition of claim 1 to the target plant or its habitat, wherein the control of the target plant growth is discouraging the target plant growth, triggering leaf senescence of the target plant, and/or inhibiting tillering of the target plant.

12. The method of claim 11, wherein the target plant is rice plant and/or *Arabidopsis*.

13. The method of claim 11, wherein the control of target plant growth is to discourage the target plant growth.

14. The method of claim 11, wherein the control of target plant growth includes triggering leaf senescence or inhibiting tillering.

15. The method of claim 11, wherein Rz is the bivalent optionally substituted C1-C12 alkylene group, bonds to the aryl moiety of the optionally substituted C6-C24 aryl group or the optionally substituted C6-C24 alkylaryl group of the Re moiety forming a ring, wherein the ring is an unsaturated lactone ring.

* * * * *